United States Patent
Eggers et al.

(10) Patent No.: US 7,695,505 B2
(45) Date of Patent: Apr. 13, 2010

(54) SYSTEM, METHOD AND APPARATUS FOR EVALUATING TISSUE TEMPERATURE

(75) Inventors: Philip E. Eggers, Dublin, OH (US); John L. Ridihalgh, Columbus, OH (US); Mark Mayerchak, Bothell, WA (US); Gary Altman, Kirkland, WA (US)

(73) Assignee: Apsara, Inc., Columbus, OH (US)

( * ) Notice: Subject to any disclaimer, the term of this patent is extended or adjusted under 35 U.S.C. 154(b) by 1227 days.

(21) Appl. No.: 11/241,081

(22) Filed: Sep. 30, 2005

(65) Prior Publication Data
US 2006/0020312 A1    Jan. 26, 2006

Related U.S. Application Data

(60) Division of application No. 10/733,970, filed on Dec. 11, 2003, now Pat. No. 7,048,756, which is a continuation-in-part of application No. 10/246,347, filed on Sep. 18, 2002, now Pat. No. 6,993,394, which is a continuation of application No. 10/201,363, filed on Jul. 23, 2002, now abandoned.

(60) Provisional application No. 60/349,593, filed on Jan. 18, 2002, provisional application No. 60/466,225, filed on Apr. 28, 2003.

(51) Int. Cl.
*A61F 2/00*    (2006.01)

(52) U.S. Cl. ............................ 607/113; 600/12; 607/96
(58) Field of Classification Search ............. 607/30–33, 607/60–61, 103
See application file for complete search history.

(56) References Cited

U.S. PATENT DOCUMENTS

| | | | |
|---|---|---|---|
| 6,167,313 A * | 12/2000 | Gray et al. .................. 607/103 |
| 6,231,516 B1 * | 5/2001 | Keilman et al. ............. 600/485 |
| 6,366,817 B1 * | 4/2002 | Kung .......................... 607/61 |

* cited by examiner

*Primary Examiner*—Roy D Gibson
(74) *Attorney, Agent, or Firm*—Mueller Smith & Okuley, LLC

(57) ABSTRACT

Method, system and apparatus for monitoring target tissue temperatures wherein temperature sensors are configured as passive resonant circuits each with a unique resonating signature at monitoring temperatures extending below a select temperature setpoint. The resonant circuits are configured with an inductor component formed of windings about a ferrite core having a Curie temperature characteristic corresponding with a desired temperature setpoint. By selecting inductor winding turns and capacitance values, unique resonant center frequencies are detectable. Temperature monitoring can be carried out with implants at lower threshold and upper limit temperature responses. Additionally, the lower threshold sensors may be combined with auto-regulated heater implants having Curie transitions at upper temperature limits.

34 Claims, 61 Drawing Sheets

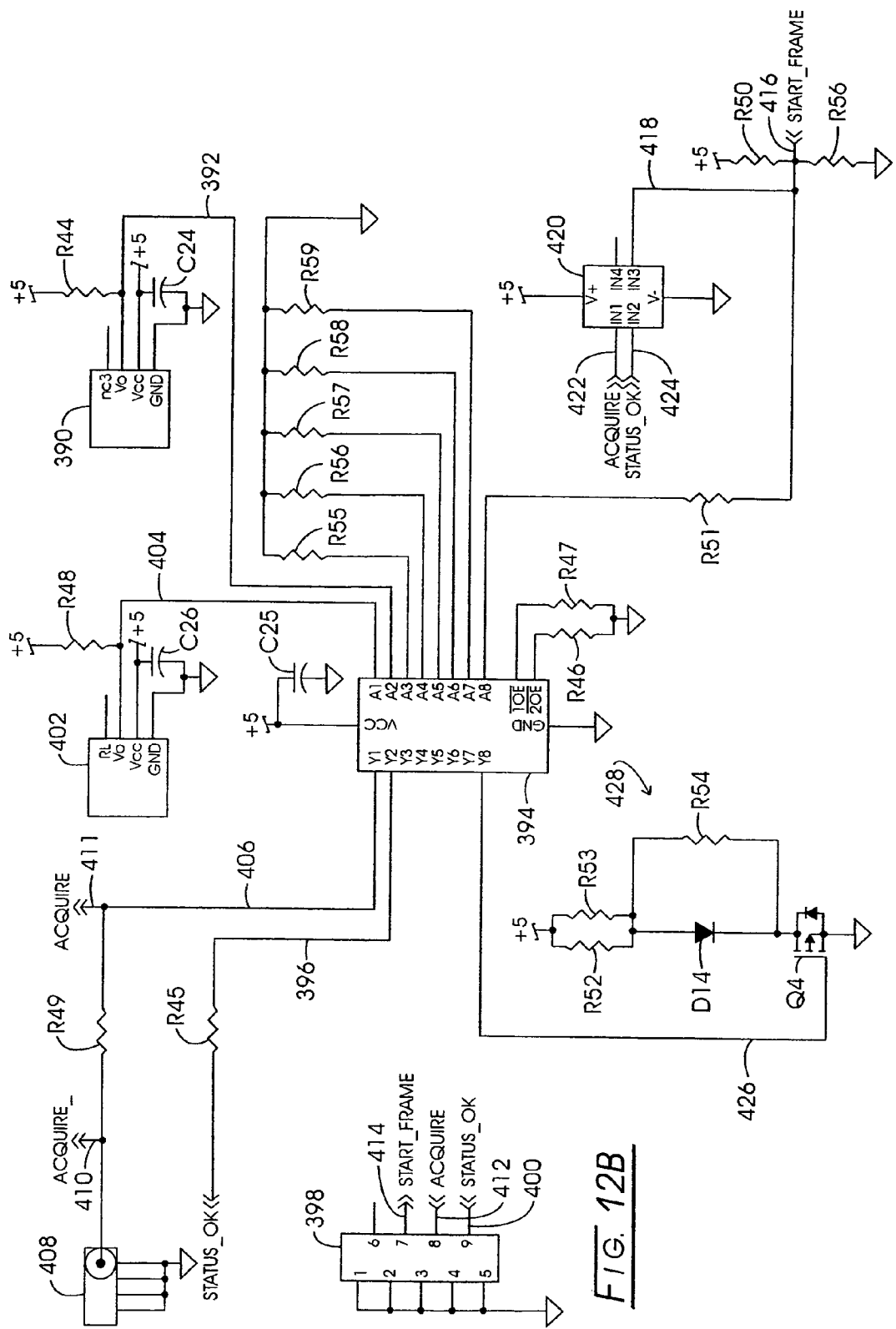

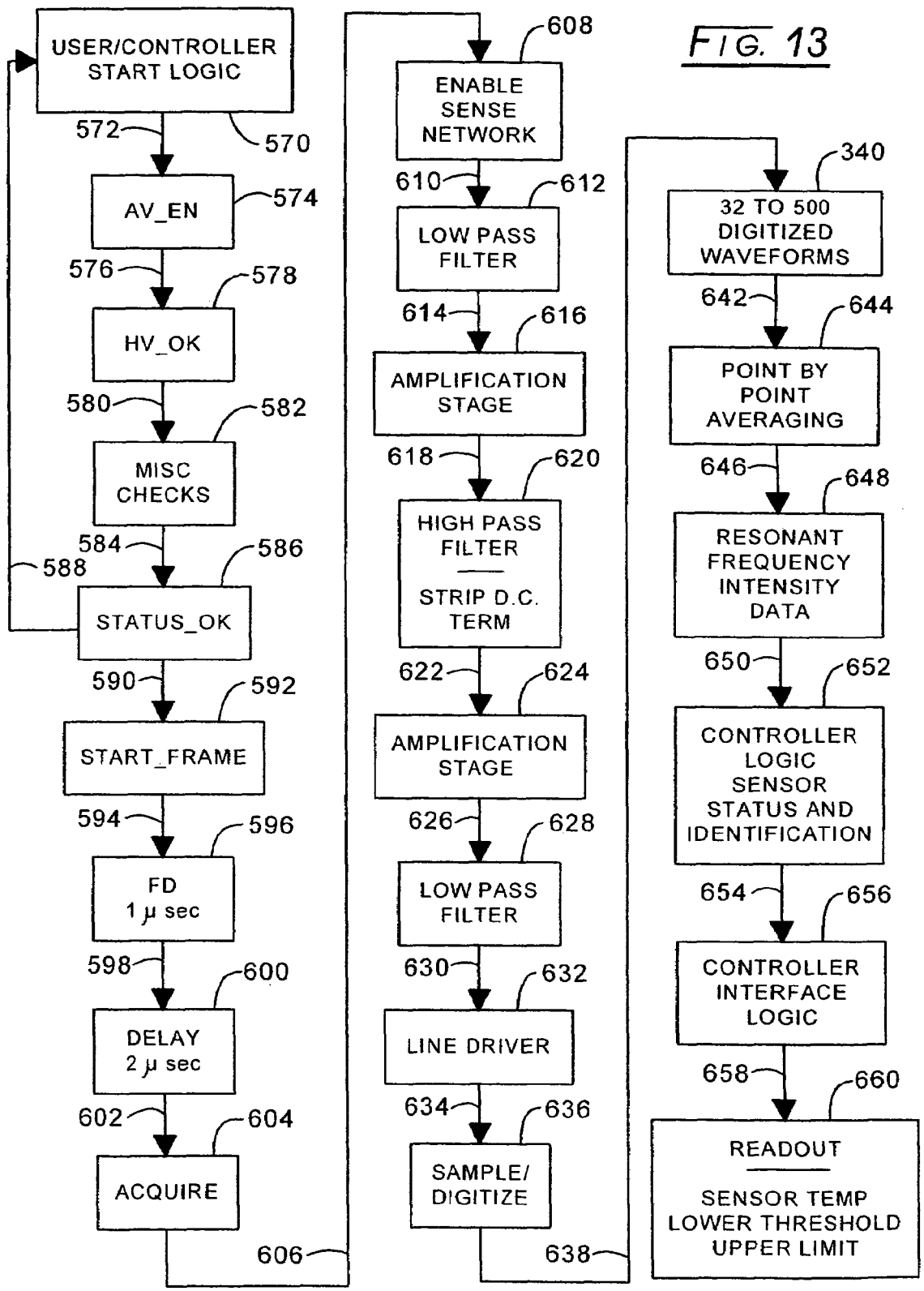

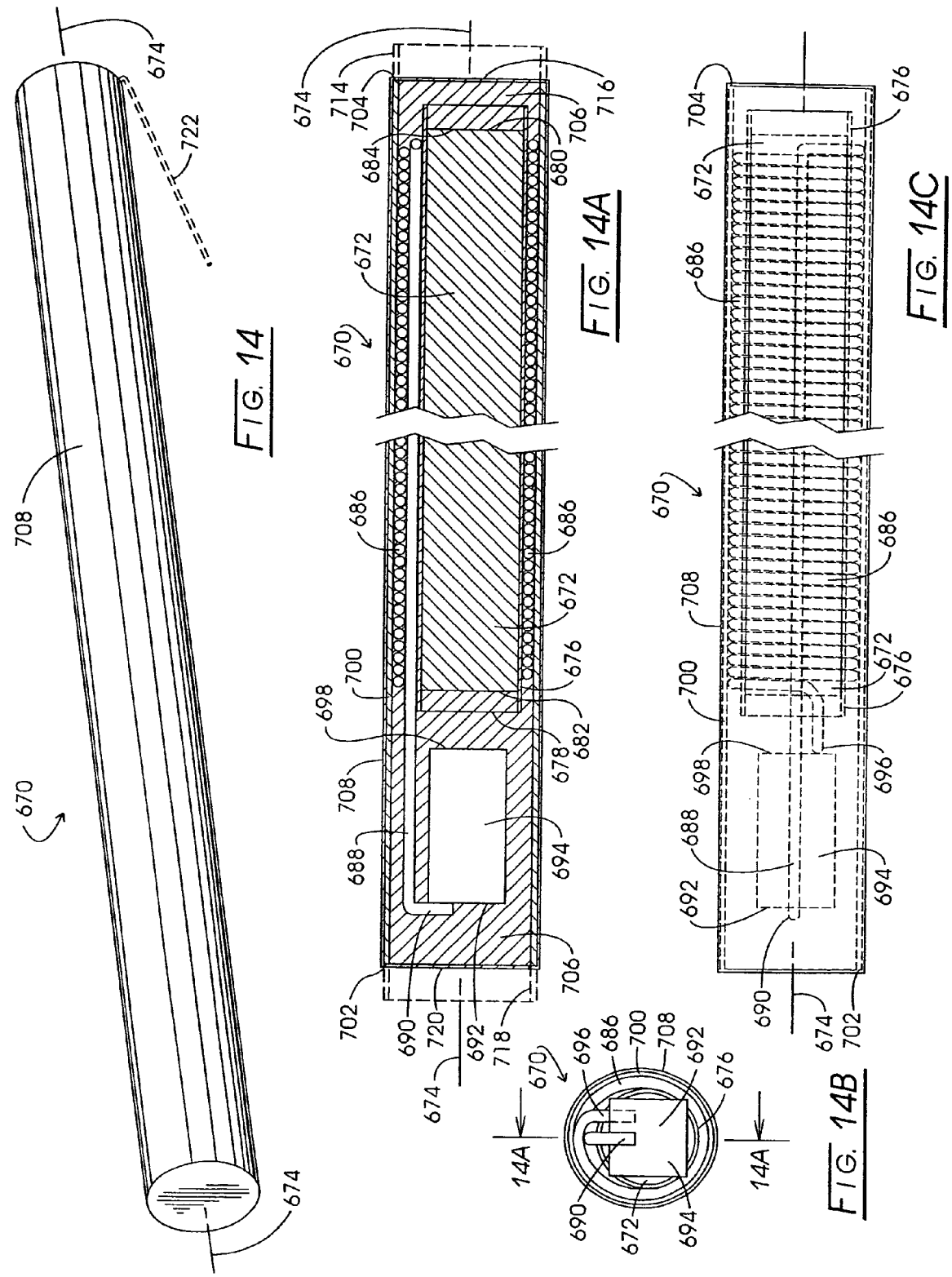

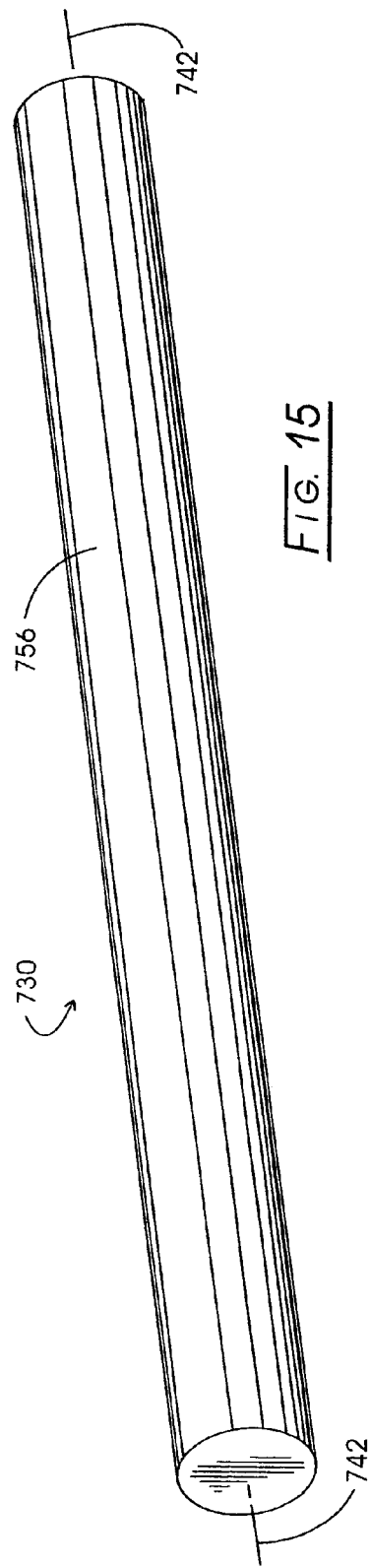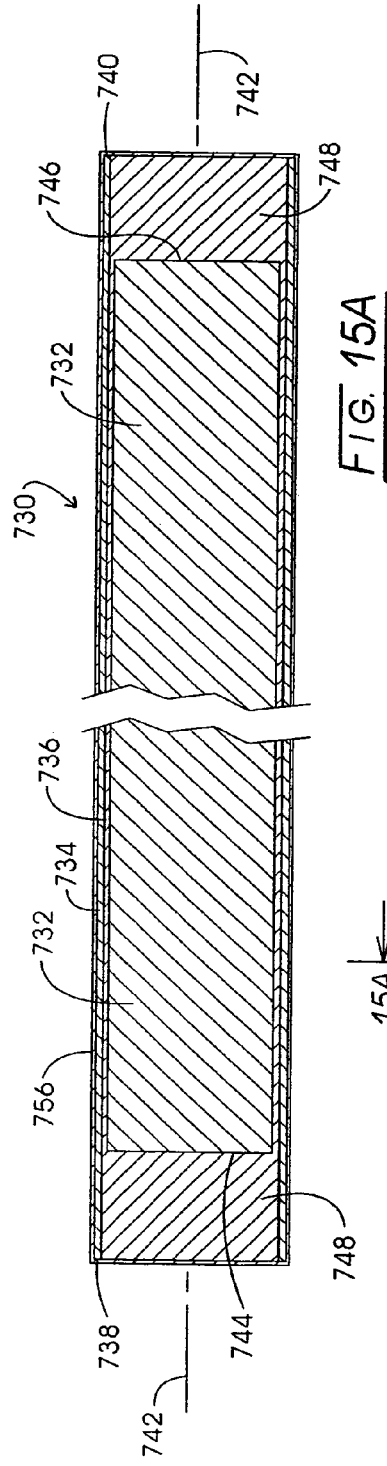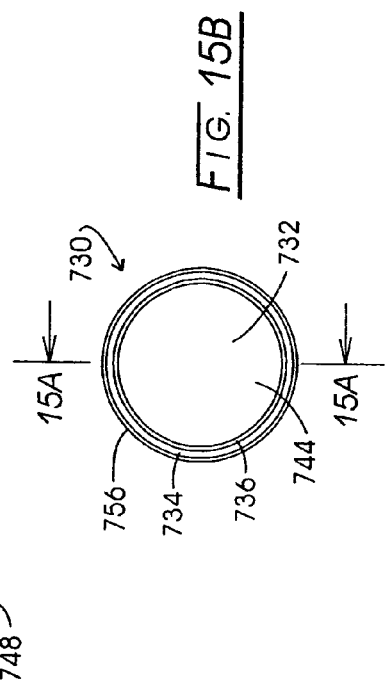

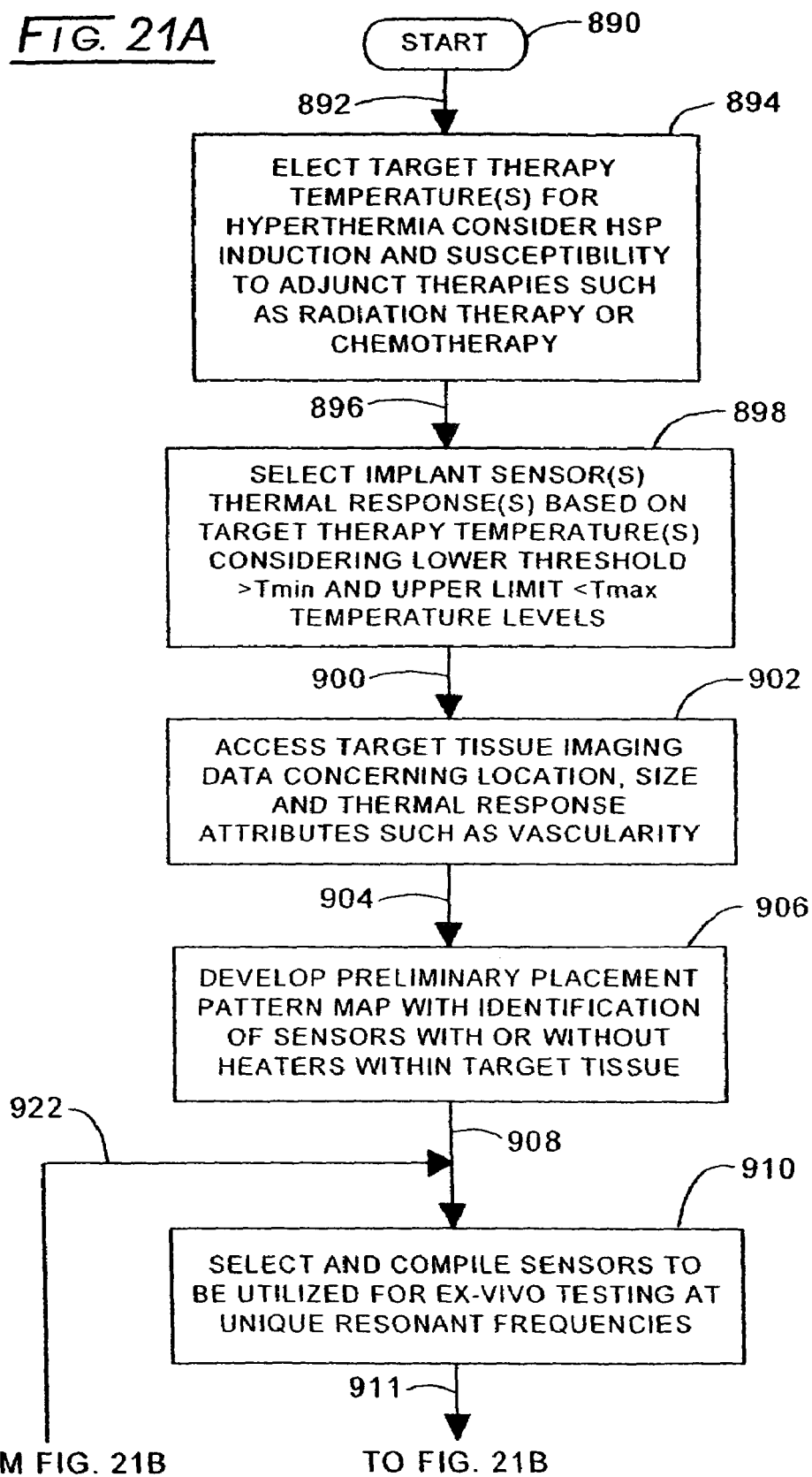

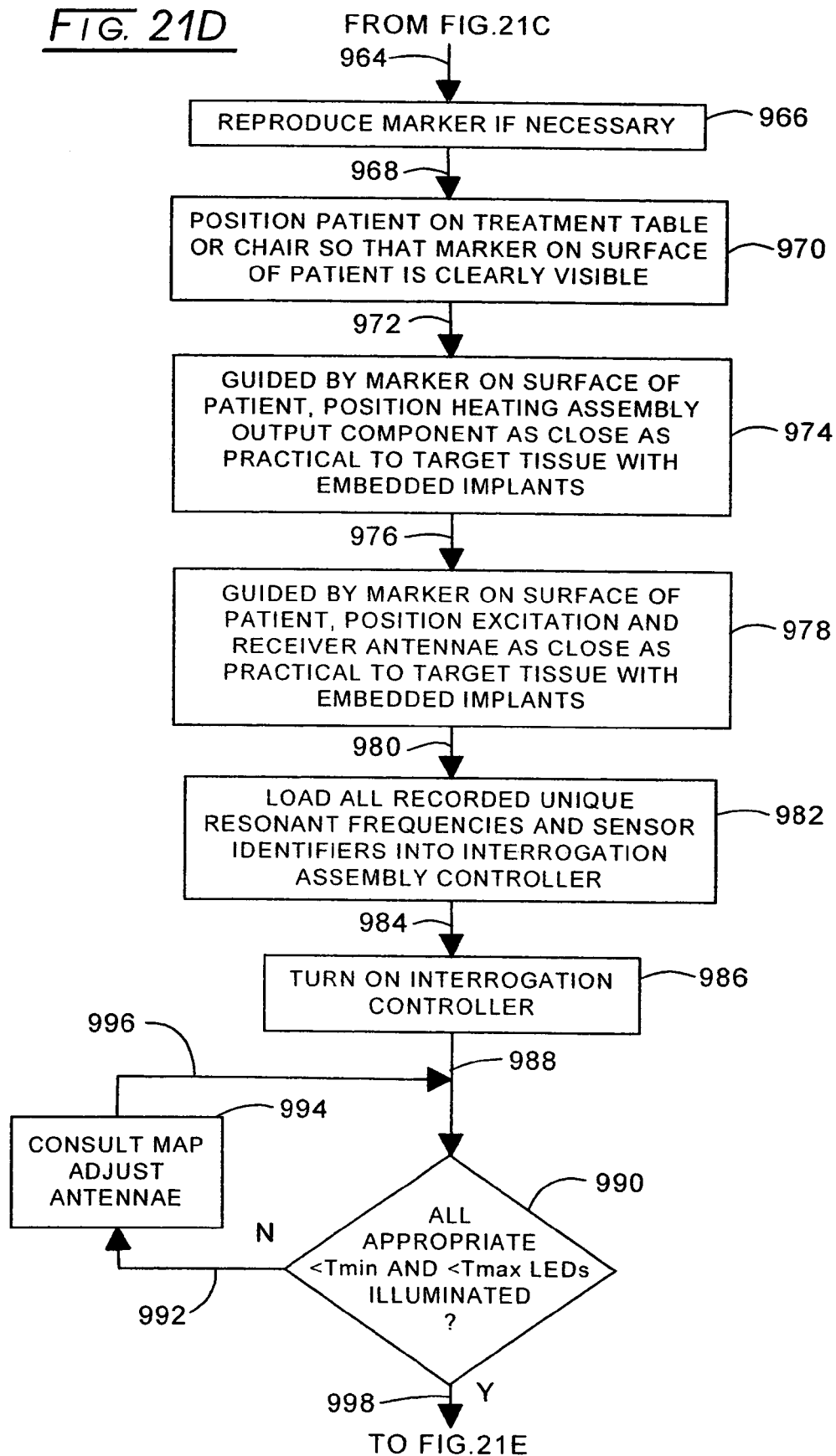

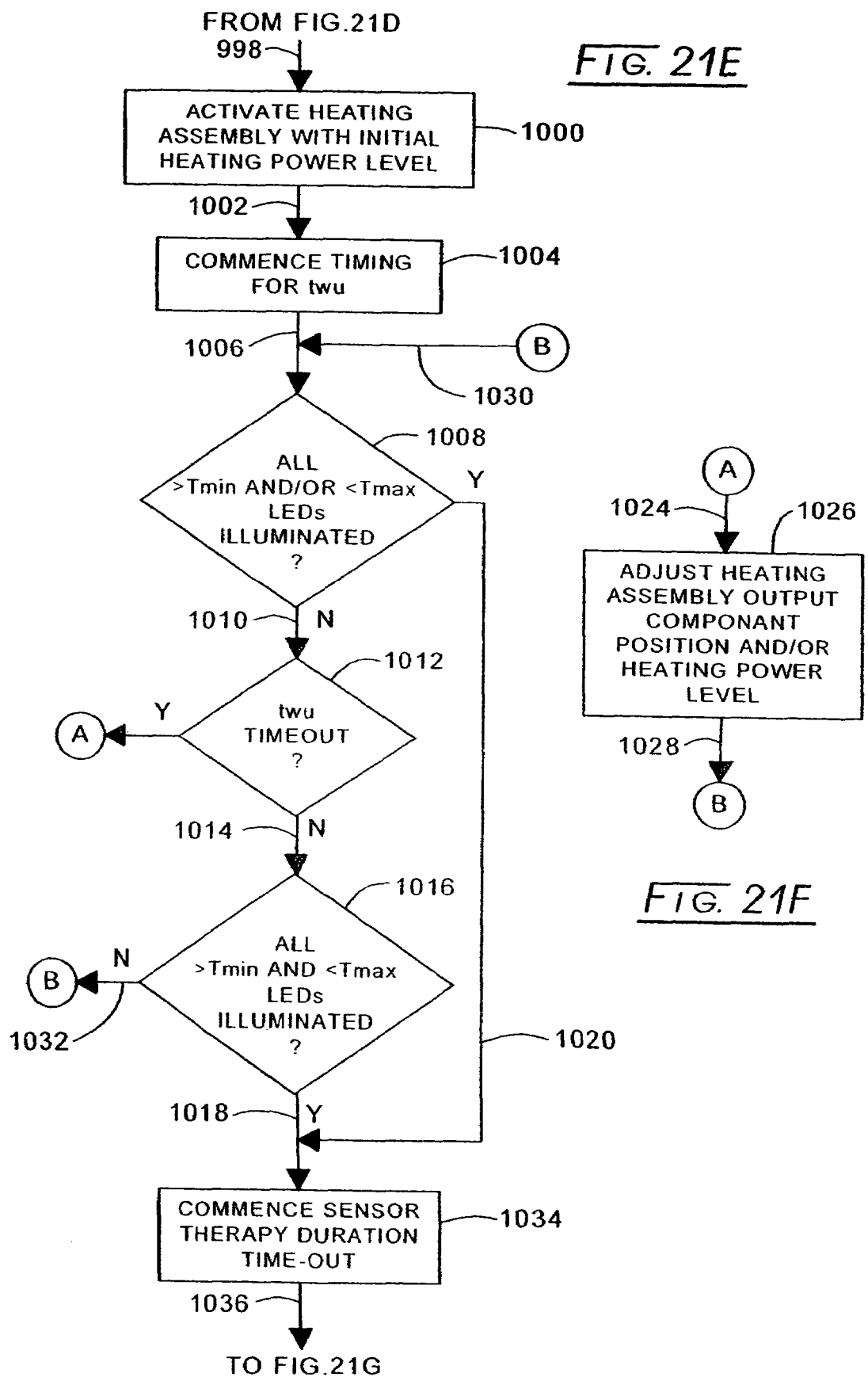

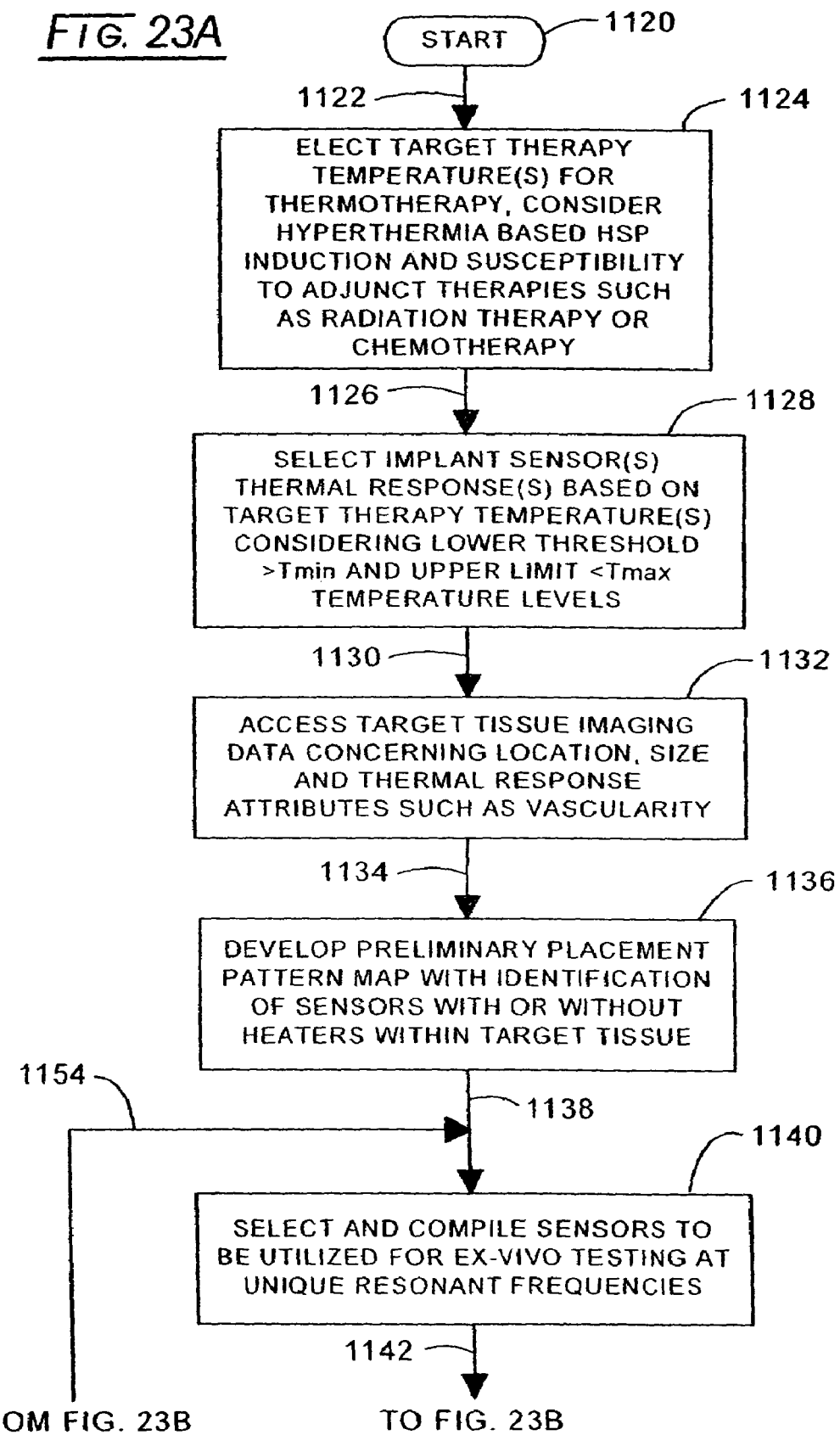

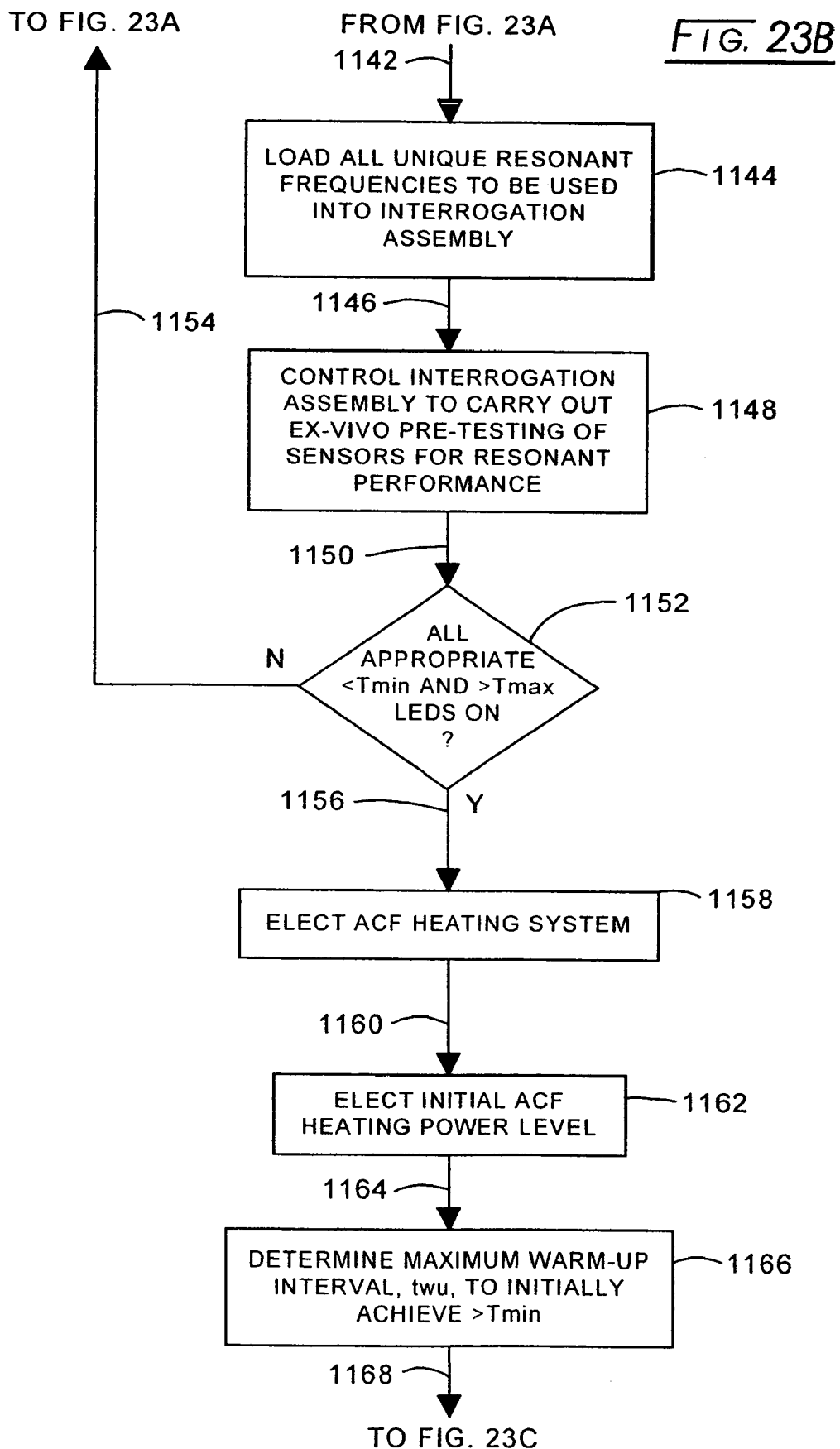

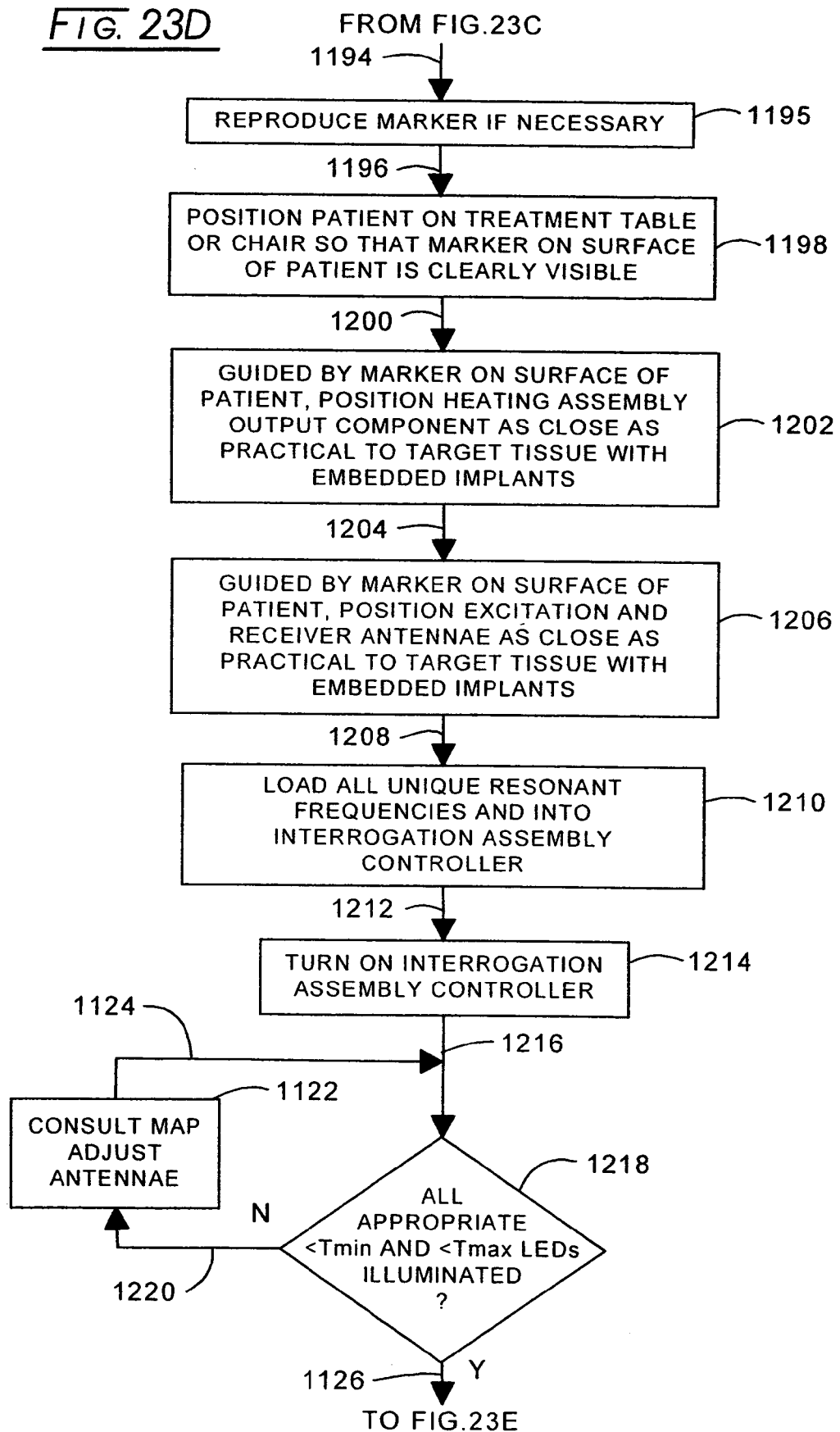

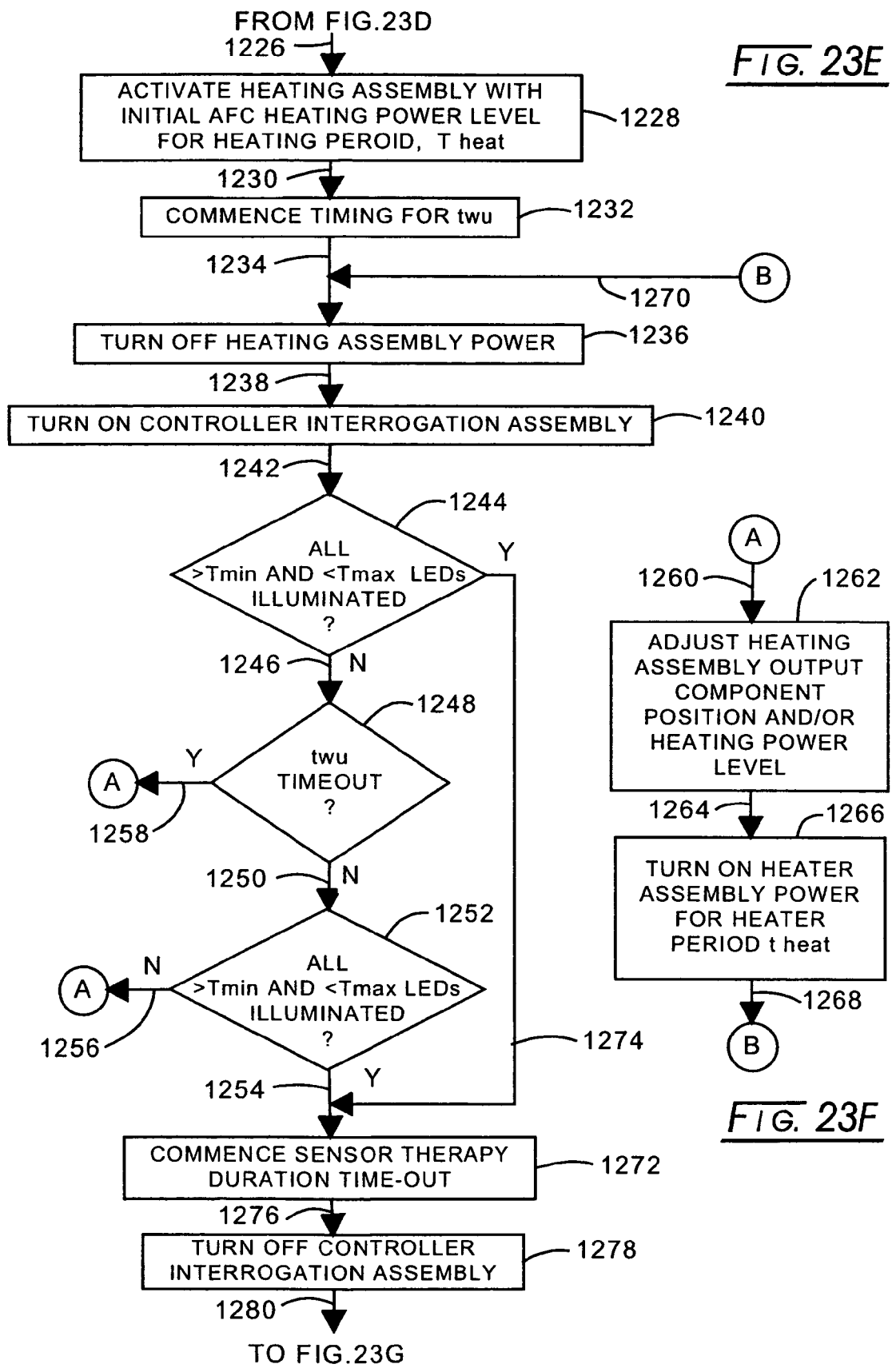

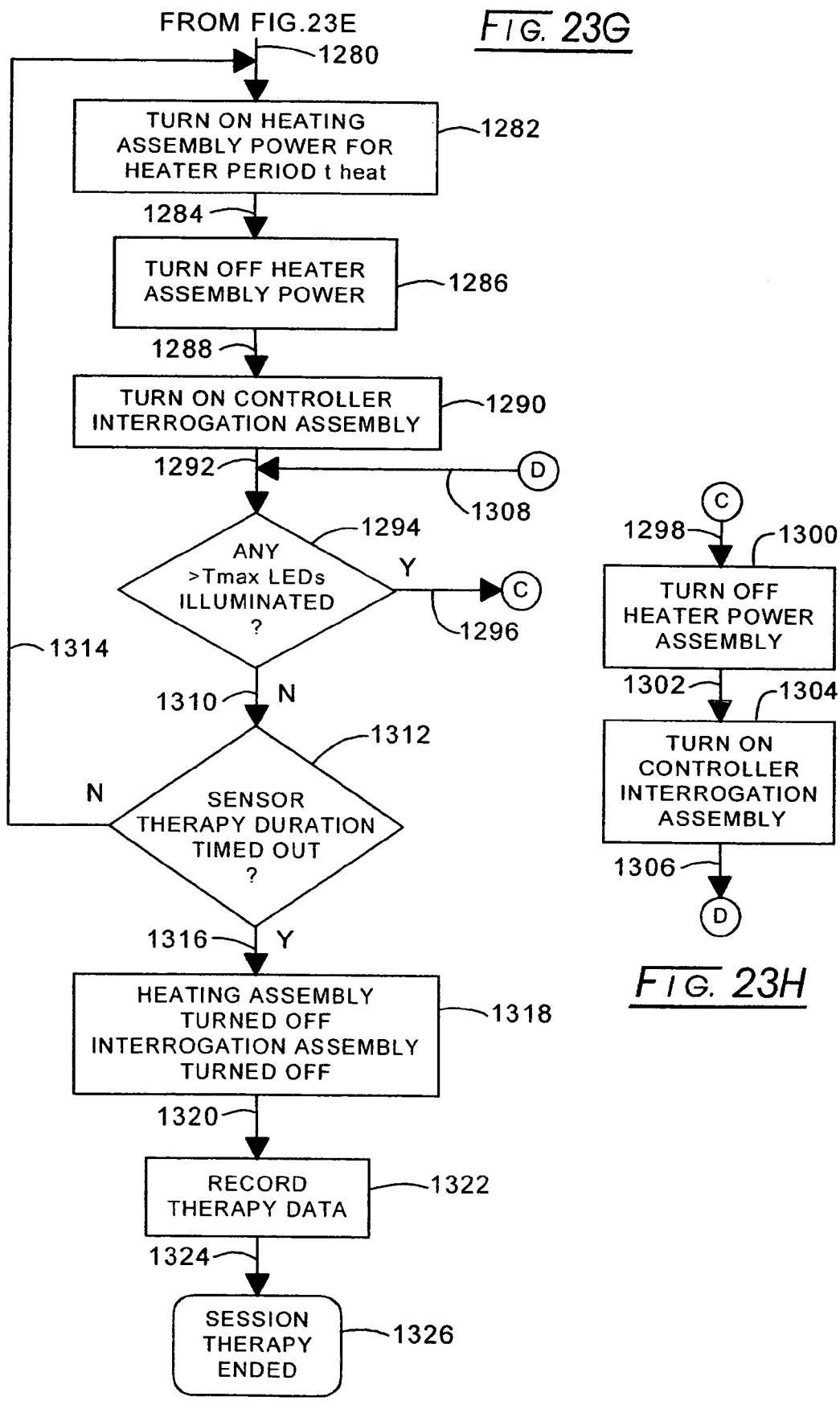

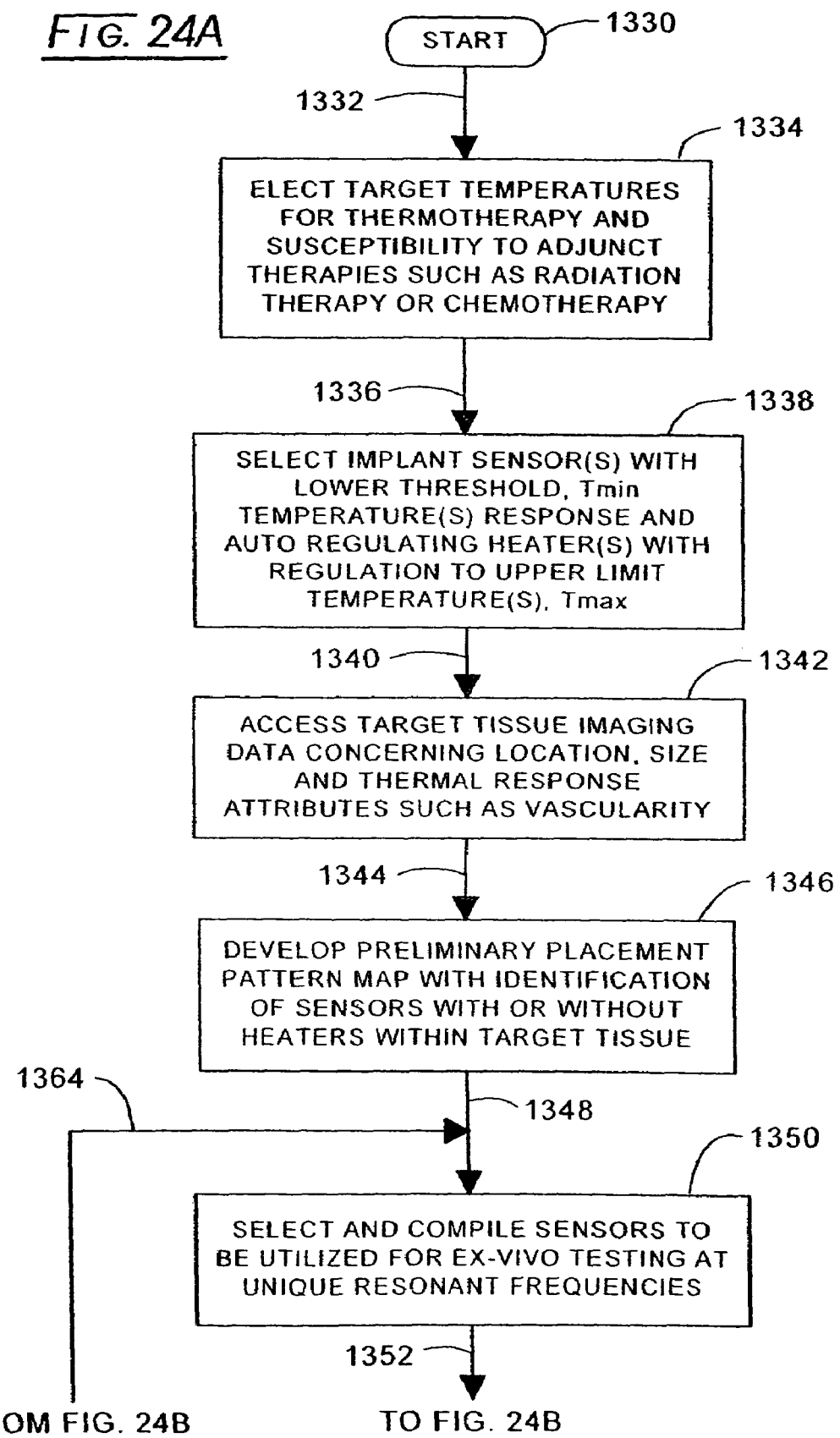

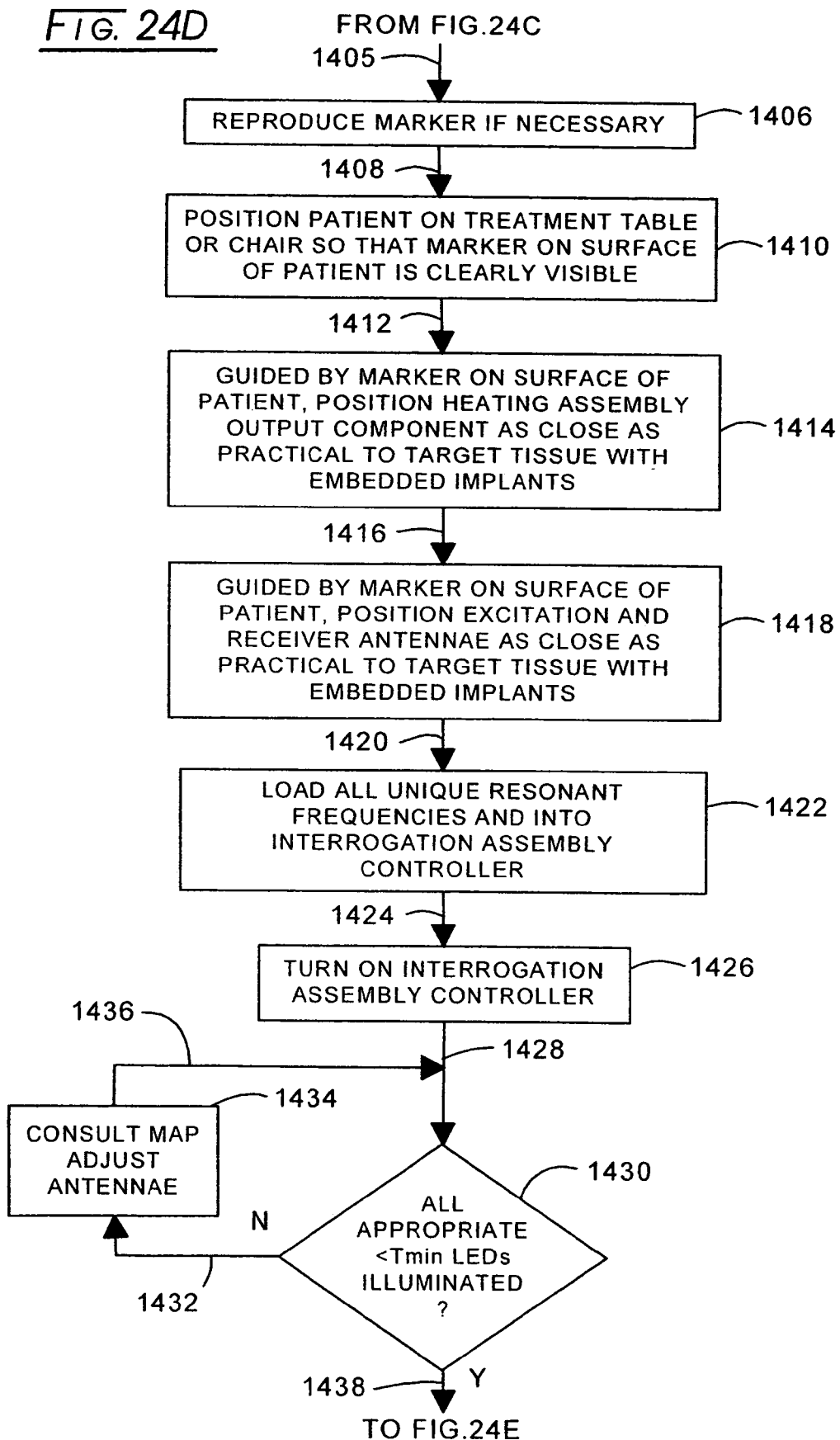

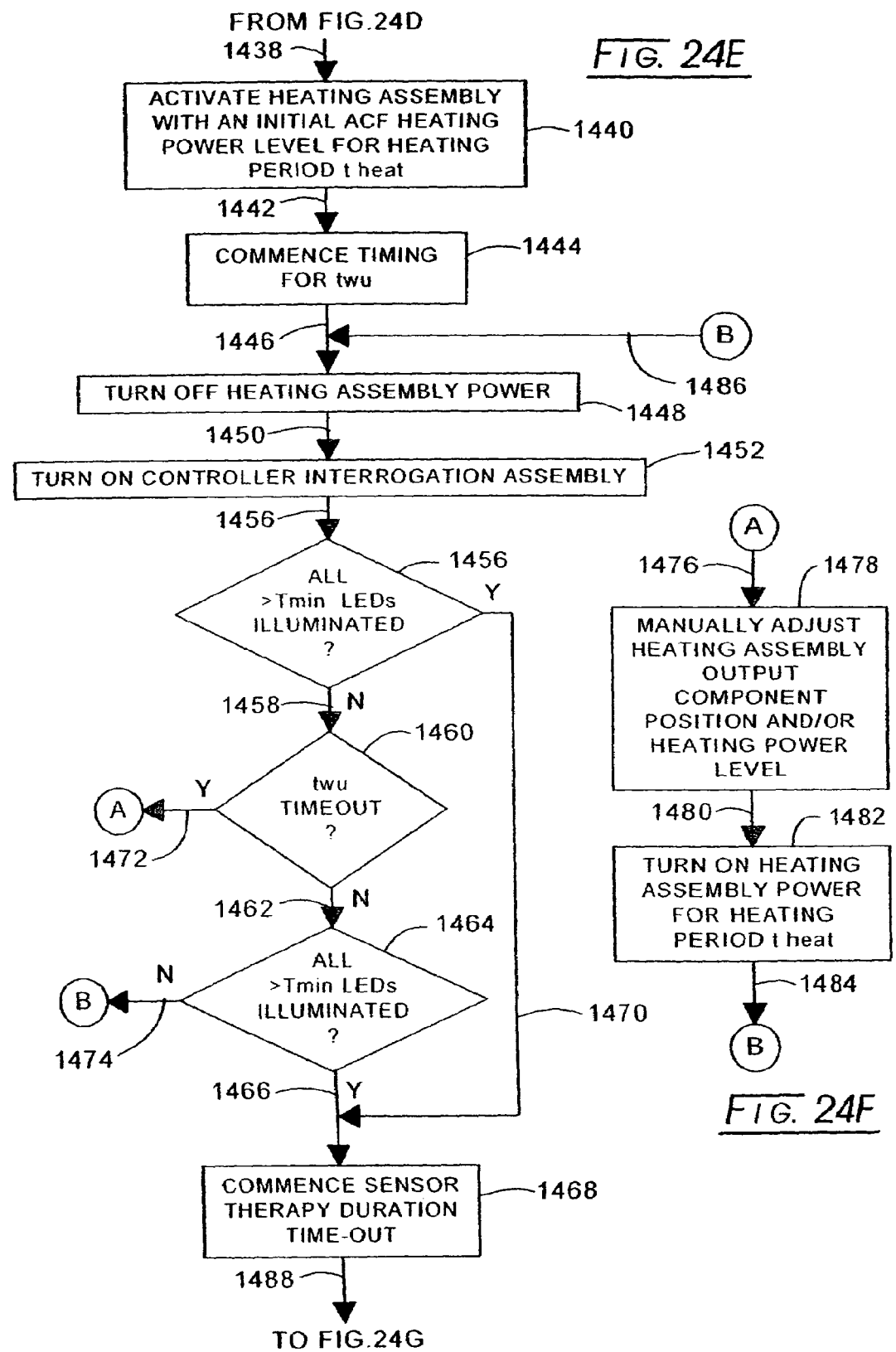

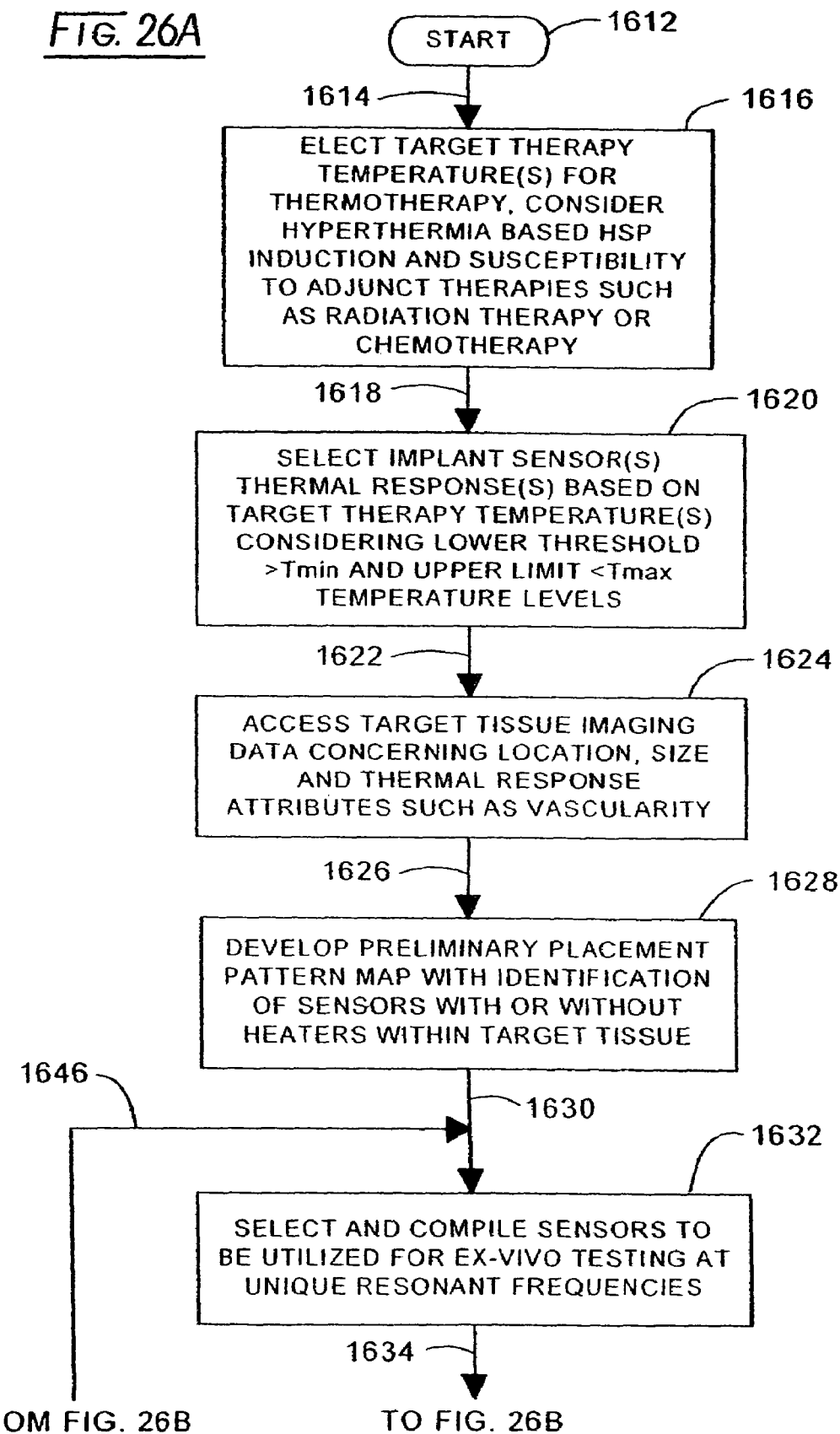

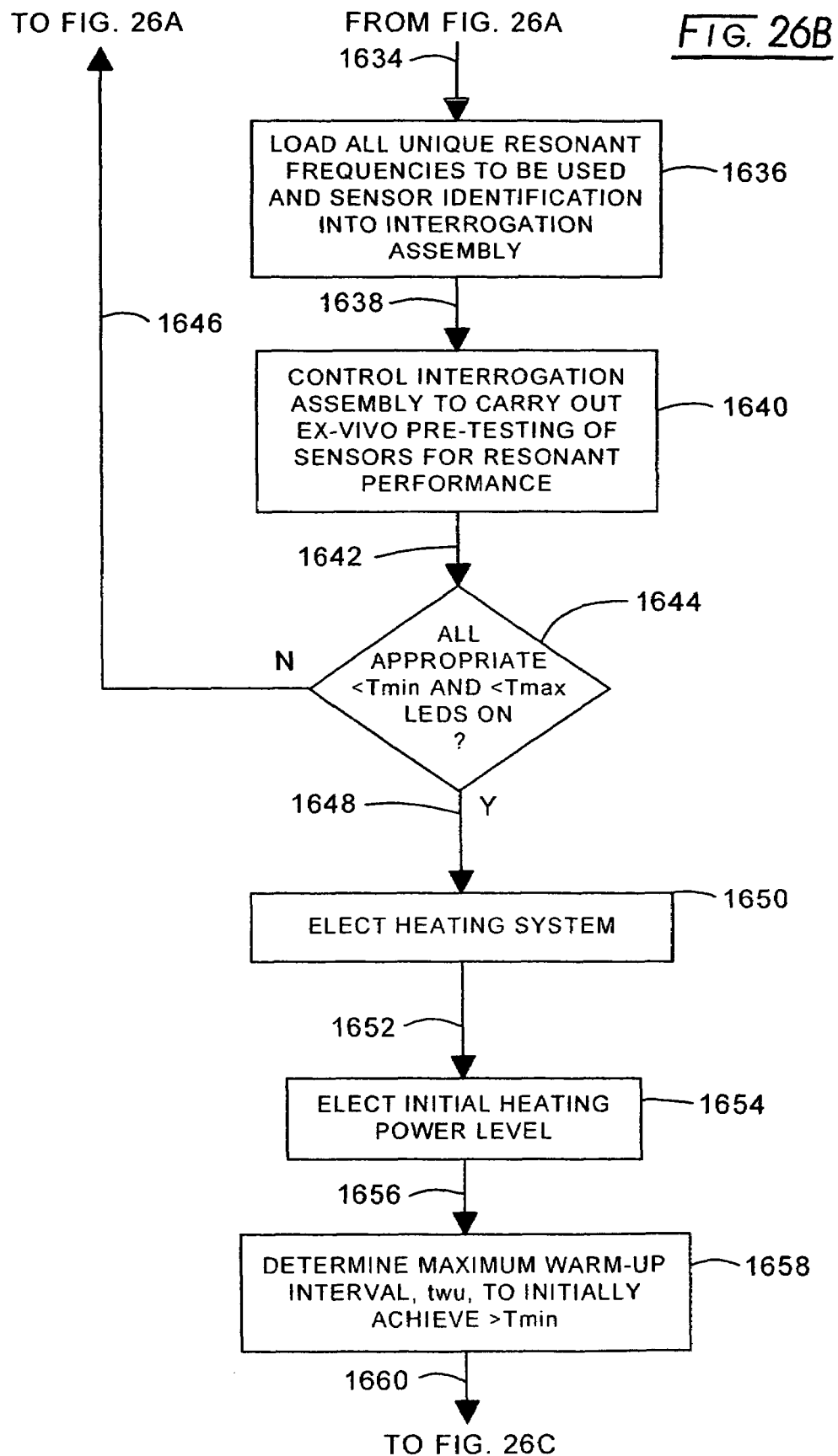

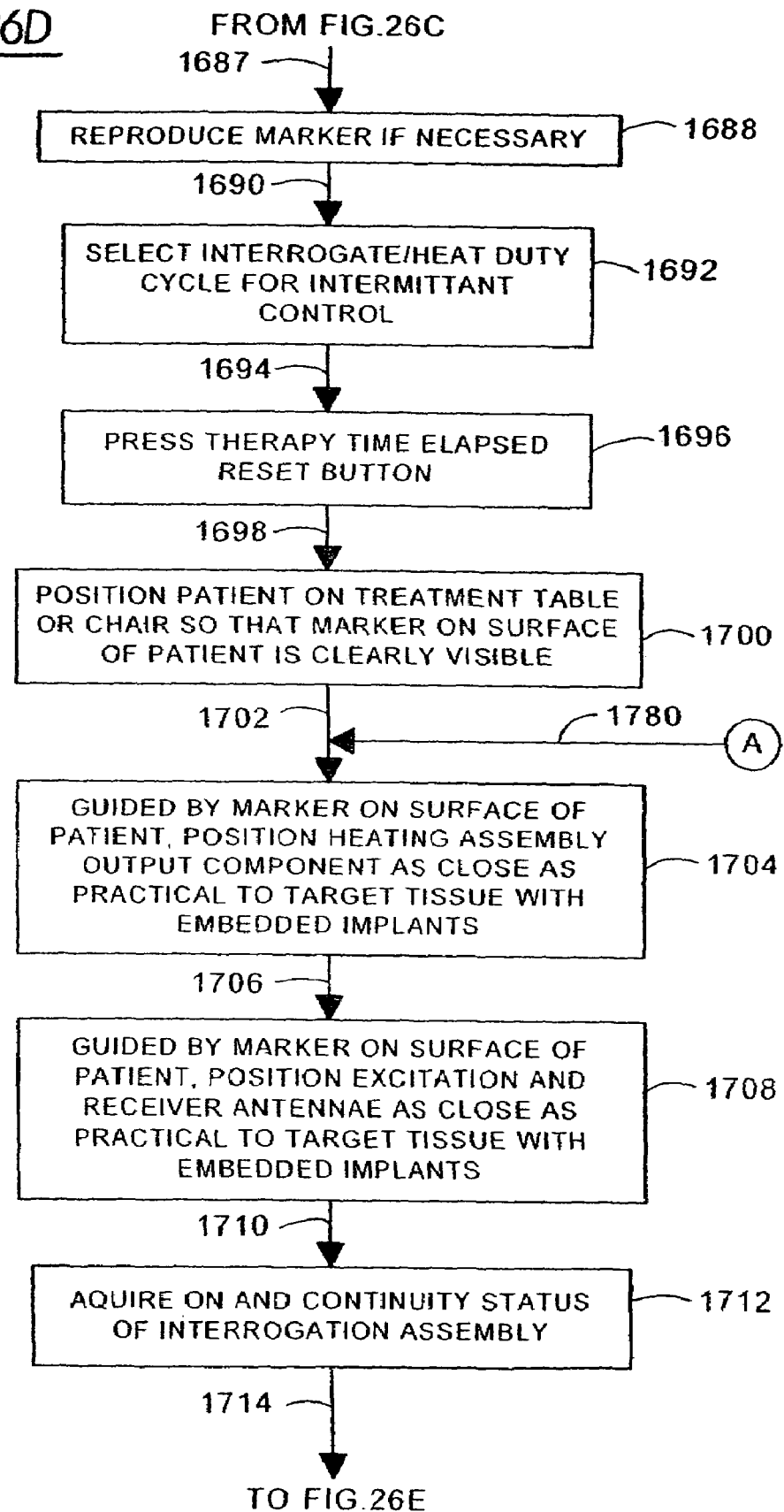

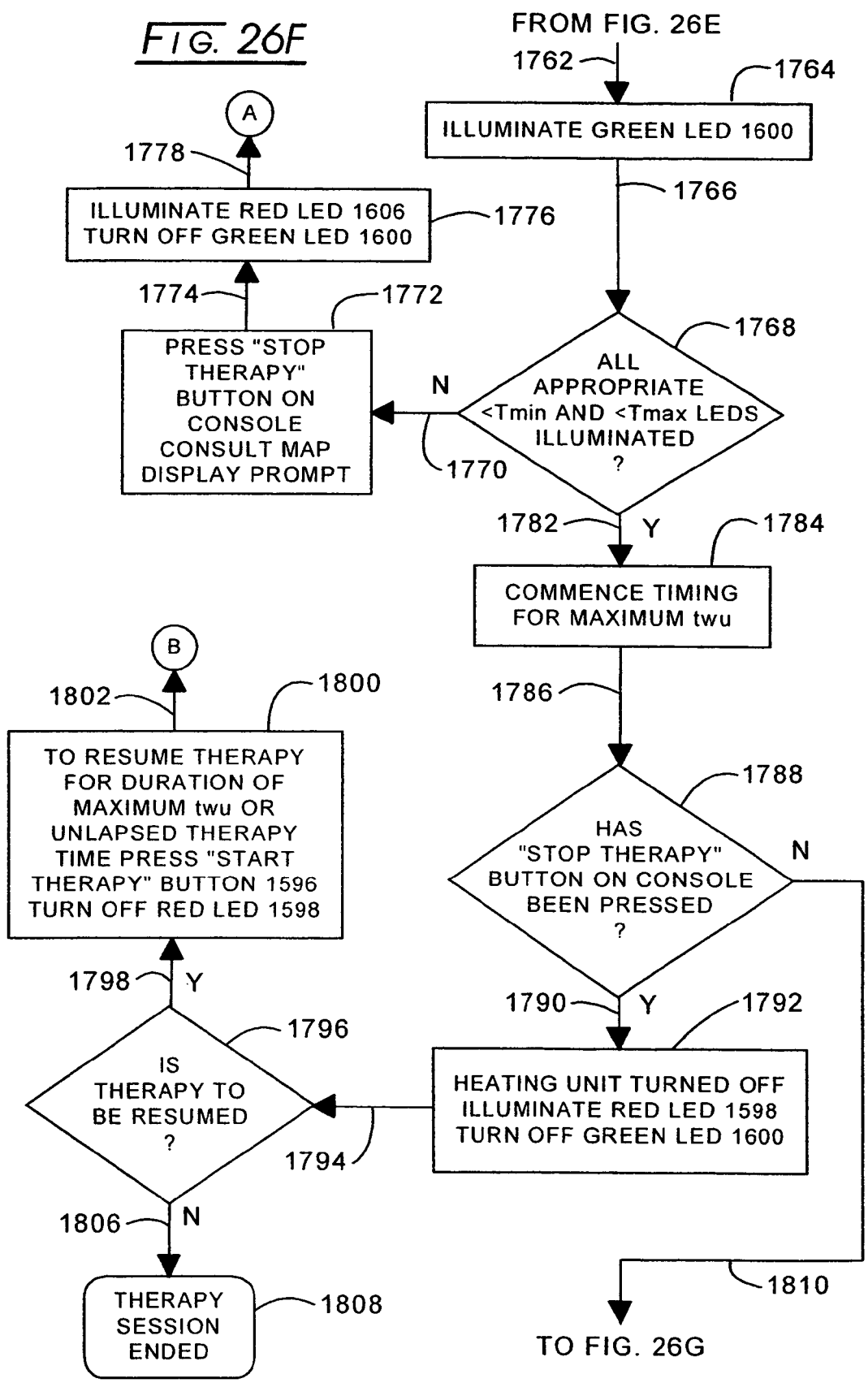

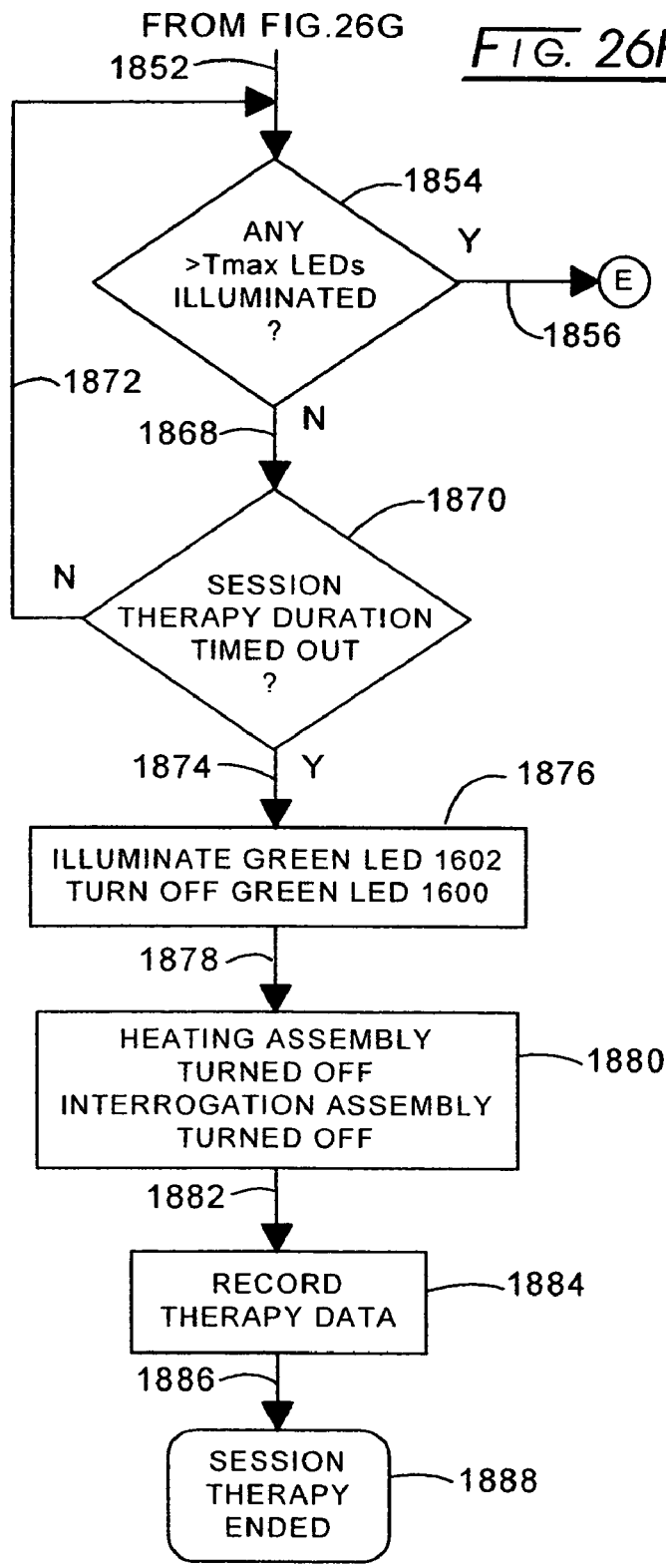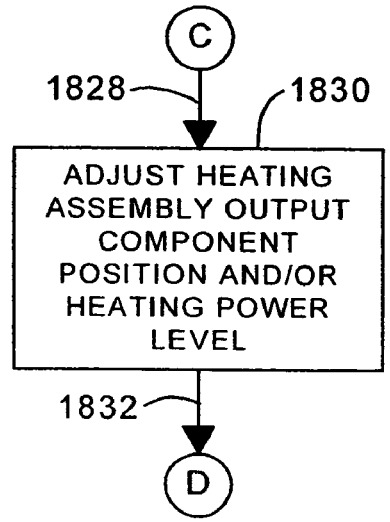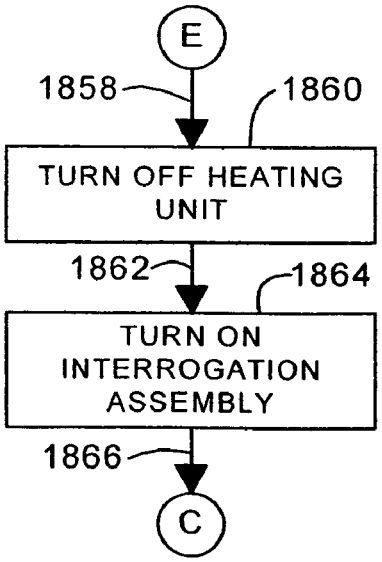

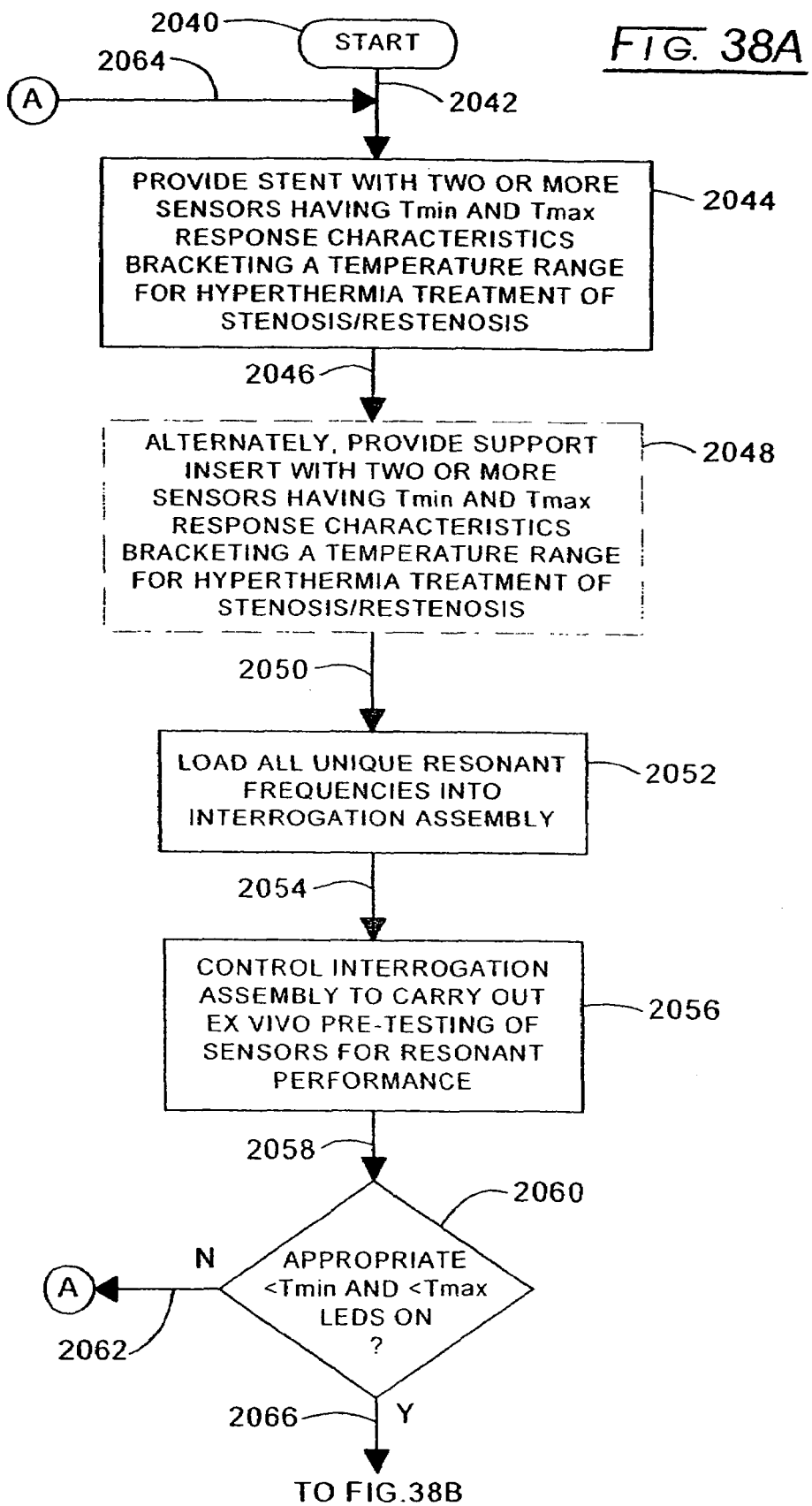

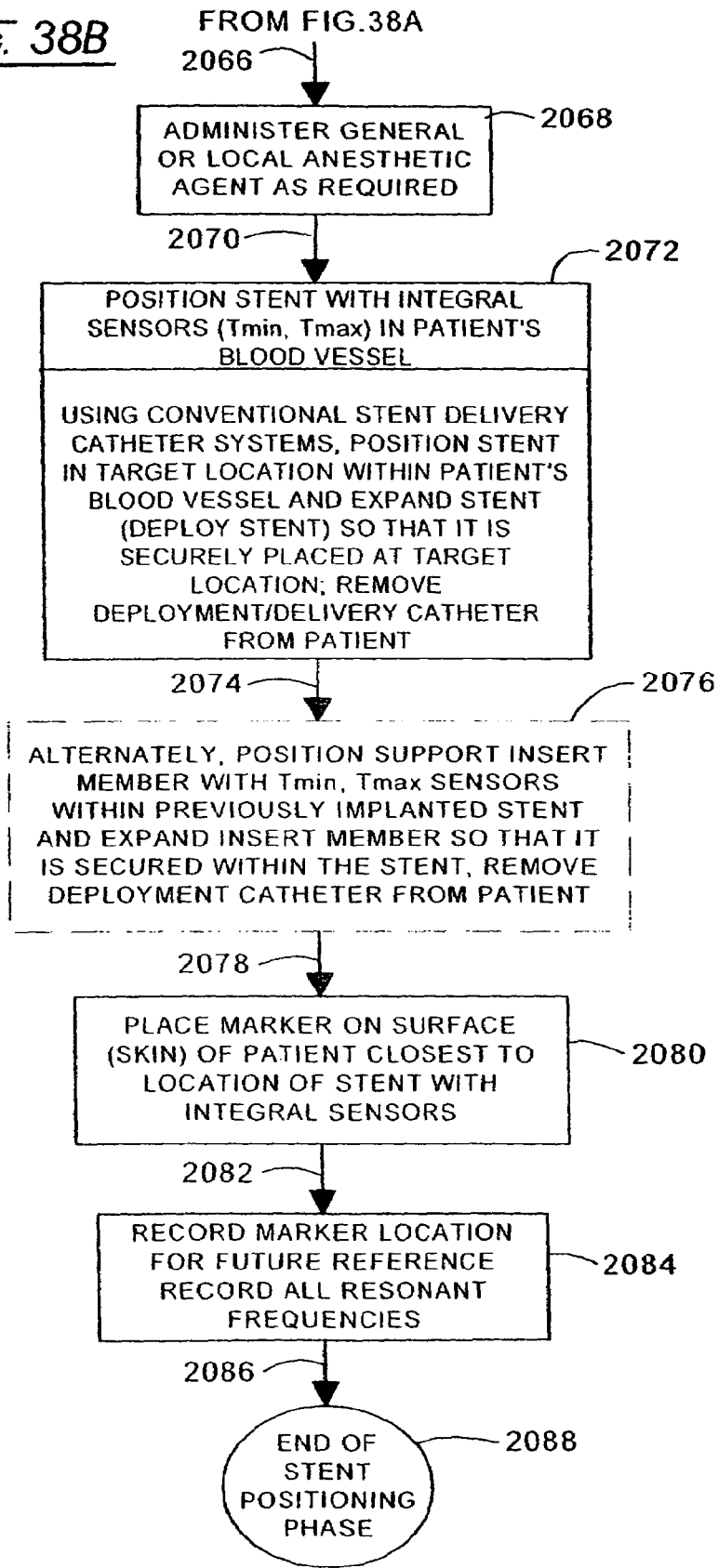

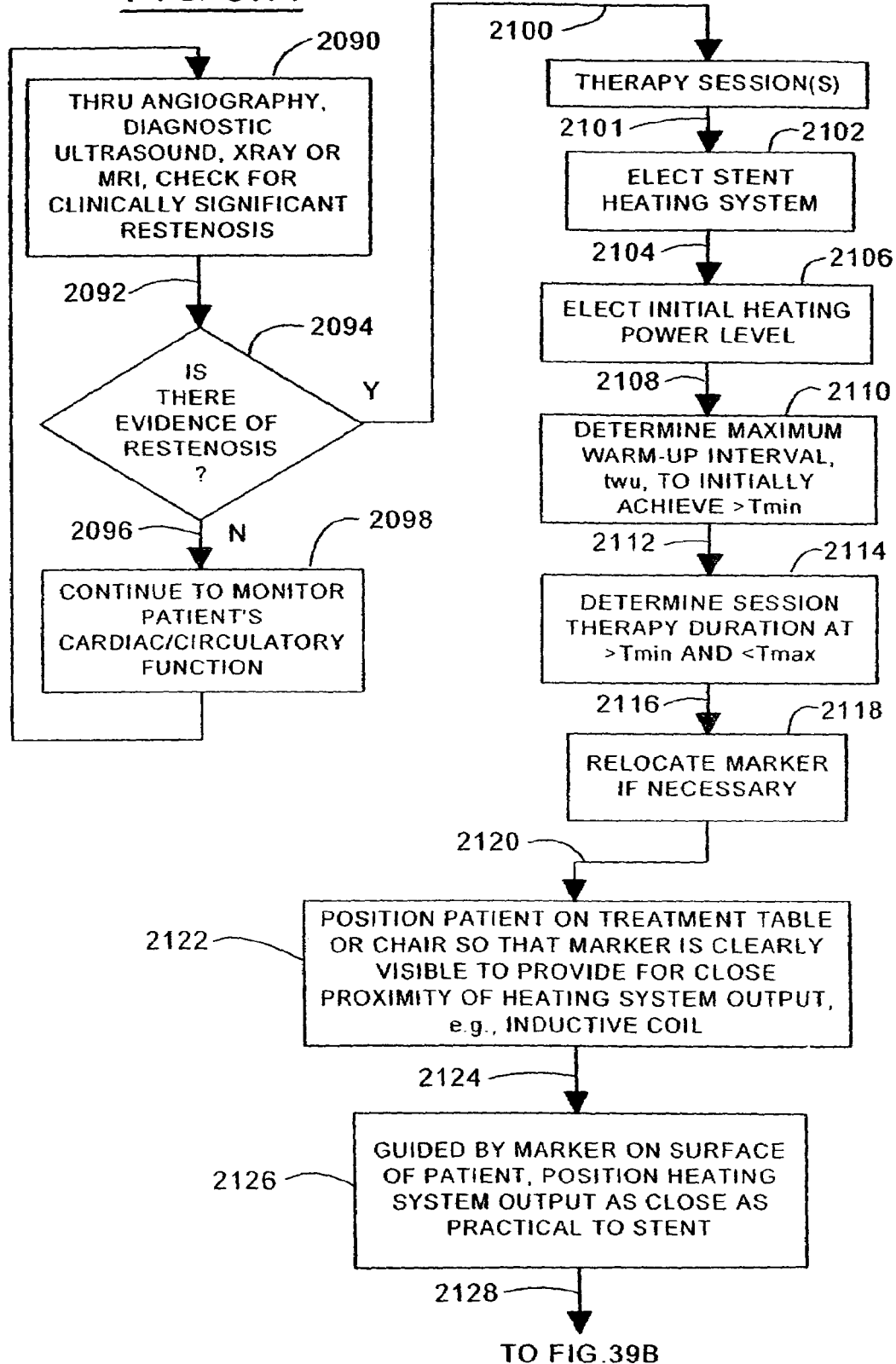

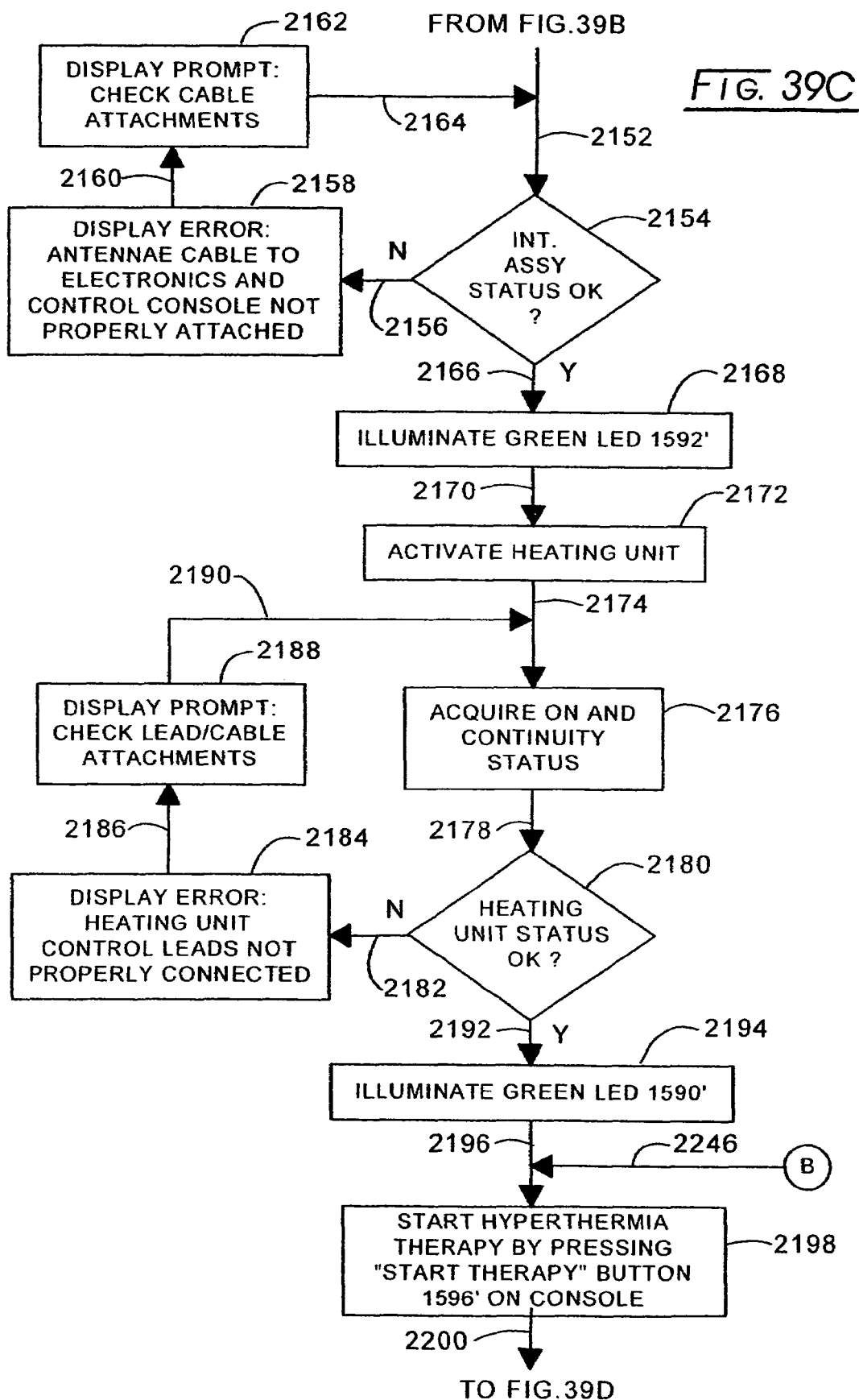

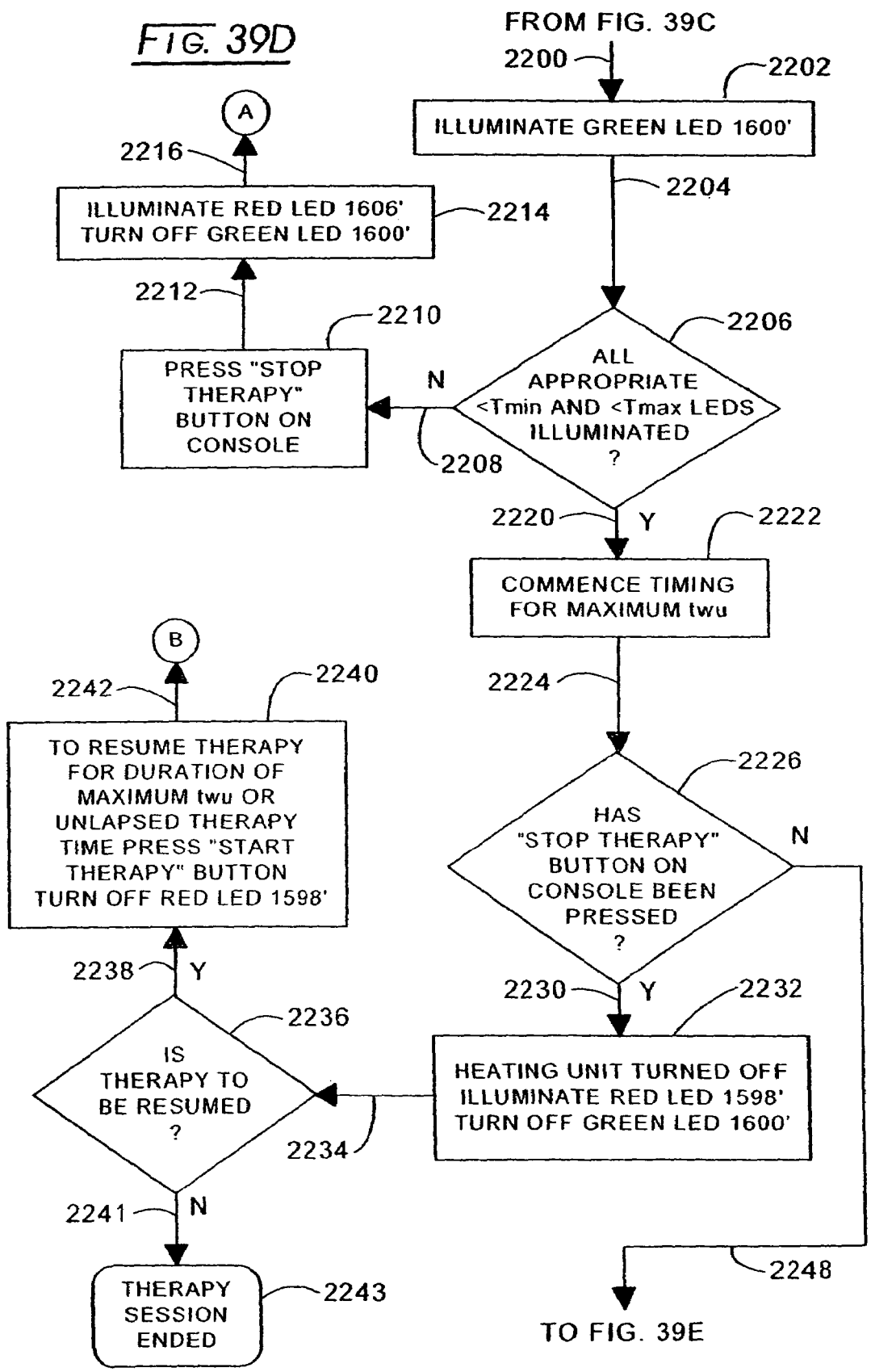

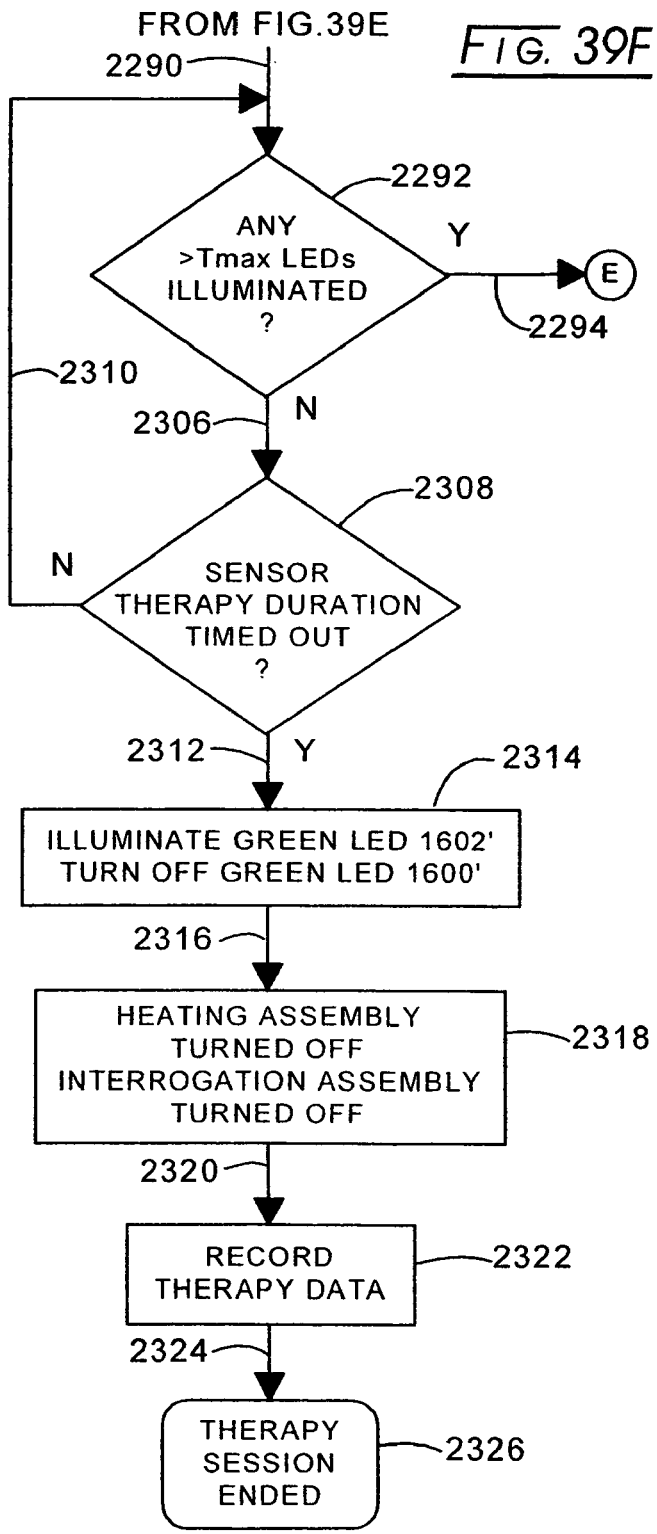
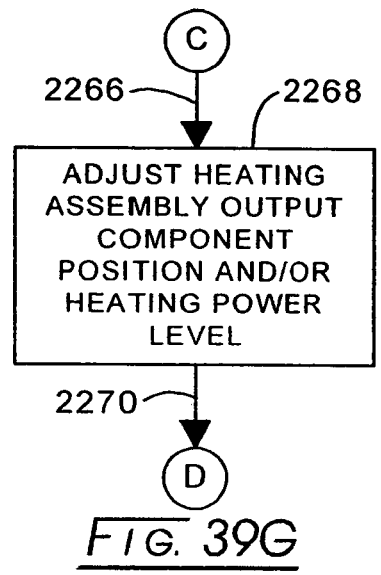
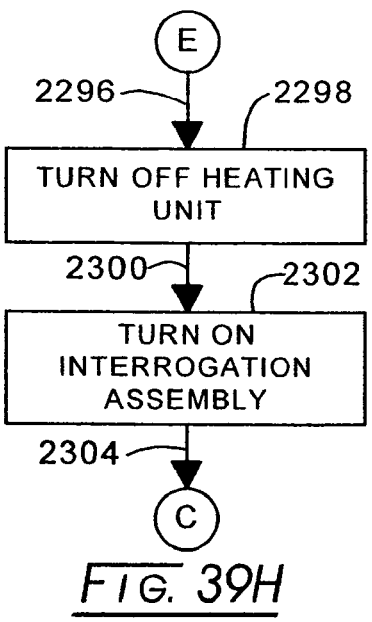

SYSTEM, METHOD AND APPARATUS FOR EVALUATING TISSUE TEMPERATURE

CROSS-REFERENCE TO RELATED APPLICATIONS

This application claims the benefit of U.S. Provisional Application No. 60/466,225, filed Apr. 28, 2003 and is a divisional of U.S. patent application Ser. No. 10/733,970, filed Dec. 11, 2003, now U.S. Pat. No. 7,048,756, which is a continuation-in-part of U.S. patent application Ser. No. 10/246,347, filed Sep. 18, 2002, now U.S. Pat. No. 6,993,394, which is a continuation of U.S. patent application Ser. No. 10/201,363 filed Jul. 23, 2002, now abandoned and claiming the benefit of U.S. Provisional Application No. 60/349,593 filed Jan. 18, 2002.

STATEMENT REGARDING FEDERALLY SPONSORED RESEARCH

Not applicable.

BACKGROUND OF THE INVENTION

A beneficial response elicited by a heating of neoplastic tissue was reported by investigators in 1971. See the following publications in this regard:
(1) Muckle, et al., "The Selective Inhibitory Effect of Hyperthermia on the Metabolism and Growth of Malignant Cells" *Brit J. of Cancer* 25:771-778 (1971).
(2) Castagna, et al., "Studies on the Inhibition by Ethionine of Aminoazo Dye Carcinogenesis in Rat Liver." *Cancer Research* 32:1960-1965 (1972).

While deemed beneficial, applications of such thermotherapy initially were constrained to external surface heating. When external applications have been employed the resultant body structure heating has been described as having been uncontrolled in thermal localization resulting in temperature elevation of the whole body. Employment of diathermy has been reported with a resultant non-destructive inhibitory reaction. In general, no consensus by investigators as to the efficacy of thermotherapy with respect to tumor was present as late as the mid 1970s. See generally:
(3) Strom, et al., "The Biochemical Mechanism of Selective Heat Sensitivity of Cancer Cells—IV. Inhibition of RNA Synthesis." *Europ. J. Cancer* 9:103-112 (1973).
(4) *Ziet. fur Naturforschung* 8, 6: 359.
(5) R. A. Holman, Letter "Hyperthermia and Cancer", *Lancet*, pp. 1027-1029 (May 3, 1975).

Notwithstanding a straightforward need for more effective techniques in the confinement of thermotherapy to localized internally located target tissue regions, investigators have established that tumor cells may be physiologically inhibited by elevating their temperatures above normal body temperature, for example, 37° C. for one major population, to a range exceeding about 40° C. The compromising but beneficial results further are predicated upon that quantum of thermal exposure achieved, based upon the time interval of controlled heat application. Thus, effective thermotherapies are characterized by an applied quantum of thermal energy established within a restrictive tissue periphery or volume of application with an accurately controlled temperature over an effective component of time.

One modality of thermotherapy is termed "hyperthermia" therapy, an approach to thermal treatment at temperatures elevated within somewhat narrow confines above normal body temperature. For instance, the elevation above a normal body temperature of 37° C. typically will fall within a range of 42° C. to 45° C. While higher temperature therapies have been described, hyperthermia therapy conventionally looks to affecting tissue to the beneficial effect of, for instance, negating neoplastic development, while avoiding denaturization, i.e., cell death or necrosis. It follows that an embracing of this therapeutic modality calls for the application of thermal control over specific tissue volumes.

Confinement of thermotherapy to a neoplasm-suspect target tissue volume internally disposed within the body without a generation of damage to healthy surrounding tissue has been considered problematic and thus the subject of diverse investigation. Experience in this field has revealed that achieving a controlled, thermo-therapeutic level of heat throughout a targeted tissue volume is difficult. In general, the distribution of induced heat across such tissue volumes can exhibit substantial variations. Vascularity and densities of heterogeneous tissues may impose such variations. For instance, the cooling properties of blood flow complicate the maintenance of a desired thermal dose at the target volume. A variety of approaches toward intra-body localized heat applications have evolved. Such efforts generally have been based upon the application of microwave energy (U.S. Pat. No. 4,138,998); the application of acoustic wave-based systems (ultrasound); the application of electric fields at RF frequencies (direct RF) from transmitting antenna arrays including an application subset utilizing inductive systems driven at relatively lower frequencies within the RF realm, and the utilization of infra red heaters.

Ultrasound is considered to be an acoustic wave above the normal range of human hearing, i.e., above about 20,000 Hertz. When employed clinically for thermo-therapeutic as well as diagnostic purposes, ultrasound system configurations perform in recognition of the acoustic impedance of investigated tissue. Acoustic impedance is the resistance to wave propagation through tissue, for example, due to absorbance, reflectance or molecularly induced scattering. Accordingly, the subject tissue volume will absorb some of the energy from the ultrasound waves propagated through it and the kinetic energy associated with the energy absorbed is converted into thermal energy to thus raise tissue temperature. See generally U.S. Pat. No. 6,451,044. When implementing ultrasound thermotherapy systems, careful control is called for to assure that minimum threshold tissue temperatures are reached and that maximum tissue temperature limits are not exceeded. Heretofore, temperature monitoring generally has been carried out by percutaneously injecting or otherwise inserting tethered temperature sensors such as thermocouples or thermistors into the targeted tissue region. Insertion of a tethered thermocouple may be accomplished by first inserting a hypodermic needle, then inserting a catheter through the needle with the sensor at its tip, whereupon the needle is withdrawn. Where hyperthermia therapy or heat induced immunotherapy are carried out, maintenance of relatively narrow temperature targets is sought, calling for a high level of control. For these thermotherapies, typically multiple therapy sessions are required, thus the generally undesirable injection or insertion of temperature sensors must be carried out for each of what may be many treatment sessions.

One approach has been advanced for ultrasound-based thermotherapy. In that approach, thermal localization is achieved by developing constructive wave interference with phased array-based wave guide applicators mounted to extend around the patient (see U.S. Pat. Nos. 5,251,645 and 4,798,215).

The microwave band generally is considered to extend from about 900 Mhz. Clinical studies have established that thermotherapy systems can be implemented with microwave radiating devices. Early endeavors utilizing microwave-based hyperthermia treatment evidenced difficulties in heating target tissue volumes at adequate depth while preventing surrounding superficial healthy tissue from incurring pain or damage due to hot spots exhibiting temperatures greater than about 44-45° C. However, later developments using adaptive phased array technology has indicated that relatively deeply located target tissues can be heated to thermotherapeutic temperatures without inducing the earlier difficulties. See generally the following publication:

(6) Fenn, et al, "*An Adaptive Microwave Phased Array For Targeted Heating Of Deep Tumors In Intact Breast: Animal Studies Results*" Int. J. Hyperthermia, Vol. 15, No. 1, pp 45-61 (1999).

Inductively-based approaches to thermotherapy systems have received important attention by investigators. The coil transmitted outputs of these systems generally are focused for field convergence toward the target tissue volume and the resultant, internally thermally affected tissue region has been monitored in situ by thermo-responsive sensors such as rod-mounted thermocouples and thermistors. Those tethered heat sensors are inserted percutaneously into the target tissue region, being coupled by extra-body electrical leads extending to connections with temperature monitoring readouts. As before, the invasiveness of the monitoring electrical leads extending into the patients' body for this procedure has been considered undesirable. This particularly holds where repetitive but time-spaced procedures are called for, or the therapeutic modality is employed in thermally treating tumor within the brain.

The radio (RF) spectrum is defined as extending from the audio range to about 300,000 MHz. However direct RF thermotherapy has been described in conjunction with the 80 MHz to 110 MHz range.

Another approach is described as performing as a focused radio frequency/microwave region system, the election between these spectral regions being determined with respect to the depth of the target tissue. See: htp://www.bsdme.com/.

Efforts to regionalize or confine therapeutic tissue heating to predefined borders or volumetric peripheries have included procedures wherein small wire or iron-containing crystals (U.S. Pat. No. 4,323,056) are implanted strategically within the tissue region of interest. Implantation is achieved with an adapted syringe instrumentality. Electromagnetic fields then are introduced to the region to inductively heat the implanted radiative-responsive heater components and thus evoke a more regionally controlled form of thermotherapy. In one such approach, ferromagnetic thermoseeds have been employed which exhibit Curie temperature values somewhat falling within the desired temperature range for an elected thermotherapy. This achieves a form of self regulation by operation of the system about those Curie transitions. For instance, as radiative inductive excitation drives the thermoseeds to temperatures to within the permeability based state change levels associated with attainment of a Curie temperature range, the thermoseeds become immune to further application of external excitation energy. (See generally U.S. Pat. No. 5,429,583). Unfortunately, the Curie transition temperature range of the thermoseeds is relatively broad with respect to the desired or target temperature. This expanded Curie transition range is, in part, the result of the presence of the ferrite-based seeds within relatively strong electromagnetic fields. The result is a somewhat broad and poor regulation temperature band which may amount 100 or more. As a consequence, the auto-regulated devices are constrained to uses inducing tissue necrosis or ablation, as opposed to uses with temperatures controlled for hyperthermia therapies. See generally:

(7) Brezovich, et al., "Practical Aspects of Ferromagnetic Thermoseed Hyperthermia." *Radiologic Clinics of North America,* 27: 589-682 (1989).

(8) Haider, et al., "Power Absorption in Ferromagnetic Implants from Radio Frequency-Magnetic Fields and the Problem of Optimization." *IEEE Transactions On Microwave Theory And Techniques,* 39: 1817-1827 (1991).

(9) Matsuki et al., "An Optimum Design Of A Soft Heating System For Local Hyperthermia" *IEEE Transactions On Magnetics,* 23(5): 2440-2442, (September 1987).

Thermotherapeutic approaches designed to avoid the subcutaneous insertion of one or more temperature sensors have looked to the control of heating using modeling methodology. These approximating modeling methods are subject to substantial error due to differences or vagaries exhibited by the heterogeneous tissue of any given patient. Such differences may be due to variations in vascularity, as well as the gradual metamorphosis of a tumor mass. The latter aspect may involve somewhat pronounced variations in tissue physiologic characteristics such as density. See generally the following publication:

(10) Arkin, H. et al., "Recent Development In Modeling Heat Transfer in Blood Perfused Tissue." *IEEE Transactions on Bio-Medical Engineering,* 41 (2): 97-107 (1994).

Some aspects of thermotherapy have been employed as an adjunct to the use of chemotherapeutic agents in the treatment of tumor. Because of the precarious blood supply or vascularity and of the high interstitial fluid presence, such agents may not be effectively delivered to achieve a 100% cell necrosis. Further the tumor vessel wall may pose a barrier to such agents, and resultant non-specific delivery may lead to significant systemic toxicities. Studies have addressed these aspects of chemotherapy, for instance, by the utilization of liposomes to encapsulate the chemotherapeutic agents to achieve preferential delivery to the tumor. However the efficiencies of such delivery approaches have been somewhat modest. Clinically, hyperthermia therapy has been employed as a form of adjunct therapy to improve the efficiency of more conventional modalities such as radiation therapy and chemotherapy. For the latter applications the thermal aspect has been used to augment bloodstream borne release agents or liposome introduction to the tumor site. Hyperthermia approaches have been shown to trigger agent release from certain liposomes, making it possible to release liposome contents at a heated site (U.S. Pat. Nos. 5,490,840; 5,810,888). For any such thermotherapeutic application, an accurate temperature control at the situs of the release is mandated. See the following publications:

(11) Kong, et al., "Efficacy of Lipsomes and Hyperthermia in a Human Tumor Xenograft Model: Importance of Triggered Drug Release." *Cancer Research,* 60: 6950-6957 (2000).

(12) Chung, J. E., et al., "Thermo-Responsive Drug Delivery From Polymeric Micelles Using Block Co-Polymers of Poly (N-isopropylacrylamide-b-butylmethacrylate) and Poly (butylmethacrylate), *Journal of Controlled Release* (Netherlands), 62(2): 115-127 (Nov. 1, 1999).

Hyperthermia when used in conjunction with radiation treatment of malignant disease has been demonstrated as beneficial for destroying a specific tumor site. Clinical data has evolved demonstrating an improved efficacy associated with combined radiation and hyperthermia treatments as compared to radiation therapy alone. Such multimodal therapy concepts also have been extended to a combination of hyperthermia treatment with both radiation treatment and chemotherapy (radiochemotherapy). See generally:

(13) Falk et al., "Hyperthermia In Oncology" *Int. J. Hyperthermia,* 17: 1-18 (2001).

Biological mechanisms at the levels of single cells activated by heat became the subject of scientific interest in the early 1960s as consequence of the apparently inadvertent temperature elevation of an incubator containing *Drosophila melanogaster* (fruit flies). These creatures, upon being heat shocked, showed the characteristic puffs indicative of transcriptional activity and discrete loci. See the following publication:

(14) Ritossa, "A New Puffing Pattern Induced By Temperature Shock and DNP in Drosophila." *Experientia,* 18: 571-573 (1962).

These heat shock loci encoding the heat shock proteins (HSPs), became models for the study of transcriptional regulation, stress response and evolution. The expression of HSPs may not only be induced by heat shock, but also by other mechanisms such as glucose deprivation and stress. Early recognized attributes of heat shock proteins resided in their reaction to physiologically support or reinvigorate heat damaged tissue. (See U.S. Pat. No. 5,197,940). Perforce, this would appear to militate against the basic function of thermotherapy when used to carry out the denaturization of neoplastic tissue. However, heat shock phenomena exhibit a beneficial attribute where the thermal aspects of their application can be adequately controlled. In this regard, evidence that HSPs, possess unique properties that permit their use in generating specific immune responses against cancers and infectious agents has been uncovered. Additionally, such properties have been subjects of investigation with respect to boney tissue repair, transplants and other therapies. See generally the following publications:

(15) Anderson et al., "Heat, Heat Shock, Heat Shock Protein and Death: A Central Link in Innate and Adoptive Immune Responses." *Immunology Letters,* 74: 35-39 (2000).

(16) Srivastava, et al, "Heat Shock Proteins Come of Age: Primitive Functions Acquire New Role In an Adaptive World." *Immunity,* 8(6): 657-665 (1998).

Beneficial thermal compromization of target tissue volumes is not entirely associated with HSP based treatments for neoplastic tissue and other applications, for instance, having been studied in connection with certain aspects of angioplasty. Catheter-based angioplasty was first intentionally employed in 1964 for providing a transluminal dilation of a stenosis of an adductor hiatus with vascular disease. Balloon angioplasty of peripheral arteries followed with cautious approaches to its implementation to the dilation of stenotic segments of coronary arteries. By 1977 the first successful percutaneous transluminal coronary angioplasty (PTCA) was carried out. While, at the time, representing a highly promising approach to the treatment of angina pectoris, subsequent experience uncovered post-procedural complications. While PTCA had been observed to be effective in 90% or more of the subject procedures, acute reclosure, was observed to occur in approximately 5% of the patients. Stenosis was observed to occur in some patients within a period of a few weeks of the dilational procedure and restenosis was observed to occur in 15% to 43% of cases within six months of angioplasty. See generally:

(17) Kaplan, et al., "Healing After Arterial Dilatation with Radiofrequency Thermal and Non-Thermal Balloon Angioplasty Systems." *Journal of Investigative Surgery,* 6: 33-52 (1993).

In general, the remedy for immediate luminal collapse has been a resort to urgent or emergency coronary bypass graft surgery. Thus, the original procedural benefits attributed to PTCA were offset by the need to provide contemporaneous standby operating room facilities and surgical personnel. A variety of modalities have been introduced to avoid post PTCA collapse, including heated balloon-based therapy, (Kaplan, et al., supra) the most predominate being the placement of a stent extending intra-luminally across the dilational situs. Such stents currently are used in approximately 80% to 90% of all interventional cardiology procedures. While effective to maintain or stabilize intra-luminal dilation against the need for emergency bypass procedures, the stents are subject to the subsequent development of in-stent stenosis or restenosis (ISR). See generally:

(18) Holmes, Jr., "In-Stent Restenosis." *Reviews in Cardiovascular Medicine,* 2: 115-119 (2001).

Debulking of the stenotic buildup has been evaluated using laser technology; rotational atherectomy; directional coronary atherectomy; dualistic stent interaction (U.S. Pat. No. 6,165,209); repeated balloon implemented dilation, the application of catheter introduced heat to the stent region (U.S. Pat. No. 6,319,251); the catheter-borne delivery of soft x-rays to the treated segment, sonotherapy; light activation; local arterial wall alcohol injection; and ultrasound heating of a stent formed of an ultrasound absorptive material (U.S. Pat. No. 6,451,044).

See additionally the following publications with respect to atherectomy for therapeutically confronting restenosis:

(19) Bowerman, et al., "Disruption of Coronary Stent During Artherectomy for Restenosis." *Catherization and Cardiovascular Diagnosis,* 24: 248-251 (1991).

(20) Meyer, et al., "Stent Wire Cutting During Coronary Directional Atherectomy." *Clin. Cardiol.* 16: 450-452 (1993).

In each such approach, additional percutaneous intervention is called for. See generally the following publication:

(21) Vliestra and Holmes, Jr., *Percutaneous Transluminal Coronary Angioplasty* Philadelphia: F. A. Davis Co. (Mayo Foundation) (1987).

Other approaches have been proposed including the application of electrical lead introduced electrical or RF applied energy to metallic stents, (U.S. Pat. No. 5,078,736); the incorporation of radioisotopes with the stents (U.S. Pat. Nos. 6,187,037; 6,192,095); and resort to drug releasing stents (U.S. Pat. No. 6,206,916 B1). While non-invasive control of ISR has been the subject of continued study, the development of a necessarily precise non-invasively derived control over it has remained an elusive goal.

Another application of hyperthermia is in orthopedics, as a means to stimulate bone growth and fracture healing. There are several FDA approved devices for stimulation of bone growth or healing, each with limitations and side effects. Therapies include invasive electrical stimulation, electromagnetic fields, and ultrasound stimulation. Decades old research has claimed a stimulation of bone growth by a mild increase in temperature of the boney tissue. Previous researchers have used such methods as inductive heating of implanted metal plates, or heating coils wrapped around the bone. The utility of these methods is limited by the invasive nature of the surgery needed to implant the heating elements and the inability to closely control tissue temperature. More-over, therapeutic benefits have been inconsistent between different studies and experimental protocols. For a summary of past work, see generally:

(22) Wootton, R. Jennings, P., King-Underwood, C., and Wood, S. J., "The Effect of Intermittent local Heating on Fracture Healing in the Distal Tibia of the Rabbit." *International Orthopedics*, 14: 189-193 (1990).

A number of protocols have demonstrated a beneficial effect of hyperthermia on bone healing. Several studies indicate temperature affects bone growth and remodeling after injury. Hyperthermia may both improve blood supply and stimulate bone metabolism and have a direct effect on bone-forming cells by inducing heat shock proteins or other cellular proteins. In one experiment, rabbit femurs were injured by drilling and insertion of a catheter. Hyperthermia treatments were given at four-day intervals for 2-3 weeks using focused microwave radiation. Bones which had suffered an insult as a result of the experimental procedure showed a greater density of osteocytes and increased bone mass when treated with hyperthermia. Injured bones treated with hyperthermia showed completely ossified calluses after two weeks, while these processes normally take four weeks in untreated injuries. One problem with microwave heating of bone mass is the difficulty in predicting heat distribution patterns and maintaining the target tissue within the appropriate heat range.

When tissue is heated at too high of temperature, there can be irreversible cytotoxic effects which could damage bone and other tissues, including osteogenic cells, rather than induce healing. Certain studies have shown that induction of mild heat shock promotes bone growth, while more severe heat shock inhibits bone growth. Therefore, control and monitoring of the temperature of the targeted bone tissue is imperative to achieve therapeutic benefit and avoid tissue damage.

See additionally the following publications with respect to hyperthermia for therapeutically promoting osteogenesis:

(23) Leon, et al., "Effects of Hyperthermia on Bone. II. Heating of Bone in vivo and Stimulation of Bone Growth." *Int. J. Hyperthermia* 9: 77-87 (1993).

(24) Shui et al., "Mild heat Shock Induces Proliferation, Alkaline Phosphatase Activity, and Mineralization in Human Bone Marrow Stromal Cells and Mg-63 Cells In Vitro." *Journal of Bone and Mineral Research* 16: 731-741 (2001).

(25) Huang, C.-C., Chang, W. H., and Liu, H.-C. "Study on the Mechanism of Enhancing Callus Formation of Fracture by Ultrasonic Stimulation and Microwave Hyperthermia." *Biomed. Eng. Appl. Basis Comm.* 10: 14-17 (1998).

Existing protocols for therapeutically promoting osteogenesis are limited by the invasive nature and concomitant potential for infection for instance with tethered electrical stimulators; poor temperature control, and potential for tissue injury or reduced therapeutic benefit, for instance with microwave heating or other induced electromagnetic fields; difficulty in effectively applying therapy to the injured bone because of targeting difficulties or low patient compliance with prescribed repetitive therapy.

The host immune system can be activated against infectious disease by heat shock protein chaperoned peptides in a manner similar to the effect seen against metastatic tumors. Heat shock proteins chaperoning peptides derived from both viral and bacterial pathogens have been shown to be effective at creating immunity against the infectious agent. For infectious agents for which efficacious vaccines are not currently available (especially for intracellular pathogens e.g. viruses, *Mycobacterium tuberculosis* or Plasmodium) HSP chaperoned peptides may be useful for the development of novel vaccines. It is expected that purified HSP chaperoned peptides (e.g. gp96 complexes) used as vaccines for diseases caused by highly polymorphic infectious agents would be less effective against genetically distinct pathogen populations. For a summary of past work on HSP vaccines against infectious agents, see generally:

(26) Neiland, Thomas J. F., M. C. Agnes A. Tan, Monique Monnee-van Muijen, Frits Koning, Ada M. Kruisbeek, and Grada M. van Bleek, "Isolation of an immunodonminant viral peptide that is endogenously bound to stress protein gp96/GRP94. "*Proc. Nat'l Acad. Sci. USA,* 93: 6135-6139 (1996).

(27) Heikema, A., Agsteribbe, E., Wilschut, J., Huckriede, A., "Generation of heat shock protein-based vaccines by intracellular loading of gp96 with antigenic peptides." *Immunology Letters,* 57: 69-74 (1997).

(28) Zugel, U., Sponaas, A. M., Neckermann, J., Schoel, B., and Kaufmann, S. H. E., "gp96-Peptide Vaccination of Mice Against Intracellular Bacteria." *Infection and Immunity,* 69: 4164-4167 (2001).

(29) Zugel, U., and Kaufmann, S. H. E., "Role of Heat Shock Proteins in Protection from and Pathogenesis of Infectious Diseases." *Clinical Microbiology Reviews,* 12: 19-39 (1999).

In commonly owned co-pending application for U.S. patent Ser. No. 10/246,347, filed Sep. 18, 2002 and entitled "System, Method and Apparatus for Localized Heating of Tissue", an approach to accurately carrying out an in situ elevation of the temperature of a target tissue volume is presented. Accuracy is achieved using untethered temperature sensor implants formed of ferromagnetic material which experiences an abrupt magnetic permeability state change within a very narrow temperature range. Temperature sensing is carried out by monitoring a very low level magnetic field extending through the position of the implant. For instance, the earth's magnetic field may be employed. Where inductively based heating is utilized, non-magnetic heaters may be implanted with the sensors and sensing is carried out intermittently in the absence of the inductably derived magnetic field.

BRIEF SUMMARY OF THE INVENTION

The present invention is addressed to method, system and apparatus for accurately evaluating a temperature related physical parameter within the body of a patient. Accurate temperature measurement is achieved through the use of one or more tetherless temperature sensors strategically located within the body and configured with a passive resonant circuit. These passive circuits respond to an extra body applied excitation electromagnetic field by resonating at an identifiable unique resonant center frequency. In one embodiment, the resonant circuit based sensors are configured with a capacitor and a series coupled inductor formed with a winding disposed about a ferrite core. That ferrite core is formulated to exhibit a somewhat sharp permeability state change or transition at a Curie temperature corresponding with a desired temperature setpoint. With the arrangement, upon being excited by an applied excitation burst, the sensor will ring or resonate at its unique, signature resonant center frequency when at monitor temperatures below the involved Curie temperature. As the sensor witnesses monitoring temperatures approaching the Curie temperature defined setpoint the intensity of its unique resonant center frequency decreases, an aspect which may be taken advantage of from a temperature control standpoint. However, when the Curie or target temperature is reached, the relative permeability of the sensor's ferrite core drops sharply toward a unity value to, in turn, cause a sharp drop in the reluctance of the associated inductor coil causing the resonant frequency of the device to shift substantially upward in value. This shift is to an off-scale value. In effect, the signature output disappears. As the sensors resonate in response to excitation, the detector components of the associated interrogation system are capable of sensing all of the resonating devices, whereupon the sensed signals are digitized, averaged and analyzed to identify each sensor by its unique resonant center frequency, if at the noted monitor temperatures. Such analysis may be carried out using a Fourier transform-type approach. Because the unique resonant center frequency remains stable as the temperatures witnessed by the sensors, approach or transition toward the Curie temperature-based setpoint, the amplitude of the Fourier transform signal will diminish and the system has the capability of predicting the arrival of the Curie based setpoint temperature. Thermal overshoot can thus be more accurately accommodated for.

The unique resonant center frequencies of the sensors are readily established by adjusting the value of inductance and/or capacitance of the passive resonant circuits. In general, the unique resonant center frequencies are developed within a frequency band ranging from about 100 kHz to about 2 MHz. Accordingly, a substantial range of sensor signatures are available to the system.

A feature of the system and method of the invention is concerned with a typical patient management regimen wherein a relatively substantial repetition of thermotherapeutic procedures is called for. The sensors remain in position with respect to the target tissue volume and may, in this regard, be fashioned with anchors for the purpose of migration avoidance. Where a succession of treatments is involved, not only is there no requirement to re-install sensors, but also, the alignment of excitation and sensing antennae as well as heating unit output orientations essentially are simply repeated. Another aspect of this feature resides in the utilization of the pre-implanted sensors as a conventional tumor situs marker for subsequent patient evaluation imaging procedures.

In one embodiment of the invention one or more of the sensor implants are configured to exhibit Curie transitions at a lower threshold setpoint temperature, while an additional one or more are configured to exhibit Curie transitions at an upper limit higher setpoint temperature. Thus, the practitioner will be apprised of the target tissue volume reaching that minimum temperature adequately for therapy, as well as of any temperature excursions above the upper limit. Where such thermal excursions occur, the heating unit involved may be adjusted, for example, in terms of power level as well as component positioning.

Those sensor implants configured to identify attainment of a lower threshold temperature setpoint may be combined with ferrite core implemented auto-regulating heater implants having Curie transitions at an upper limit higher temperature setpoint. This particular combination will be beneficial where the thermotherapy temperature levels involved will approach apoptosis or necrosis levels, as well as for the previously mentioned hyperthermia therapy administered in the range between approximately 40° C. and 45° C.

The instant method has broad application to thermotherapy endeavors including an in vivo induction of heat shock proteins, a procedure having important utility in the treatment of cancer, infectious diseases and other therapies. As another modality, one or more of the sensors is combined with an intra-luminal stent and when so combined and implanted, permit a non-invasive repeatable and accurate hyperthermia therapy for stenosis/restenosis.

The implant control heating approach of the invention also may be applied to the field of orthopedics. In this regard, the sensor components may be combined in intimate thermal exchange relationship with non-magnetic metal bone support devices implanted with bony tissue. The setpoint temperature elected for such modality is selected to enhance the repair of the mending bony tissue.

Implant based controlled in vivo heating according to the precepts of the invention also may be employed as a vehicle for inducing immunity against or for the treatment of diseases cause by infectious agents.

Other objects of the invention will, in part, be obvious and will, in part appear hereinafter.

The invention, accordingly, comprises the method, system and apparatus possessing the construction, combination of elements, arrangement of parts and steps which are exemplified in the following detailed description.

For a fuller understanding of the nature and objects of the invention, reference should be made to the following detailed description taken in connection with the accompanying drawings.

BRIEF DESCRIPTION OF THE DRAWINGS

FIGS. 12A-12D are electrical schematic diagrams showing a detector circuit employed with the system of the invention;

FIG. 13 illustrates a block diagram of the interrogation system of the invention;

FIG. 14 is a perspective view of a sensor according to the invention;

FIG. 14A is a sectional view of the sensor shown in FIG. 14 taken through the plane 14A-14A shown in FIG. 14B;

FIG. 14B is an end view of the sensor of FIG. 14A;

FIG. 14C is a top view of the sensor of FIG. 14A with components shown in phantom;

FIG. 15 is a perspective view of an auto-regulating heater implant;

FIG. 15A is a sectional view of the auto-regulating implant shown in FIG. 15;

FIG. 15B is an end view of the implant of FIG. 15A;

FIGS. 21A-21G combine as labeled thereon to provide a flowchart illustrating a procedure and control carried out with the system of FIG. 19;

FIGS. 23A-23H combine as labeled thereon to provide a flowchart illustrating another intermittent procedure and control carried out with the system represented in FIG. 19;

FIGS. 24A-24G combine as labeled thereon to provide a flowchart illustrating an intermittent procedure and control employing both sensors and auto-regulating heaters as carried out with the system represented in FIG. 19;

FIGS. 26A-26J combine as labeled thereon to provide a flowchart illustrating the procedures and control carried out with the system represented in FIG. 25;

FIGS. 38A-38B combine as labeled thereon to illustrate an initial stent implantation procedure;

FIGS. 39A-39H combine as labeled thereon to provide a flowchart illustrating the procedure and control carried out within the system represented in FIG. 37;

DETAILED DESCRIPTION OF THE INVENTION

Figure 1:
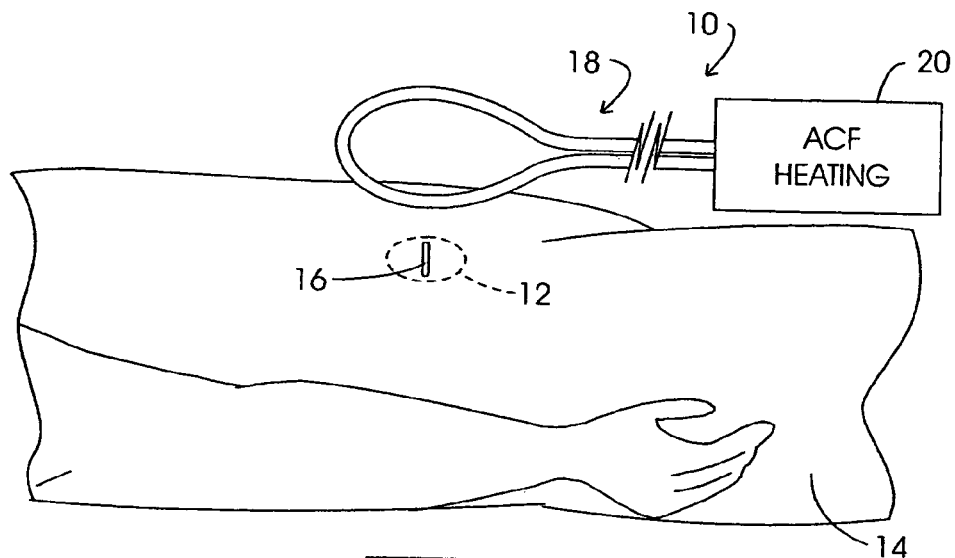
FIG. 1 is a partial schematic view of a prior art approach to heating a target tissue volume utilizing an auto-regulating heater implant.

While a variety of techniques for evolving an effective interstitial thermotherapy of target tissue volumes have been approached by investigators, an earlier development deemed somewhat promising involved the implantation of ferromagnetic alloy heaters sometimes referred to as "ferromagnetic seeds" within that volume. The ferromagnetic alloy heaters were adapted so as to alter in exhibited magnetic permeability in consequence of temperature. For example, with this arrangement, when a Curie temperature transition range was thermally reached, permeability would, in turn, diminish over the transition range and correspondingly thermal responsiveness to an applied inductive field would diminish. Thus it was opined that a temperature auto-regulation could be achieved to optimize a thermally based implantation therapy. Such an arrangement is depicted in FIG. 1. Here, the treatment modality is represented generally at 10 wherein a target tissue volume, for example, comprised of neoplastic tissue, is shown symbolically within dashed region 12 located internally within the body of patient 14. Within the target tissue volume 12 a ferromagnetic material (e.g., ferromagnetic alloy comprising primarily palladium and cobalt) auto-regulating heater implant 16 is embedded which is, for instance, inductively heated from the excited inductive coil 18 of an alternating current field (ACF) heating assembly 20. The ferromagnetic implants as at 16 exhibit a temperature-related relative magnetic permeability, $\mu_r$. Such relative permeability may be represented by curve 22 shown in FIG. 2. Relative permeability is expressed as $\mu_r = \mu/\mu_o$, where $\mu$=absolute permeability (Henry/meter), $\mu_o$=a constant=magnetic permeability of free space (Henry/meter) and $\mu_r$ is therefore dimensionless but ranges from a value of unity to 100,000 or more. Curve 22 reveals that the relative magnetic permeability, $\mu_r$, decreases as the temperature of the ferromagnetic alloy heater approaches its Curie temperature, $T_c$. Since the induced electric field heating power in an object is proportional to the square root of magnetic permeability, a decrease in magnetic permeability with elevation of temperature is associated with a corresponding decrease in the heating power associated with inductive heating.

Traditionally, the change in magnetic permeability of ferromagnetic alloys with increasing temperature has not been abrupt as would be preferred for precise temperature regulation of an implanted heating component as at 16. In this regard, characteristic curve 22 reveals that under the relatively intense, applied fields a permeability transition occurs gradually over a span typically of 10° C. to 15° C. or more. Responses of ferromagnetic-based auto-regulators as represented at curve 22 are occasioned both by the formulation of the ferromagnetic material as well as its reaction to the imposed inductive field which is somewhat unavoidable for auto-regulation. As a result, the implanted heater device 16 may not reach the intended Curie temperature and resultant relative permeability of unity. Often, that elevation in temperature above normal body temperature has not been achieved. Accordingly, accommodation has been made by electing Curie temperature transition ranges falling well above what would have otherwise been a target temperature for thermotherapy with a result that critical temperature limits of the tissue being treated have been exceeded. Because of such performance, thermotherapy utilizing such auto-regulating heating implants has been constrained to developing higher temperatures including those deriving necrosis or cell death. Thermotherapeutic procedures also are prone to inaccuracies by virtue of the unknown environmental conditions within which an implant as at 16 is situated. With respect to such unknown phenomena, temperatures achieved with ferromagnetic implants will vary depending upon cooling phenomena within the tissue surrounding the device. Such phenomena occur, for example, as a consequence of the degree of vascularity in the target region and proximity of the heating element as at 16 to blood vessels. These vessels will tend to perform as inherent cooling mechanisms. Accordingly, while attempting to achieve an effective heat therapy, the auto-regulating implants as at 16 generally have been unable to establish a necessary precise temperature output for requisite therapeutic time intervals.

Now turning to the subject of the physiological consequence of elevating tissue temperature, studies have been carried out to investigate both the component of temperature elevation as well as the time component within which such asserted higher temperatures are maintained, i.e., the temporal aspect thereof.

(30) See: Niemz, M. H., "Laser-Tissue Interactions: Fundamentals and Applications", $2^{nd}$ Edition, Springer, Berlin, G E (2002) p.78.

Figure 3:
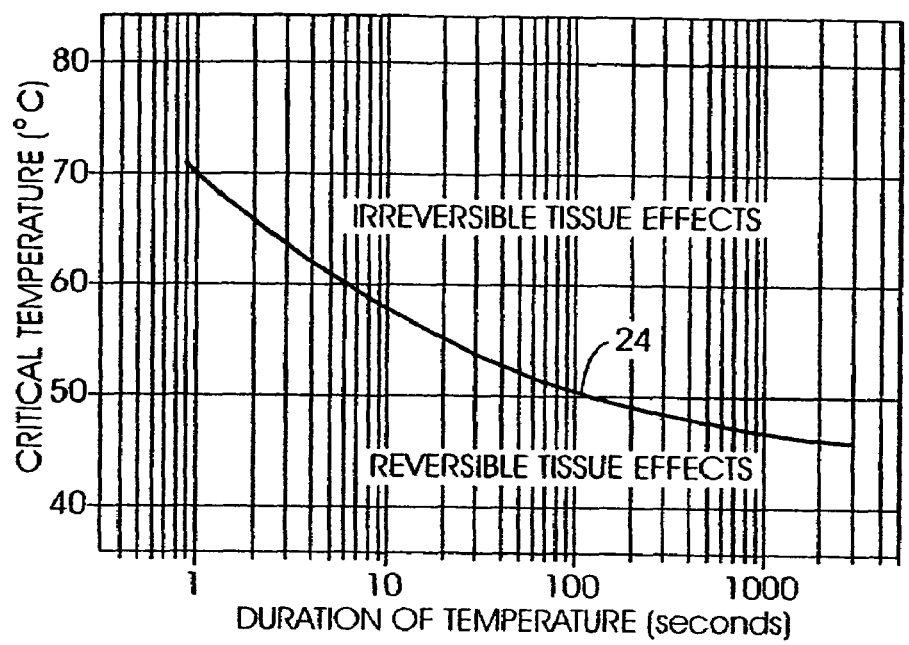
FIG. 3 is a generalized semi-log curve illustrating the temporal relationship between the duration of application of a given temperature to tissue with the value of critical temperatures.

Such investigations have established critical temperature and time relationships which identify the occurrence of irreversible tissue damage effects. In this regard, looking to FIG. 3, a generalized semi-log curve 24 is presented illustrating the temporal relationship between the duration of the application of a given temperature to tissue with the value of that critical temperature at which irreversible tissue damage may occur. The system and method of the present invention are concerned, inter alia, with maintaining the treatment of target tissue volumes at accurately controlled temperatures for all heat-based therapies including hyperthermia. Hyperthermia is a form of thermotherapy where there is an artificial elevation of the temperature of a group of cells, a tissue, cell culture, or a whole organism for experimental or therapeutic purposes. Heating of tissue through thermotherapy techniques can induce a variety of biologic responses, depending on the intensity of the stress induced. When a tissue is heated, certain cells near the focus of the induced heating may experience greater heat shock than cells at a distance from the focus. Therefore, within a tissue being heated, a range of responses may occur at the cellular level. These responses of tissues to hyperthermia can be broadly categorized. If the heat shock is too mild, there will be no detectable biologic changes (over the basal level of "heat shock" gene expression typical in the absence of heat shock). A mild heat shock may induce reversible cellular changes, including, for example, reversible denaturation of proteins, triggering of ion fluxes from various cellular compartments, activation of existing enzymes, and importantly, induction of alterations in gene expression.

A more severe heat shock may irreversibly damage cellular components. Under certain conditions, when a cell is damaged, an ordered process, apoptosis, is induced that leads to the death of the damaged cell. Apoptosis is considered a form of "programmed cell death," and cells undergoing apoptosis often exhibit distinctive morphologic changes. Apoptosis is also involved in many developmental processes, defensive responses to microbial infection, the homeostasis of cell populations (e.g. lymphocytes) and as means of eliminating genetically damaged cells, such as cancer cells.

It is generally accepted that apoptosis is an active, highly organized, form of cell death, requiring both RNA and protein synthesis. A classic example is the systematic death of a finite number of cells, 131, at a certain stage in the life cycle of the nematode *Caenorhabditis elegans*, a process controlled by the negative and positive regulation of specific genes. As demonstrated by development in *C. elegans*, certain genes are involved in the regulation of cell death by apoptosis. A specific example is the human gene bcl-2. In certain human follicular B-cell lymphomas, deregulation of the expression of bcl-2 has been identified as a cause of the prolonged survival of the lymphoma cells. Altered expression of bcl-2 interferes with the typical programmed cell death pattern, blocking apoptosis even when hematopoeitic growth factors are absent.

Apoptotic cells exhibit a pronounced decrease in cellular volume, modification of the cytoskeleton that results in convolution of the cell, and eventual blebbing of the cell's membrane, compaction of chromatin and its segregation within the nucleus of the cell. The DNA is degraded into small fragments, and the apoptotic cell sheds small membrane-bound apoptotic bodies which may contain intact organelles. The apoptotic bodies are phagocytosed (e.g. by macrophages) and the contents of apoptotic bodies are intracellularly degraded, with little release of the contents of the apoptotic cells. In this manner, apoptosis does not induce a localized inflammatory response.

Apoptosis is differentiated from necrosis by the general absence of inflammation. It is a physiological type of cell death, part of a homeostatic mechanism to maintain an optimal number and arrangement of cells. In certain physiological conditions, massive apoptosis is not followed by necrosis and inflammation, such as the removal of interdigital webs during early human development, the regression of liver hyperplasia following withdrawal of a primary mitogen and cellular loss in the premenstrual endometrium.

Where thermotherapy is sufficiently severe, cells and tissues are so damaged that cellular integrity is destroyed, or the cellular machinery is so disabled that the induction of apoptosis does not occur. In contrast to apoptosis, necrosis is a type of cell death morphologically characterized by extensive cell loss, which results in the recruitment of inflammatory cells. In necrosis, injured cells may exhibit clumping of chromatin, swelling of the cell and organelles (demonstrating a loss of control of ion balance), flocculent mitochondria, and eventual bursting and disintegration of the necrotic cell. If necrosis is extensive enough, the architecture of a tissue is destroyed. Extensive necrosis is characteristic of tissue destruction induced following severe damage by toxic chemicals, invasive microorganisms or ischemia. The wholesale release of cellular components into a tissue itself can trigger a damaging inflammatory response.

When a tissue is damaged, cells may die by a combination of apoptosis and necrosis. Many agents capable of inducing necrosis also induce apoptosis. Apoptosis often precedes extensive necrosis, with apoptosis in these situations possibly acting in a self-protective manner. When the level of insult to a tissue is too great, necrotic cell death cannot be avoided. Murine mastocytoma cells have been reported to undergo apoptosis after a moderately severe heat shock, but the same cells die via necrosis when the heat shock exposure is more severe.

For a comparison of apoptosis and necrosis, see:
(31) Columbano, A., "Cell Death: Current Difficulties in Discriminating Apoptosis from Necrosis in Context of Pathological Processes in vivo." *Journal of Cellular Biochemistry*, 58: 181-190 (1995).

The cellular response to a heat shock has been extensively studied. Certain heat shock inducible proteins such as Heat Shock Protein 70 (HSP70), HSP 90 and gp96 are expressed constitutively at low levels. During mild to moderate heat shock, cellular proteins may undergo conformational changes. It is this alteration in the structure of proteins, or other reversible denaturation effects, which are believed to play a role in inducing the heat shock response. (Note that other stressors, such as nutrient deprivation, release of oxygen radicals, or viral infection may also induce conformational aberrations.) Following a heat shock, mRNA expression of the genes encoding HSP70, HSP 90 and gp96, for example (along with that of other heatshock responsive genes) is induced by activating proteins called "Heat Shock Factors." The response of two "Heat Shock Factors", HSF-I and HSF-II is triggered by different levels of thermal stress. As an example, HSP70 is thought to be induced more rapidly than (by either less heat stress, or a shorter duration) HSP90. Therefore, different thermotherapy regimes will induce different panels of heat inducible genes.

For additional background on the heat shock response see:
(32) Georgopoulos, C., Welch, W. J. "Role of the Major Heat Shock Proteins as Molecular Chaperones." *Annu. Rev. of Cell Biol.*, 9: 601-634 (1993).
(33) Hendrick, J. P. and Hartl, F. U., "Molecular Chaperone Functions of Heat-Shock Proteins." *Annu. Rev. of Biochem.*, 62: 349-84 (1993).
(34) Lindquist, S., "The Heat Shock Response." *Annu. Rev. Biochem.*, 55: 1151-91 (1986).
(35) Matzinger, "Tolerance and Danger: the Sensitivity of the Immune System." *Annu. Rev. Immunol.*, 12: 991-1044 (1994).
(36) Morimoto R. I., "Perspective: Cells in Stress: Transcriptional Activation of Heat Shock Genes." *Science* 259: 1409-10 (1993).
(37) Morimoto, R. I., et al., "The transcriptional regulation of heat shock genes: A plethora of heat shock factors and regulatory conditions." in *Stress Inducible Responses*, ed. by Feige et al., Springer Verlag, Boston pp. 120, 139-163 (1996).
(38) Parsell, D. A. & Lindquist, S., "The Function of Heat-Shock Proteins in Stress Tolerance: Degradation and Reactivation of Damaged Proteins." *Annu. Rev. of Genet.*, 27: 437-496 (1993).
(39) Schlesinger, M. J., "Minireview: Heat Shock Proteins." *Journal of Biological Chemistry* 265: 12111-12114 (1990).

Initiation of a heatshock will induce conformational changes in cellular proteins, and lead to the induction of heat shock genes. HSP70 has the ability to bind to proteins, is thought to act as a molecular chaperone, and may use an ATP dependant activity to renature stress-damaged proteins. It is thought that HSP 70 is involved in a process that 'repairs' partially denatured proteins. If the native conformation of a protein is not restored, then the denatured protein is degraded. During the degradation process, HSP70 can retain a peptide fragment derived from the degraded protein. In essence HSP 70 may then chaperone an antigenic peptide fragment of the denatured protein. These HSP70 chaperoned fragments are then processed though the cell's endoplasmic reticulum and Golgi apparatus, and can then appear on the cell surface, presented by MHC-I molecules. Antigens presented on the surface of a cell can then lead to an immune response being generated to those antigens.

In order to have processing of peptide fragments, and presentment of potentially immunogenic fragments on the cell surface, it is necessary to have a living cell. An apoptotic cell, since the cellular contents are degraded (for instance, without presenting antigens on the phagocytitic cell's surface MHC-I molecules), may have lower immunogenicity than either a heat shocked, but recovering cell or a necrotic cell.

Accordingly, with accurate temperature and time controls therapy employing heat shock protein induction becomes available. Other adjunct therapies available with accurately controlled thermotherapy are, for example, release agent systems associated with a heating instigated release, radiation treatment, chemotherapy and radiochemotherapy.

Some approaches utilized by investigators, in the use of hyperthermia therapy, have achieved accurate temperature measurement and consequent control by inserting temperature sensors such as fiber optic temperature sensors, thermocouples or thermistors into the tissue adjacent to or integrally with implanted heaters. These fiberoptic, thermocouple or thermistor-based sensors necessarily are tethered having one or more electrical or optical leads extending externally or to a surface region of the body each time a hyperthermia therapy is administered. In the latter regard, the somewhat involved procedure often must also be repeated a number of times over many weeks or months to effect the desired therapeutic results. This becomes particularly problematic where the approach is employed in thermal therapy procedures associated with the human brain. See generally:
(40) Hynynen, et al., "Hyperthermia in Cancer Treatment." *Investigative Radiology*, 25: 824-834 (1990).

Figure 4:
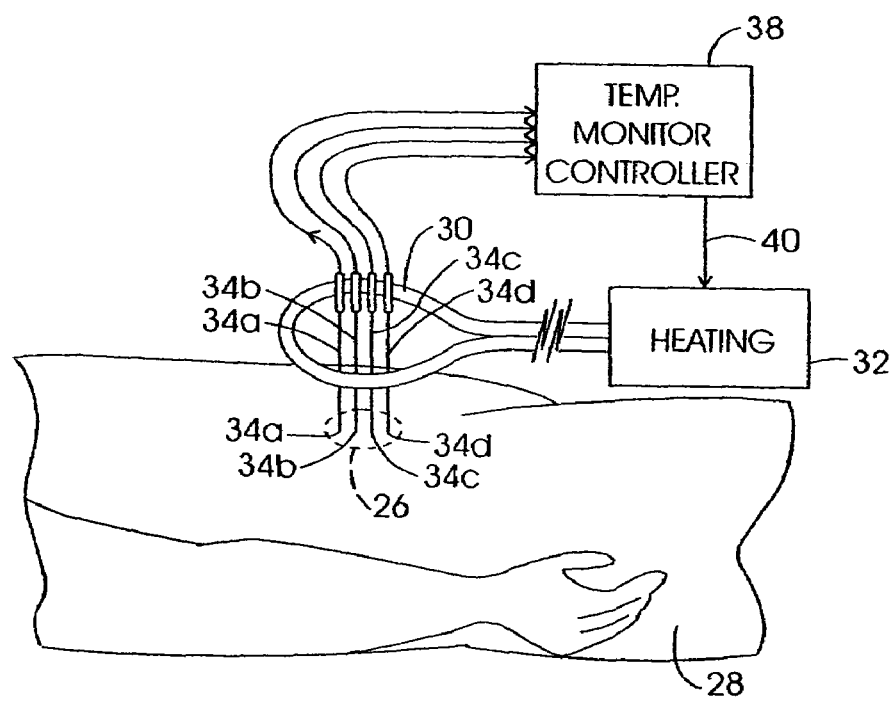
FIG. 4 illustrates a prior art approach to heating a targeted tissue volume utilizing tethered heat sensors located within the target tissue volume.

Referring to FIG. 4, the noted tethered approach to sensing internal target tissue volume subjected to thermal therapy is illustrated schematically. In the figure, a targeted internal tissue volume 26 of patient 28 is shown to be under thermotherapy treatment. Thermal energy is applied to the target tissue volume 26 from the heating coil or antenna 30 of an ACF (alternating current field) heating assembly employing a heating modality as represented at block 32. The procedure typically is carried out with a system structuring and control which evokes the sought after heating and thermal distribution at the target tissue volume 26. One or more temperature sensors 34*a*-34*d* are implanted strategically within the target tissue volume 26. Devices 34*a*-34*d* are "tethered" in that electrical leads 34*a*-34*d* extend therefrom through or adjacent to the skin to a temperature monitor/controller 38. Controller 38 additionally controls the output of the heating assembly 32 as is represented by arrow 40. In general, the heating carried out by the heating unit 32 may be enhanced through the utilization of heating elements implanted within the zone of the target tissue volume 26. A principal limitation of the technique illustrated in connection with FIG. 4 resides in the requirement that the temperature sensors 34*a*-34*d* must be inserted into and accurately positioned within the patient 28 each time thermotherapy is carried out and the procedure may be repeated often; calling for a succession of accurate sensor positionings. As noted earlier, the somewhat arduous insertion of the heat sensing elements 34a-34e becomes particularly intrusively undesirable where the procedure is carried out in conjunction with brain tumor.

Should those sensors as at 34a-34d not be utilized, the temperatures reached at the target tissue volume 26 during a procedure can only be approximated by modeling methods which are subject to substantial error due to physical differences in the tissue of given patients. In this regard, tissues will exhibit differences in vascularity, as well as otherwise assumed average properties. As noted hereinbefore, vascularity functions as a conveyance for heat removal in the vicinity of the targeted tissue region. For further discussion of thermal modeling based methods of thermotherapy, reference is made to publication (10) supra.

The present invention employs temperature sensing untethered implants which are located within a target tissue volume, whereupon, using any of the above-discussed extra body heating systems the untethered implants will provide a quite accurate readout of preselected temperature levels. These temperature sensing implants are configured as passive resonant circuits with an inductor component and a capacitor component configured as a resonant circuit. That circuit is caused to ring at a known unique resonant center frequency while the tissue being monitored is at monitor temperatures below a target Curie temperature. When the predetermined setpoint (Curie-based) temperature for the tissue is reached, then the known resonating center frequency abruptly terminates. This sharp termination of resonance in conjunction with the known center frequency is achieved by utilizing an inductor component comprised of a winding and a ferromagnetic core. The ferromagnetic core is formulated to evoke a Curie transition, for example, in magnetic permeability over relatively narrow temperature ranges, for instance, between about 0.1° C. to about 5° C. for use with sensors and as narrow as about 0.1° C. to about 1° C. for use with auto-regulating heaters. This transition in terms of relative magnetic permeability $\mu_r$, will be from about 100 to 1 to about 5000 to 1.

A highly advantageous aspect of this inductor component when employed with a passive resonant sensor resides in a stabile maintenance of the resonant center frequency of the sensors during the transition approaching the Curie temperature setpoint. During the transition, while the intensity amplitude of the sensor output diminishes, its select resonant center frequency persists. As a consequence, a target temperature predictive form of control is made available. In general, control is based upon a predetermined ratio of the instantaneous value of a signal representing the amplitude of the detector signal at the unique resonant center frequency to the maximum detector amplitude witnessed.

Figure 2:
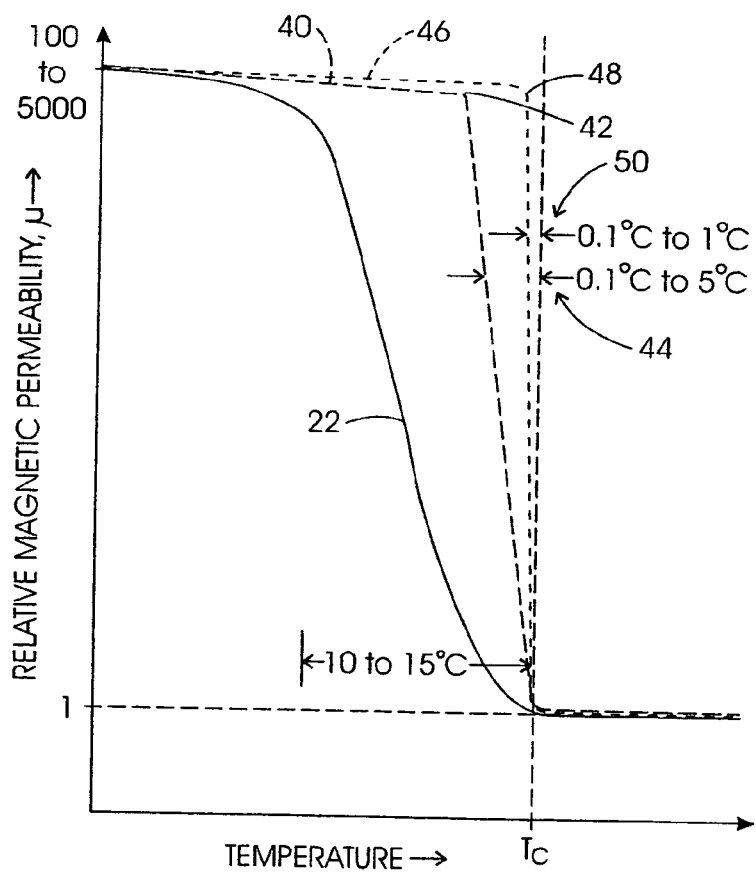
FIG. 2 shows curves relating relative permeability with temperature for sensors employing ferromagnetic components.

Returning to FIG. 2, a representation of the permeability/temperature characteristic of the inductor component ferrite of the passive resonant sensors is shown at dashed line 40 having a knee at 42 and a Curie transition range at arrow pair 44. As the relative permeability passes the knee 42 sensor output at its unique resonant center frequency will commence to diminish with respect to the amplitude of its intensity. Preferably the Curie transition range will be from about 1° C. to about 2° C., but may be within a range of about 0.5° C. to about 5° C. Should the Curie temperature be, in fact, reached the resonant center frequency will shift upwardly, in effect, to an off-scale value. However, system control preferably is carried out before that temperature is reached.

Where autoregulating heater implants are employed with the sensors of the invention, then the above-noted narrow Curie transistor range as it is present without inductive influence is desirable. Such a narrow range is represented in FIG. 2 at dashed curve as having a knee 48 commencing the Curie transition. The narrow transition range is represented at arrow pair 50. Because the sensors are of such small size, the methodology of the invention can be employed in connection with magnetic resonant imaging (MRI) without adverse consequence.

The temperature sensing implants may be designed to perform at their predetermined resonant center frequencies as the targeted tissue heats to a lower threshold setpoint or target level. As that Curie temperature-based threshold setpoint is approached within a Curie transition range, the output intensity of the involved sensor at its unique resonant center frequency diminishes. When the threshold Curie temperature setpoint is reached, the resonant center frequency, in effect, shifts to an off-scale value. These lower threshold temperature monitoring sensors may be combined with temperature sensing implants which experience the sharp Curie transition at an upper limit of tissue temperature. Accordingly, as the Curie temperature-based limit setpoint is approached within a Curie transition range, the output intensity of the involved sensor at its unique resonant center frequency diminishes. When the limit Curie temperature is reached, the resonant center frequency, in effect, shifts to an off-scale value. Thus, in effect, the desired thermotherapy temperature range is bracketed.

The passive resonant sensors with inductors exhibiting the Curie transition characteristic may be employed as threshold temperature measuring implants in conjunction with auto-regulating heaters exhibiting Curie temperatures above the sensor threshold temperature levels. Because such heaters require an inductive heating modality their Curie temperature based transitions ranges will be affected. However with the noted ferromagnetic materials the Curie temperature transitions will be within much narrower temperature ranges than heretofore have been observed. Looking to FIG. 5, a curve or curves relating relative magnetic permeability, $\mu_r$, with temperature again are revealed. In the figure, curve 52 shows the performance of this ferromagnetic material under the influence of low level applied magnetic field intensities. Note the sharp transition approaching Curie temperature $T_c$. Where necessary high level applied magnetic field intensities are utilized with the auto-regulators, an adequate but not as sharp Curie transition occurs as represented at curve 54. In general, in order to avoid interference of the high level applied magnetic field with the temperature monitoring passive temperature sensors the inductive fields are applied intermittently with the interrogation-based monitoring of the temperature sensors. This assures the sharp Curie transition performance with the temperature sensing implants. Depending upon the conditions involved with a particular thermotherapy procedure, the auto-regulator implants also may be employed with both lower threshold temperature determining sensor implants and upper limit temperature sensing implants. Non-magnetic metal heating sheaths also may be combined with the ferrite cores of the temperature sensors themselves. However, this is not a preferred arrangement inasmuch as the sensor associated with a heater sheath will tend to measure the temperature of the heater sheath as opposed to the tissue within which the temperature sensor is embedded. Separate heating components are useful where a more controlled localization of target tissue volume heating is called for.

Now turning to the soft ferromagnetic materials employed with the inductor components of the passive resonant circuit based temperature sensing implants as well as the auto-regulating heaters, ferrites have been considered to be crystalline reaction products of the oxides of iron and one or more other bivalent metals or bivalent metallic complexes. The soft magnetic materials are generally categorized as exhibiting a high inductance, B, for a low field, H.

Particularly for the predominating hyperthermia based procedures described herein, the soft ferrites are formulated to derive relatively low Curie point values within, for instance, a range extending from about 39° C. to about 65° C. and more typically within a range extending from about 41° C. to about 50° C. Generically, ferromagnetic materials exhibit pronounced magnetic effects occurring in atoms and ions and stem from only a limited number of metallic elements, to wit: Fe, Co, Ni and certain rare earths. Alloys or oxides of these materials typically will contain neighboring ions such as Mn to substantially enhance the atomic spin effect. Zn substitution both increases the magnetic moment of Mn and Ni ferrites and lowers the Curie temperature point of a resultant product. Such substitution will be seen to appear in ferrite formulations disclosed herein. The metal ion present in largest concentration in ferrites is $Fe^{3+}$. Because of its high ionic moment it has a high potential for controlling magnetic characteristics. Such effects are not chemical but crystallographic, being related to lattice site distribution.

The processes for preparing ferrites have an extensive but relatively short history. Such processes generally reflect the common goal of formation of a spinel structure. Starting materials typically are oxides or precursors of oxides of the cations and their processing involves an interdiffusion of metal ions of a select composition to form a mixed crystal. Ferrite powders have been produced by precipitation and digestion methods. These powders are blended, calcined and milled and, for the case of spinel ferrites, sintered for a variety of purposes including: (a) completing the interdiffusion of the component metal ions into a desired crystal lattice; (b) establishing appropriate valences for the multi-valent ions by proper oxygen control; and (c) developing a desired microstructure. During this procedure, the materials are consolidated into a body or component, for example, by die-pressing.

Figure 6:
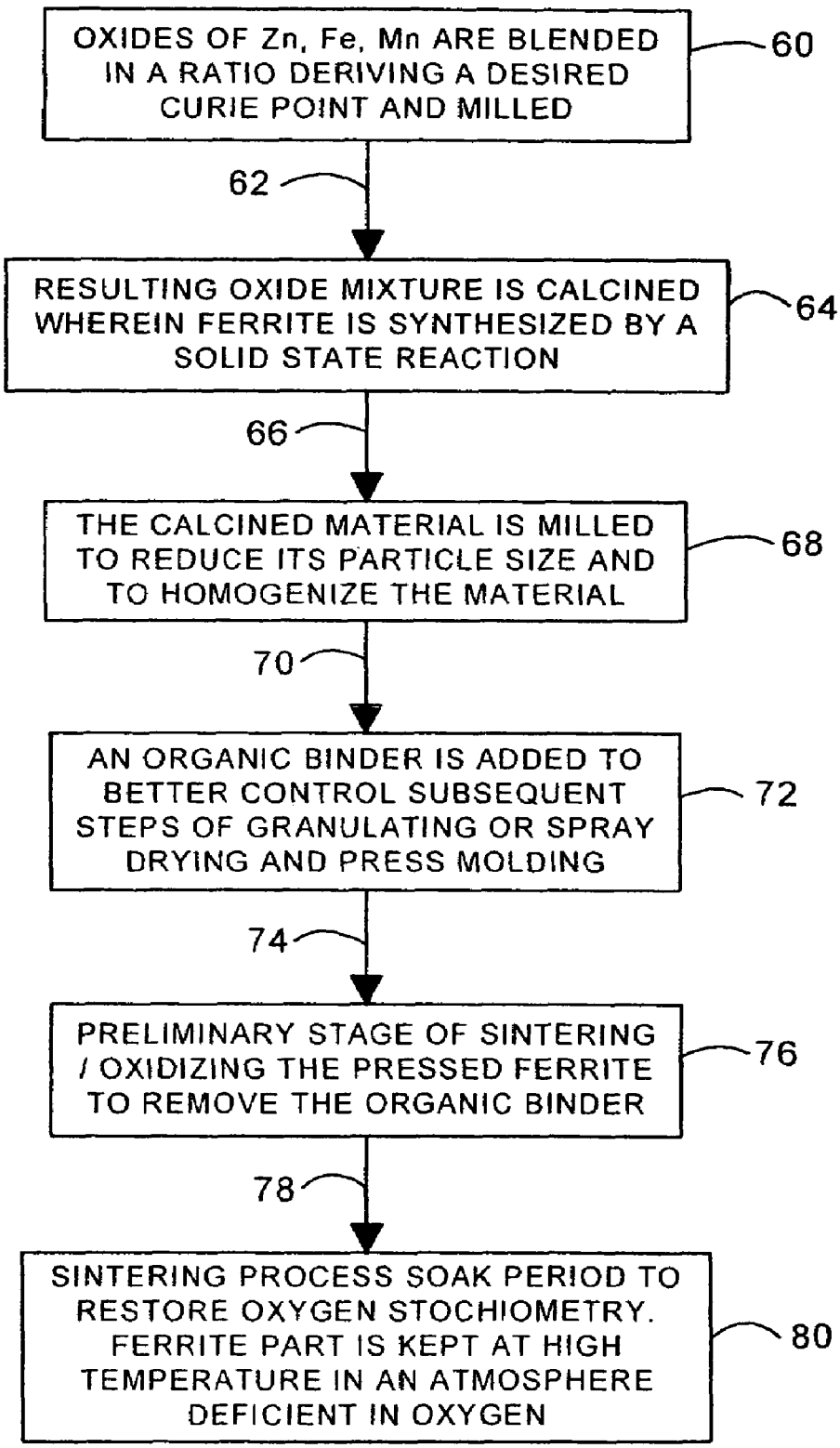
FIG. 6 is a flowchart illustrating the production of ferrites.

Referring to FIG. 6, a flow chart is presented describing the most commonly utilized ceramic process for forming manganese zinc ferrites. As represented at block 60, oxides of the metals are first blended in a ratio according to the desired composition, here providing for a desired Curie point characteristic. The oxides are milled, and as represented at arrow 62 and block 64, the resulting oxide mixture is subjected to a thermal treatment called calcining wherein ferrite material is synthesized by a solid state reaction. Generally, this step is performed in air and only a partial ferrite formation is accomplished. Next, as represented at arrow 66 and block 68 the calcined material thus obtained is then milled in order to reduce its particle size and homogenize the material. This step is commonly performed in a steel ball mill. As represented at arrow 70 and block 72 an organic binder is usually added at this stage in order to control subsequent steps of granulating or spray drying and pressing. Next, as represented at arrow 74 and block 76, in the preliminary stage of the sintering process, the pressed ferrite part is subjected to an oxidizing treatment. The aim of this treatment is to remove the organic binder added previously which at this stage is burned off by heating the ferrite part in air. Next, as represented at arrow 78 and block 80, at a later stage of the sintering process a "soak" is introduced with the aim to restore the oxygen stoichiometry wherein the ferrite part is kept at a high temperature in an atmosphere deficient in oxygen with respect to that of the stoichiometry ferrite.

One ferrite exhibiting a sharp Curie point transition of 44.5° C. exhibited the following chemistry:
Iron 49 wt %
Zinc 15 wt %
Manganese 9 wt %
Oxygen 27 wt %

In addition, calcium oxide may be added to the above formulation to advantageously increase the electrical resistivity of the ferrite material to greater than 100 ohm-cm, preferably greater than 500 ohm-cm and more preferably greater than 700 ohm-cm. This serves to increase the amplitude of the signal generated by the resonant circuit of the sensor.

See generally the following publications:
(41) Yoshifumi, A., et al., "Preparation and Evaluation of Temperature Sensitive Magnetic Thin Film With Low Curie Temperature", *T. IEEE Japan*, 118-A(2): 158-163 (1998).
(42) Goldman, "Handbook Of Modern Ferromagnetic Materials", Kluwer Academic Publishers, Norwell, Mass. (1999).

Figure 7:
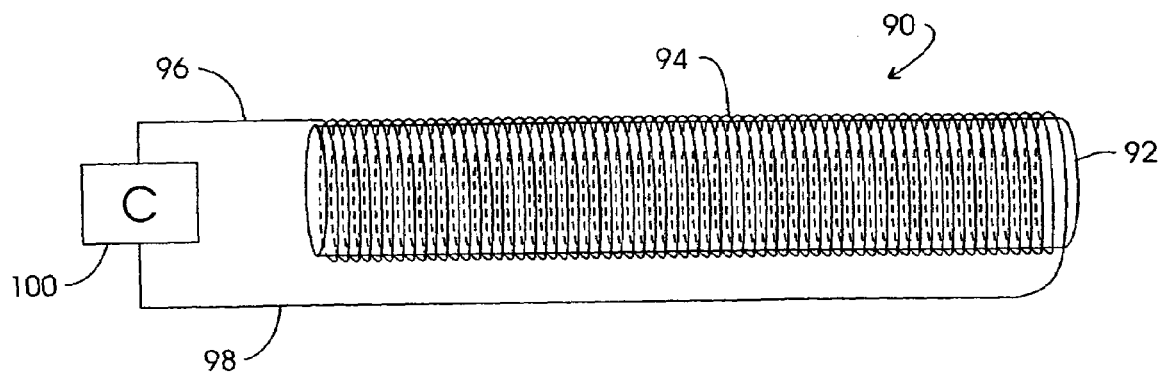
FIG. 7 is an electrical schematic diagram of a passive resonant circuit configured to provide temperature sensing.

Referring to FIG. 7, a schematic representation of the resonant circuit provided with each temperature sensing passive implant is represented generally at 90. Circuit 90 is configured with a ferrite core component 92 having a Curie transition range extending to the target or setpoint temperature. Turns 94 of an inductive winding are shown wound about the core 92 to provide an inductive component. Start and end termini of the windings 94 are seen to extend at leads 96 and 98 to a series coupling with a capacitor 100. The inductance which may be designed for implant 90 may be represented by the following expression:

$$L = (\text{const.}) \mu_r A N^2 / I$$

Where L is inductance; $\mu_r$ is relative permeability;
A is the cross-sectional area of the core 92;
N is the number of turns of the winding 94; and
I is the length of the ferrite core component 92.

As is apparent, the value of inductance may be developed by adjusting the number of turns, N. When excited by an excitation electromagnetic field from an extra body location, the circuit 90 will resonate in accordance with the expression:

$$f_0 = \frac{1}{2\pi\sqrt{LC}}$$

where $f_0$=the resonant center frequency of the resonant circuit;
L is inductance; and
C is capacitance.

With this arrangement, a plurality of temperature sensing implants may be developed, each with a unique resonant center frequency. The particular resonant frequency which is utilized in carrying out temperature sensing of a target tissue volume in general, will fall within a range of from about 100 kHz to about 2 MHz. As is apparent from the above two expressions, when the circuit 90 is exposed to temperatures approaching the Curie temperature, relative permeability will drop to a value approaching one and, in consequence, the reluctance of the inductor cast decreases and the associated signal output level issuing from the sensor decreases by 3-fold to 10-fold or more, indicating that the Curie temperature is close at hand. The above expressions also reveal that the various resonant frequencies employed with the system can be adjusted by controlling the number of turns 94 and the value of capacitance for capacitors as at 100. Accordingly, each temperature sensor implant will exhibit its own unique resonant center frequency based signature.

In general, the windings 94 are formed of materials including copper, silver, gold, aluminum, platinum or other non-magnetic, low electrical resistivity metals or alloys and will exhibit diameters within a range of from about 0.001 inch to about 0.020 inch and preferably from about 0.002 inch to about 0.010 inch; and most preferably within a range of about 0.003 inch to about 0.007 inch. Because the temperature sensing implant circuits as at 90 are excited from an extra body applied excitation electromagnetic field generated as a broad spectrum pulse exhibiting an excitation interval, it is desirable that resonant ringing of circuits as at 90 continue for an interval extending beyond that excitation interval. To achieve this ringing persistence interval it has been found desirable to configure the implant circuits as exhibiting a high quality factor, Q. Q is a measure of the sharpness of a resonant peak at the −3 dB point. The Q of a series RLC circuit may be expressed as follows: $Q = \sim_0 L/R$. Accordingly, it is desirable to maintain lower values of resistance which is a factor in the selection of a particular inductive winding wire diameter. It is preferred that the inductive windings 94 be in a single layer in order to avoid a resistance elevating proximity effect. However, in general, between one and about ten layers may be employed. The dimensions for the core length, l, can vary substantially, for example, within a range of from about 5 mm to about 100 mm; more preferably from about 5 mm to about 40 mm; and most preferably, from about 5 mm to about 20 mm.

Figure 8:
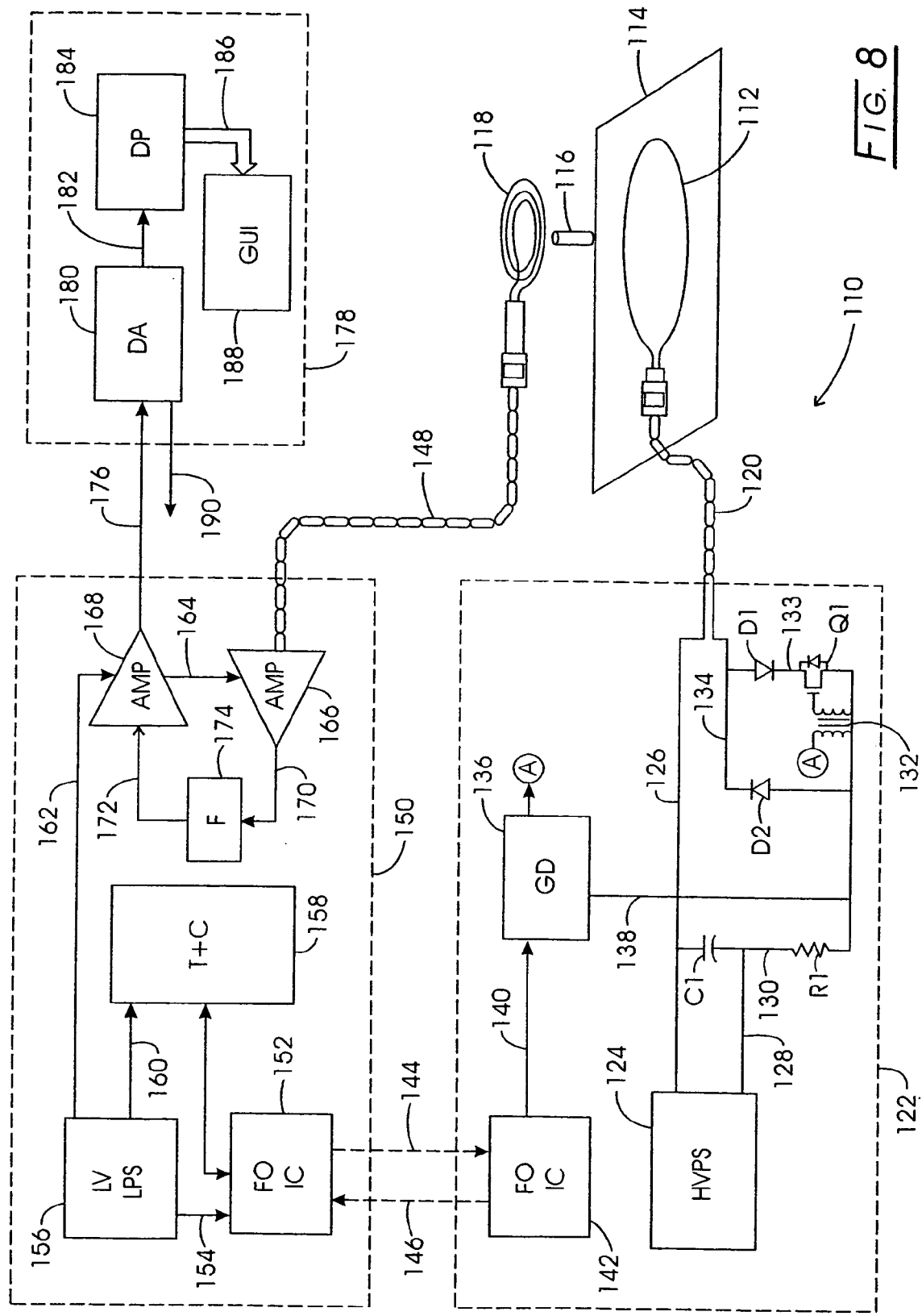
FIG. 8 is a schematic block diagram of a temperature monitoring system according to the invention.

Referring to FIG. 8, a schematic and block diagrammatic illustration of the system at hand is presented. Represented generally at 110, the system is shown to include an excitation antenna 112 located in a plane 114 which, in general, will be located beneath the patient. A passive resonant sensor implant will have been located within the target tissue volume of the patient. An exemplary temperature sensing implant is represented at 116. Extending over and about the implant 116 is a sensor antenna 118, having a diameter of about 18 inches. Excitation antenna 112, may, for example, be provided as a single turn of 14 awg wire having a diameter of about 20 inches. Antenna 112 is seen coupled via cable 120 to the output of an excitation assembly represented at block 122. Assembly 122 functions to supply an excitation pulse of about one microsecond duration from a 1000 volt power supply. Accordingly, the excitation antenna 112 may carry a 40 amp peak current with a waveshape that is approximately one cycle of a damped sinusoid. In this regard, note that the high voltage power supply is represented at block 124 having a plus output line 126 extending to antenna 112 and a negative output line at 128. A high voltage storage capacitor function, C1 is located between lines 124 and 128 as represented at line 130. Also represented at line 130 is a small sense resistor function, R1. Line 130 also is shown extending to a gate drive transformer 132 which receives a gating input at node, A, and functions to gate a high voltage transistor function Q1 into conduction. Note that one side of transistor Q1 is coupled with line 130, while the opposite side, represented at line 133, extends with steering diode D1 to a line 134 coupled to antenna 112. Line 134 additionally extends with steering diode D2 to line 130.

A gate drive circuitry is represented at block 136 shown connected to line 132 via line 138 and providing the earlier-noted gating pulse, A. Gate drive circuitry 136 is actuated in response to a forward drive input represented at arrow 140. That input is derived at a fiberoptic interface circuit represented at block 142 which is seen responsive to an optical drive input represented at dashed arrow 144. An interface optical output is represented at dashed arrow 146. In operation, when a forward drive gating pulse is applied to transistor Q1 for about one microsecond current flows from the storage capacitor function C1 through excitation antenna 112, then returns through diode D1, transistor function Q1 and returns to the storage capacitor function C1. That represents the forward half-cycle of excitation of antenna 112. When transistor Q1 is turned off, current flows through diode D2, through excitation antenna 112 and returns to the capacitor function C1. The result is a single cycle sinewave excitation. Sense antenna 118 is blocked during this excitation interval, in as much as the excitation field generated from excitation antenna 112 will tend to couple with antenna 118. Antenna 118, which may be provided as a paired wire device is connected through cable 148 to a detector and control function represented at block 150. Function 150 includes fiberoptic interface circuitry represented at block 152. Circuitry 152 is seen to be interactively associated with optical transmission arrows 144 and 146 and is powered as represented at arrow 154 from a low voltage linear power supply represented at block 156. Power supply 156 additionally powers a timing and control logic function shown at block 158 as represented at arrow 160. Function 158 serves to carry out appropriate logic including the duration of the excitation pulse, delays before the enablement of antenna 118 and the like.

Also powered from low voltage linear power supply 156 as represented at arrows 162 and 164 is a front-end amplification function represented at 166 and an output amplification function represented at 168. The detected signals from sense antenna 118 are both amplified and filtered following a delay interval occurring subsequent to the excitation interval. That delay interval permits a sufficient dampening of the excitation pulse so as not to interfere with the resonating signals emanating from the sensor implant or implants. Note that cable 148 extends to the input of a front-end amplification stage 166. The output of the detector assembly also is seen to be amplified as represented at symbol 168. As part of the signal treatment, as represented at arrows 170 and 172, the sense antenna output is subjected to bandpass filtering as represented at block 174 as well as is stripped of any d.c. term. The bandpass evoked by the filtering function 174 will extend from, for example, about 100 kHz to about 2 MHz.

The amplified sense output is directed, as represented at arrow 176 to a data acquisition and control network represented in general at block 178. This analog signal is sampled at a very high rate with an analog to digital conversion approach. With this digital approach, the system may apply the full power of signal averaging to lower baseline noise with respect to the associated function of identifying thermal sensor broadcast centerline frequency data. For example, utilizing a point-by-point approach averaging is carried out and resonant frequency data is derived. For that purpose, Fourier transform approaches are available including the fast Fourier transform (FFT). These functions are represented at block 178 as a data acquisition block 180, the digital output of which is represented at arrow 182. Arrow 182 extends to a data processing algorithmic function represented at block 184. This algorithm is responsive to the center frequency intensity signal and data representing a corresponding unique resonant electromagnetic response of an implant temperature sensor to derive implant status data as detector outputs. These Fourier-type outputs representing a unique resonant center frequency will diminish in amplitude as core Curie temperature is approached. A ratio of such diminution (instantaneous to maximum amplitude) is used for control and monitoring purposes. As represented at bus arrow 186 and block 188 resultant implant status data is asserted to a graphical user interface or readout assembly to provide visibly discernable information to the operator. Signals to instruct the system to commence carrying out an excitation and sensing sequence may be evolved from the data acquisition function 180. Such signal introduction is represented at arrow 190.

Figure 9:
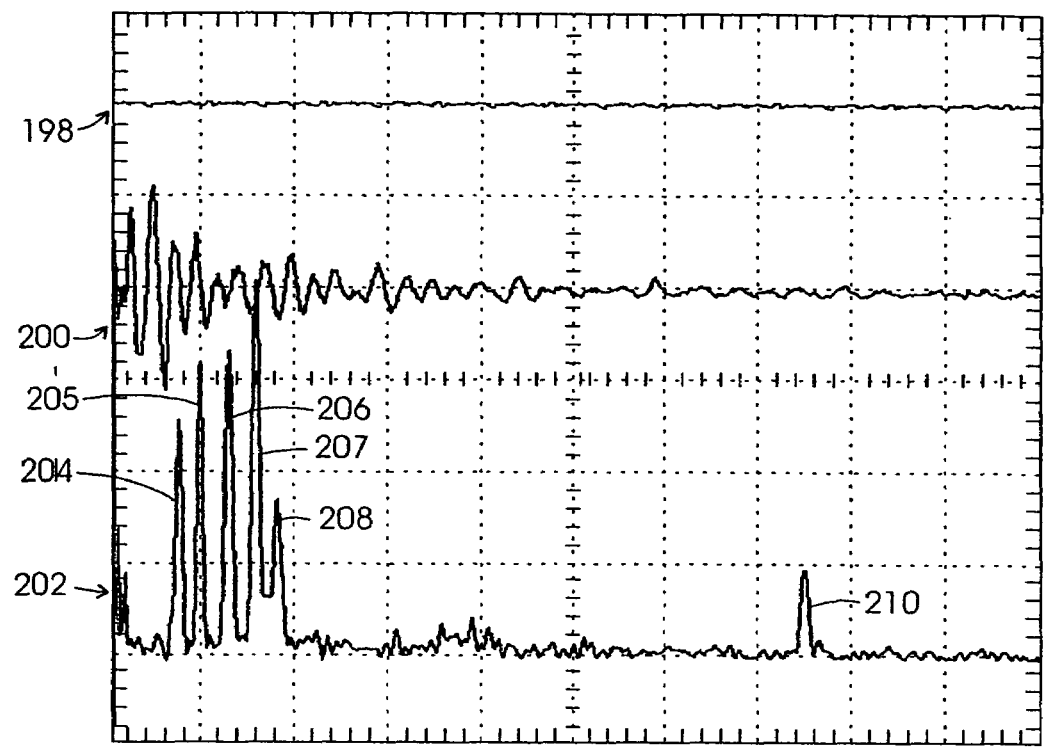
FIG. 9 is an oscillotrace showing a sensing response and associated resonant frequency intensity.

Referring to FIG. 9, oscillotraces are presented which were derived from a bench testing of the temperature sensor implants. Five of the sensor implants were utilized having a 1.5 mm diameter and a length of 20 mm. The sensors were configured to derive outputs with center resonant frequencies of 400 kHz, 500 kHz, 700 kHz, 800 kHz and 900 kHz. Curie transition temperatures for all but the 500 kHz device were 41° C., the 500 kHz device having a Curie temperatures of 44° C. These five sensors were located in an array pattern on an approximately 1 cm grid. This grid was located within a water bath having a temperature of 25° C. The bottom of this water bath was located at the plane of an excitation antenna having a diameter of 20 inches and formed of the earlier-noted 14 awg wire. The sense antenna was arranged having a diameter of 18 inches and was formed of paired turns of 20 awg wire and located 12 inches above the excitation antenna. In the figure, the trace at level 198 is the current waveform that was used for triggering. However, the waveform is not visible in the figure. The trace at level 200 is a time domain representation of the analog amplified output of the sense antenna-based detector system. Level 202 represents a fast Fourier transform (FFT) of level 200. The scale for level 202 is 500 kHz per division. The system also averaged eight acquisitions to derive these FFTs at level 202. Frequency intensity identifier 204 is the FFT response from the 400 kHz sensor. Frequency intensity identifier 205 is the FFT based response to the 500 kHz based sensor. Frequency intensity identifier 206 is the FFT based output representation for the 700 kHz based sensor; frequency intensity identifier 207 is the FFT derived evaluation of the output of the 800 kHz sensor; and frequency intensity identifier 208 is the FFT based evaluation of the output of the 900 kHz sensor. A spike at 210 is a spurious anomaly. It was determined that moving the array up or down on a Z-axis had an effect on amplitude of the FFT outputs but not on the frequency spacing. Likewise moving them in the X and Y directions within the cylinder-defined by the excitation and sense antennae had no effect upon frequency spacing. As the sensor array was heated the pattern remained very stable until a temperature of about 41° C. was reached, whereupon identifiers 204 and 206-208 disappeared, however, the identifier 205 remained. Following the above expressions, as the Curie temperature of the sensors is reached, inductance dropped, for example, by a factor of 10. As that occurs, a peak extant, for example, at 400 kHz now becomes a peak at 4 MHz.

Figure 10A:
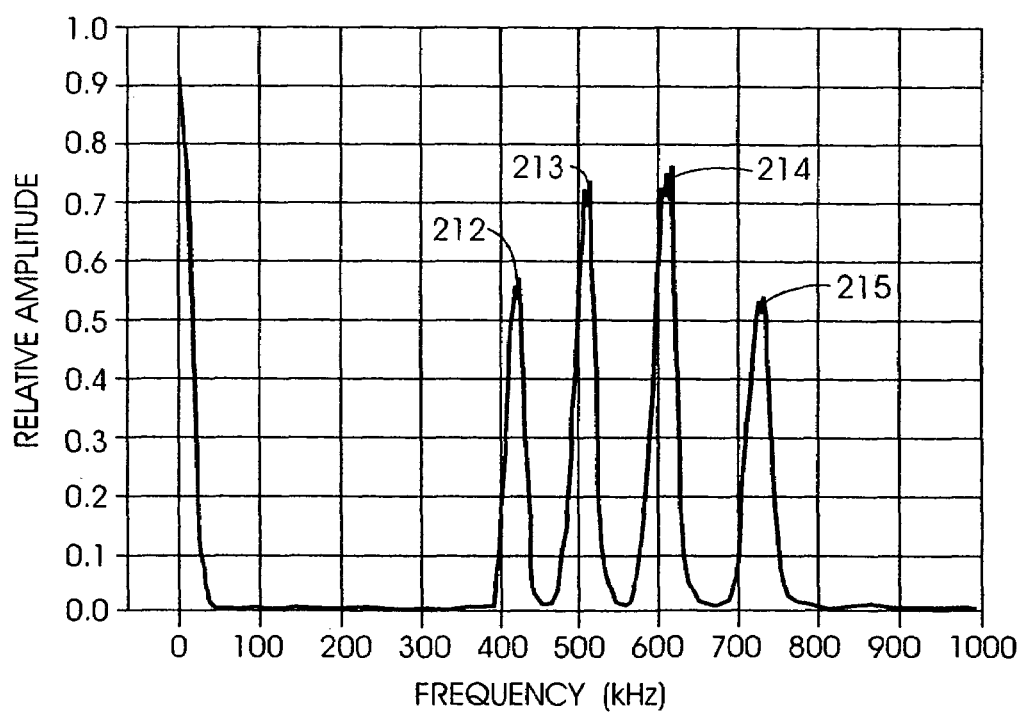
FIG. 10A is a representation of the FFT relative amplitudes of four sensors at temperatures below a setpoint temperature.

An initial concern in the earlier investigations of the instant system was addressed to the slight change in relative permeability which may occur when a given implant sensor was approaching or transitioning toward its Curie temperature. The question was posed as to whether the resonant center frequency position would shift during the temperature interval of Curie transition so as to despoil the necessary FFT derived center frequency spacing. As the sensors were heated toward their Curie temperatures, resonant center frequencies remained stable and did not increase or shift. Looking to FIG. 10A a representation of the FFT amplitudes of four sensors 212-215 having differing resonant center frequencies (kHz) is provided. The figure illustrates typically encountered FFT relative amplitudes corresponding with the intensity of the resonant output of the sensors when at monitoring temperatures well below Curie temperatures.

Figure 10B:
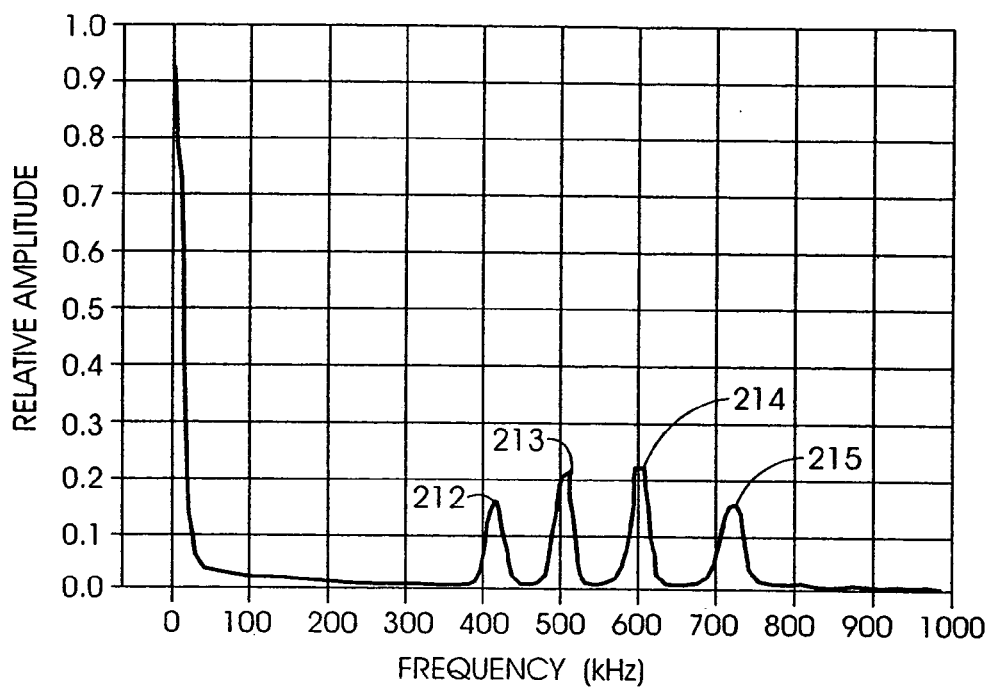
FIG. 10B is a representation of the FFT relative amplitudes of the sensors of FIG. 10A during a Curie transition.

Now referring to FIG. 10B the FFT relative amplitudes of the same four sensors 212-215 are illustrated during the course of a Curie temperature transition. Note that the resonant center frequencies have remained stable, but the detector output FFTs have diminished in relative amplitude as the temperatures monitored by the sensors approached but did not reach Curie temperature.

Figure 10C:
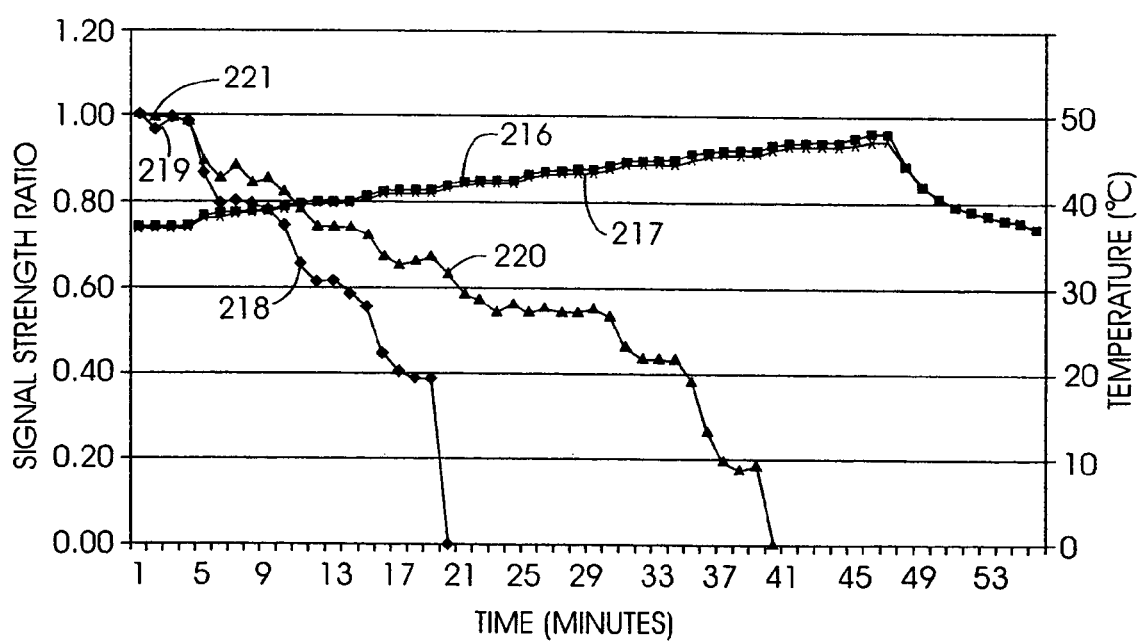
FIG. 10C is a set of curves relating the relative amplitudes of two sensors positioned with temperature sensors within a water bath environment.

Referring to FIG. 10C, actual sensor performance in a bath of water which was heated over a period of time is plotted with respect to temperatures and sensor output signal strength ratio for two sensors. A thermocouple was plotted with each sensor and the time/temperature plots thereof are shown at curves 216 and 217. Curve 218 plots the signal strength ratio of a sensor having a 41° C. Curie temperature. Note that as associated temperature curve 216 rises from a nominal human body temperature of about 37° C. the signal strength ratio remains at one at region 219, then commences to drop; essentially dropping into noise as the bath temperature closely approached 41° C.

Curve 220 plots the signal strength ratio of a sensor having a 45° C. Curie temperature. Note that as its associated temperature curve 217 elevates from a normal human body temperature of about 37° C., the signal strength ratio remains at one at region 221, then commences to drop, essentially dropping into noise as the bath temperature closely approached 4° C.

The control system associated with this form of sensor performance measures the initial (FFT) signal amplitude for each sensor with respect to its unique resonant center frequency. Typically there resonant center frequencies are separated by about 50 kHz to about 75 kHz. The relative amplitude of the Fourier transform based signal of each sensor is tracked. When that relative amplitude (representing the ratio of the instantaneous amplitude to its initial amplitude) diminishes or drops to a select value, the setpoint temperature is assumed to have been reached. In this regard, the extent of any thermal overshoot is somewhat minimized.

Amplitude ratio ranges for this control approach may range from about 0.2 to about 0.7 and preferably from about 0.3 to about 0.5. The temperature value at the commencement of the Curie transition range, i.e., at the knee 42 (FIG. 2) is very reproducible (to within about 0.5° C. but is slightly lower than the true Curie temperature. A Curie transition range of about 0.1° C. to about 0.5° C. is decreased in connection with FIG. 2. The preferred transition temperature will be about 1° C. to about 2° C. lower than Curie temperature.

Figure 11A:
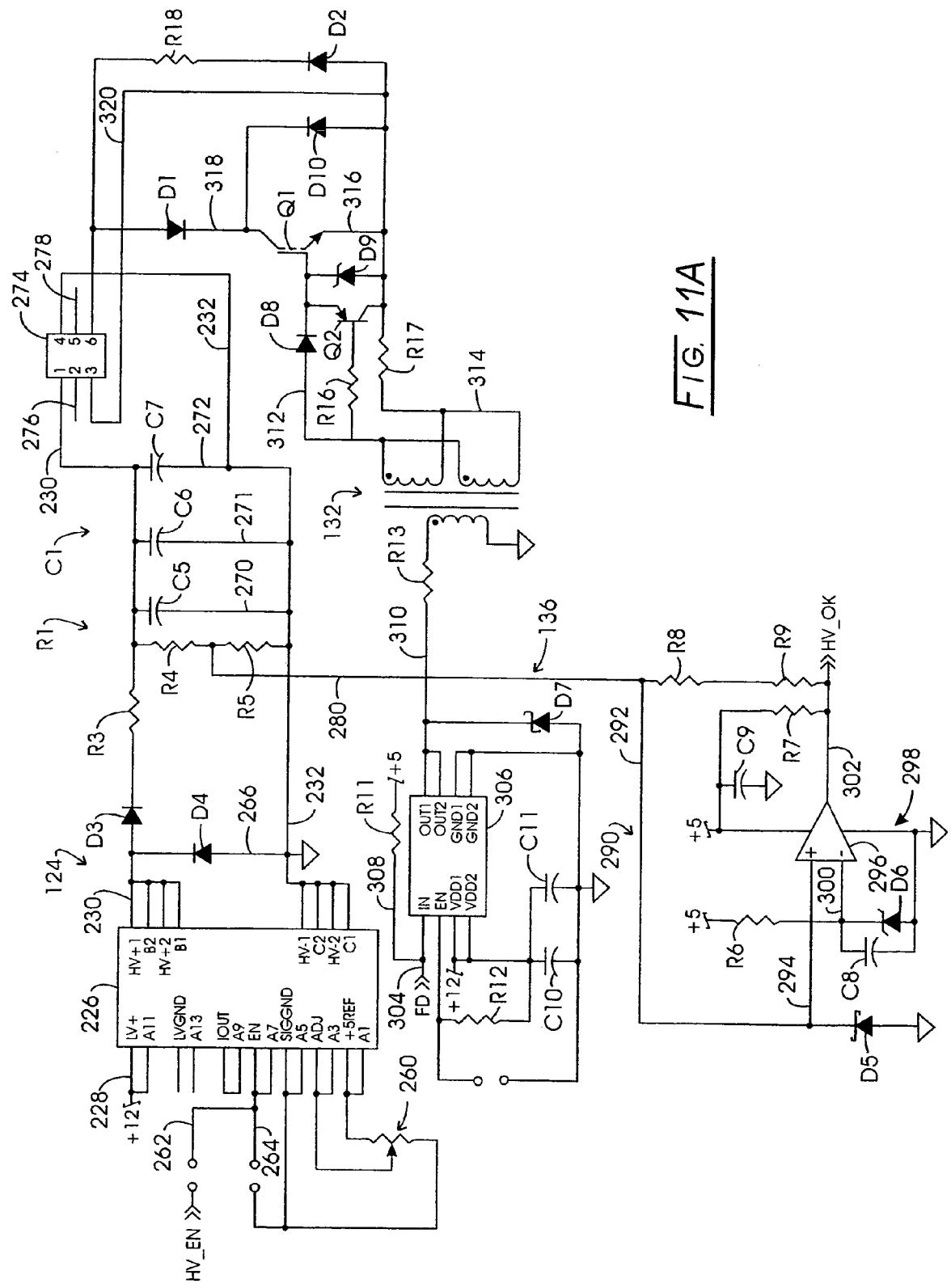
FIGS. 11A-11H are electrical schematic diagrams showing an excitation circuit employed with the system of the invention.
Figure 11B:
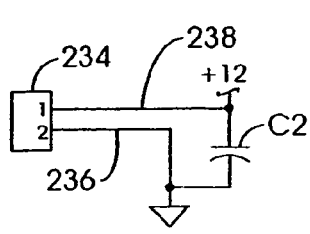

Referring to FIG. 11A, the high voltage power supply, switching, and associated gate drive circuitry as described in connection with FIG. 8 are illustrated in schematic fashion. In the figure, the high voltage power supply described earlier at 124 is shown being provided as a switching power supply 226 having a +12V input at line 228 and providing a positive output at line 230 and a negative output at line 232. Looking momentarily to FIG. 11B, the +12V input to device 226 is derived from an off-board power supply (not shown). That input is imported via a connector 234 with ground output at line 236 and +12V output at line 238, a filtering capacitor C2 being connected between lines 236 and 238. Returning to FIG. 11A, device 226 may be provided, for example, as an "A" Series High Voltage Power Supply model 1A12-P4, marketed by Ultravolt, Inc., of Ronkonkoma, N.Y. The output of device 226 at lines 230 and 234 may be adjusted at a potentiometer 260. Inasmuch as the power supply 226 is of a switching variety, it may be desirable to provide its enablement, for example, only during an excitation interval or portion thereof. Enablement is provided, for example, at lines 262 and 264, by the assertion of a high voltage enable signal input, HV_EN.

A steering diode D3 is seen positioned within output line 230. Diode D3 functions to block downstream voltages and thus protect device 226. Similarly, diode D4 coupled between output lines 230 and 232 within line 266 protects device 226 against the application of a reversed voltage. Downstream of device 226 are three energy storage capacitors C5-C7 corresponding with capacitor function C1. In this regard, capacitor C5 is coupled between output lines 230 and 232 at line 270; capacitor C6 is coupled between those output lines at line 271; and capacitor C6 is coupled between the output lines at line 272. Line 232 extends to one input of a header 274 while opposite output line 230 extends to an opposite terminal of that device. Header 274 is connected with excitation antenna 112 which is connectable with header 274 at lines 276 and 278. A ballast resistor R3 is coupled within line 230 and functions as an inrush current limiter with respect to capacitors C5-C7. Additionally, the high voltage across lines 230 and 232 is monitored at line 280 which is coupled intermediate resistors R4 and R5. These resistors correspond with sensor resistor function R1 described in connection with FIG. 8.

Monitoring line 280 extends to a voltage monitoring network represented generally at 290. In this regard, line 280 extends to lines 292 and 294. Line 294, in turn, extends to the positive input of a comparator 296. Line 292 additionally incorporates a Schottky diode D5. Diode D5 functions to protect the network 290 from overvoltages. The opposite input to comparator 296 is provided by a precision reference network represented generally at 298 comprised of zener diode D6, capacitor C8 and resistor R6. These components combine to provide a reference input at line 300 of, for example, 2.5 volts. The output of comparator 296 at line 302 is of an open collector variety and therefore incorporates a pull-up resistor R7 and noise protecting bypass capacitor C9. Resistors R8 and R9 within line 280 function to provide comparator hysteresis performance. When the high voltage across lines 230 and 232 is at an appropriate level, for example, 1000 volts, a logic high true signal, HV_OK is generated.

Looking to that circuitry, gate drive circuitry 136 (FIG. 8) again is represented in general by that identifying numeration. The excitation pulse to excitation antenna 112 is of about one microsecond duration and is generated in response to an excite or forward drive (FD) signal asserted at line 304 extending to the input terminal of a driver 306 Line 304 is coupled to +5V through pull-up resistor R11 at line 308. Driver 306 is configured with resistor R12 and capacitors C10 and C11 to provide an excite output at line 310. Inasmuch as the excite signal at line 310 drives an inductive device, a protective Schottky diode D7 is provided between it and ground. Driver 306 may be provided, for example, as a 14 Amp Low-Side Ultrafast MOSFET Driver, type IXDD414PI, marketed by Ixys Corp., of Santa Clara Calif. Line 310 incorporates resistor R13 and extends to the primary side of isolation transformer 132. The secondary side of isolation transformer 132 is coupled via line 312 to the gate of power transistor Q1 and via lines 314 and 316 to its emitter. The gate drive to transistor Q1 includes a steering diode D8, resistors R16 and R17 and transistor Q2 which functions to cause transistor Q1 to turn off quickly. A zener diode D9 protects the gate drive from overvoltages, while diode D10 protects the drive transistor from reverse voltages.

Excitation transistor Q1 performs in conjunction with two steering diodes to apply excitation energy to excitation antenna 112 as described in connection with FIG. 8. Those diodes as well as transistor Q1 are identified with the same numeration as described in connection with that figure. In this regard, a collector of transistor Q1 is coupled via line 318 incorporating steering diode D1 to 3×2 header 274 via line 314. The emitter of the excitation transistor is coupled through steering diode D2 and resistor R18 to header 274. Line 320 extending from header 274 to line 314 completes the excitation circuit. In general, transistor Q1 is turned on for about one microsecond to effect excitation of excite antenna 112 for one half of a sinusoid. The transistor then is turned off to permit generation of the opposite half cycle.

Figure 11C:
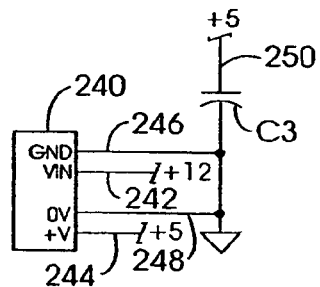

Referring to FIG. 11C, a power supply 240 is seen coupled with +12V at line 242 to provide a +5V output at line 244. Lines 246 and 248 extend respectively from the GND and OV terminals of device 240 to line 250 incorporating filtering capacitor C3.

Figure 11D:
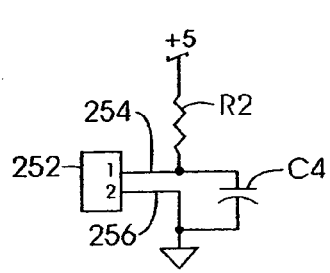

Referring to FIG. 11D, connector 252 having inputs at lines 254 and 256 and configured with resistor R2 and capacitor C4 provides another +5V input.

Figure 11E:
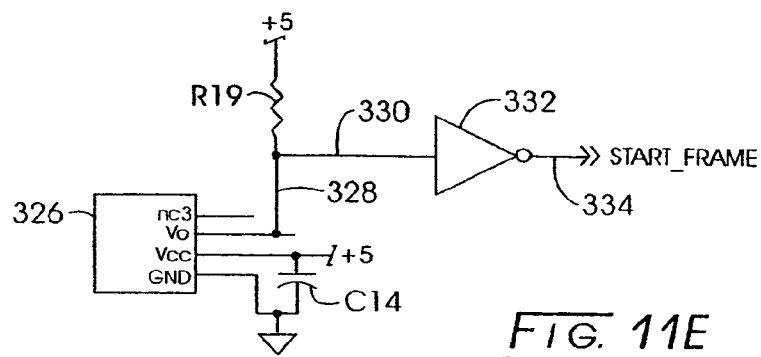

An interrogation cycle for the system at hand involves an initial excitation of excitation antenna 112 followed by a short, for example, 2 microsecond delay, following which data is acquired from sense antenna 118 (FIG. 8). For the instant demonstration, a START or START_FRAME signal is derived, for example, from a data acquisition and control network to commence each of these interrogation cycles. Looking to FIG. 11E, the receiver component of a optoisolator as shown at 326 serves to receive and transfer this START signal via line 328 to line 330. Device 326 is configured with capacitor C14 and may be provided, for example, as a 40 kBd 600 nm Low Current/Extended Distance Link Receiver, type HF BR-2533 marketed by Agilent, Corp., of Palo Alto, Calif. Line 330 is coupled through pull-up resistor R19 to +5V and extends to the input an inverter 332 to provide the START_FRAME signal at line 334.

Figure 11G:
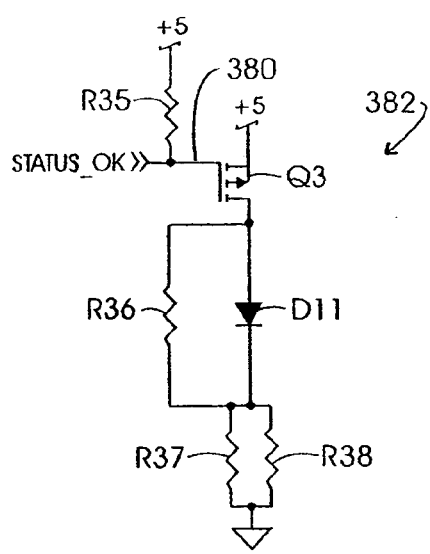
Figure 11H:
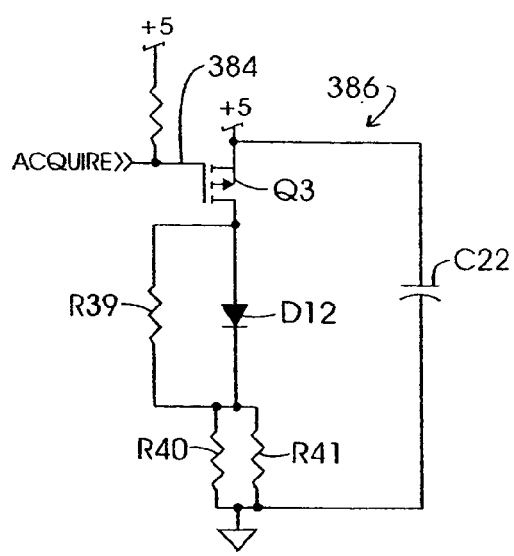
Figure 11F:
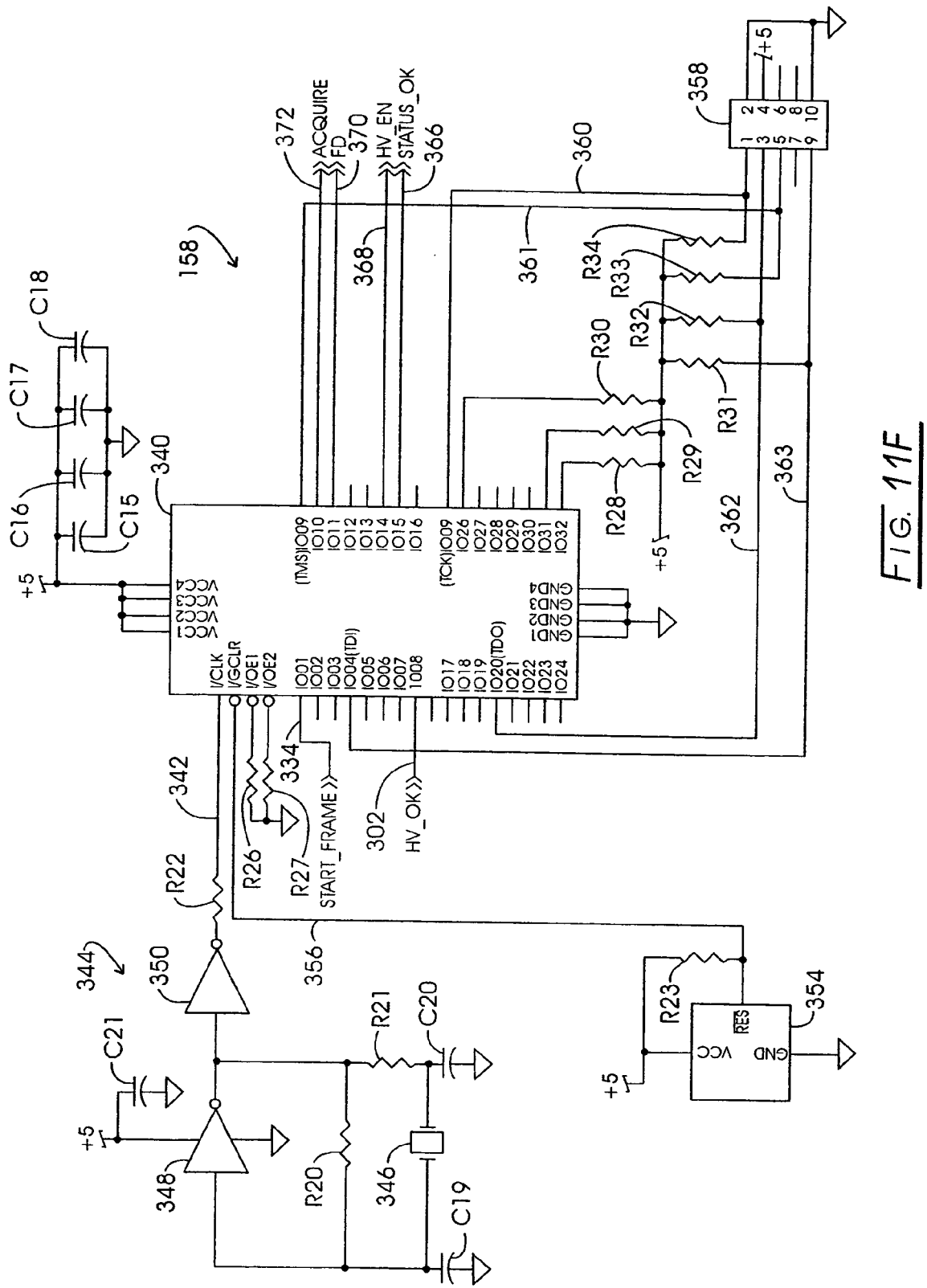

Referring to FIG. 11F the START_FRAME signal reappears in conjunction with line 334 extending to an input of a programmable logic device (PLD) 340. Representing a component of the control circuit of the system at hand, PLD 340 is configured with filter capacitors C15-C18 and receives a clock input at line 342 from the clock network represented generally at 344. Network 344 is comprised of a 1 MHz crystal configured with capacitors C19 and C20, resistors R20 and R21 and inverters 348 and 350. Inverter 348 is configured with capacitors C21 and clock input line 342 incorporates an input resistor R22.

A start-up reset function is provided by a device 354, which is configured with resistor R23 and provides a Clear input signal to PLD 340 via line 356. Device 354 may be provided as a Supply-Voltage Supervisor and Precision Voltage Detector, model TL7757CD marketed by Texas Instruments, Inc. of Dallas Tex. PLD 340 further is configured with resistors R26 and R27 and is programmable from junction device 358 having outputs at lines 360-363, which are coupled with pull-up resistors R28-R34. PLD 340 receives status information, for example, the HV_OK signal at line 302, interlock information and the like and where operational criteria are in order, provides a STATUS_OK signal at its output line 366. Additionally, the HV_OK signal is employed to provide the power supply enabling signal, HV_EN at line 368. That signal may be directed to acquisition and control circuitry and additionally may be employed to enable power supply 226 as described in connection with line 262 in FIG. 11A. In the presence of the status signal line 366 and high voltage enable signal at line 368, PLD 340 may respond to a START_FRAME signal at line 334 to derive the excite or forward drive signal, FD at line 370. It may be recalled that the excite signal is directed to line 304 in FIG. 11A. Following an appropriate excitation delay permitting both the development of the second half cycle of the excitation sinusoid and sufficient damping to permit activation of the detection system, an ACQUIRE signal is generated at line 372.

The STATUS_OK signal from line 366 is optically transmitted to the acquisition and control features of the system. Looking to the FIG. 11G the STATUS_OK signal is seen introduced via line 380 to the input of an opto-transmitter represented generally at 382. Transmitter 382 may be provided as a 1 MBd 600 nm High Performance Link Transmitter, model HFDR-1532 marketed by Agilent, Corp. of Palo Alto, Calif. Line 380 is coupled to +5V through pull-up resistor R35. Device 382 is configured with transistor Q3, light emitting diode D11 and resistors R36-R38.

In similar fashion the ACQUIRE signal at line 372 (FIG. 11F) is optically transmitted both to detection circuitry and to control and acquisition circuitry of the system. Looking to FIG. 11H the ACQUIRE signal is asserted via line 384 to the input of an opto-transmitter represented generally at 386. Device 386 may be provided as a 40 kBd 600 nm Low Current/Extended Distance Link Transmitter type HBR-1533 marketed by Agilent, Corp., of Palo Alto, Calif. The device is seen configured with transistor Q3, light emitting diode D12, resistors R39-R41 and capacitor C22.

Device 382 optically conveys the STATUS_OK signal to an optical receiver for further disposition. Referring to FIG. 12A the STATUS_OK opto-receiver is shown at 390. Device 390 is configured with capacitor C24 and resistor R44 and may be provided as a 40 kBd 600 nm Low Current/Extended Distance Link Receiver model HFBR-2533 marketed by Agilent, Corp. (supra). The output of receiver 390 is directed to a line driver 394 which functions to provide a corresponding STATUS_OK output at line 396 incorporating resistor R45. Looking momentarily to FIG. 12B, a connector 398 is shown receiving the STATUS_OK signal at line 400 for purposes of conveying that signal to control and data acquisition functions of the system. Returning to FIG. 12A, device 394 is seen to be configured with resistors R46 and R47 and capacitor C25.

The ACQUIRE signal generated from PLD340 and transmitted via opto-transmitter 386 is received at opto-receiver 402. Device 402 is configured with capacitor C26 and resistor R48 and may be provided as a 1 MBd 600 nm High Performance Link Receiver, model HFbR-2532 marketed by Agilent Corp. (supra). The output of device 402 at line 404 is directed to an input of line driver 394 to provide a corresponding output at line 406 incorporating resistor R49 and extending to a BNC connector 408. Connector 408 is employed to convey the ACQUIRE signal to control and data acquisition functions of the system. Note, additionally, that the same ACQUIRE signal is tapped from line 406 at line 410. Returning momentarily to FIG. 12B, the ACQUIRE signal is seen to be asserted at line 412 to earlier-described connector 398. Note additionally in that figure, that the START OR START_FRAME signal is derived from the control system as represented at line 414.

Returning to FIG. 12A the START_FRAME signal reappears as being asserted at line 416. Line 416 is seen coupled through pull-up resistor R50 to +5V and to ground through resistor R56. Line 416 also is coupled via line 418 to an electrostatic discharge (ESD) and over-voltage protective device 420. Note that the ACQUIRE and STATUS_OK signals also are coupled with device 420 as seen at respective lines 422 and 424. Devices as at 420 may be provided as an SCR/Diode Array for ESD and Transient Over-Voltage Protection, model SP724AH, marketed by Littelfuse, Inc., of Des Plaines, Ill. Line 416 incorporates a resistor R51 and extends to an input of driver 394. The corresponding output from driver 394 at line 426 extends to the input of an optical transmitter represented generally at 428. Device 428 is configured with a light emitting diode D14, transistor Q4 and resistors R52-R54 and may be provided as a 40 kBd 600 nm Lower Current/Extended Distance Link Transmitter model HFBR-1533 marketed by Agilent, Corp. (supra). Device 428 functions to optically convey the START_FRAME signal to opto-receiver 326 described in connection with FIG. 11E.

Driver 394 further is configured with resistors R55-R59 which are coupled respectively to input terminals A2-A7 and ground.

Figure 12C:
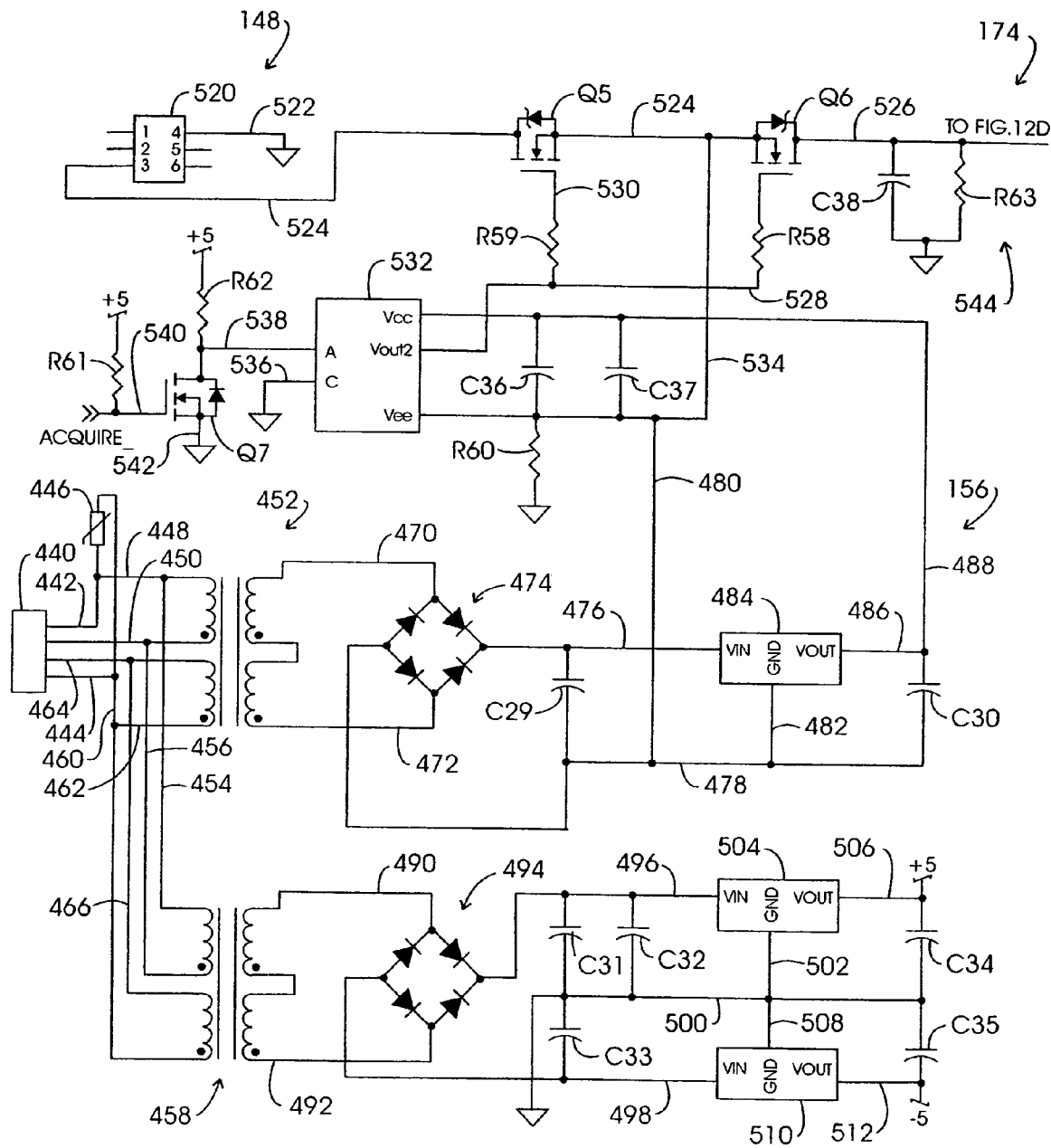
Figure 12D:
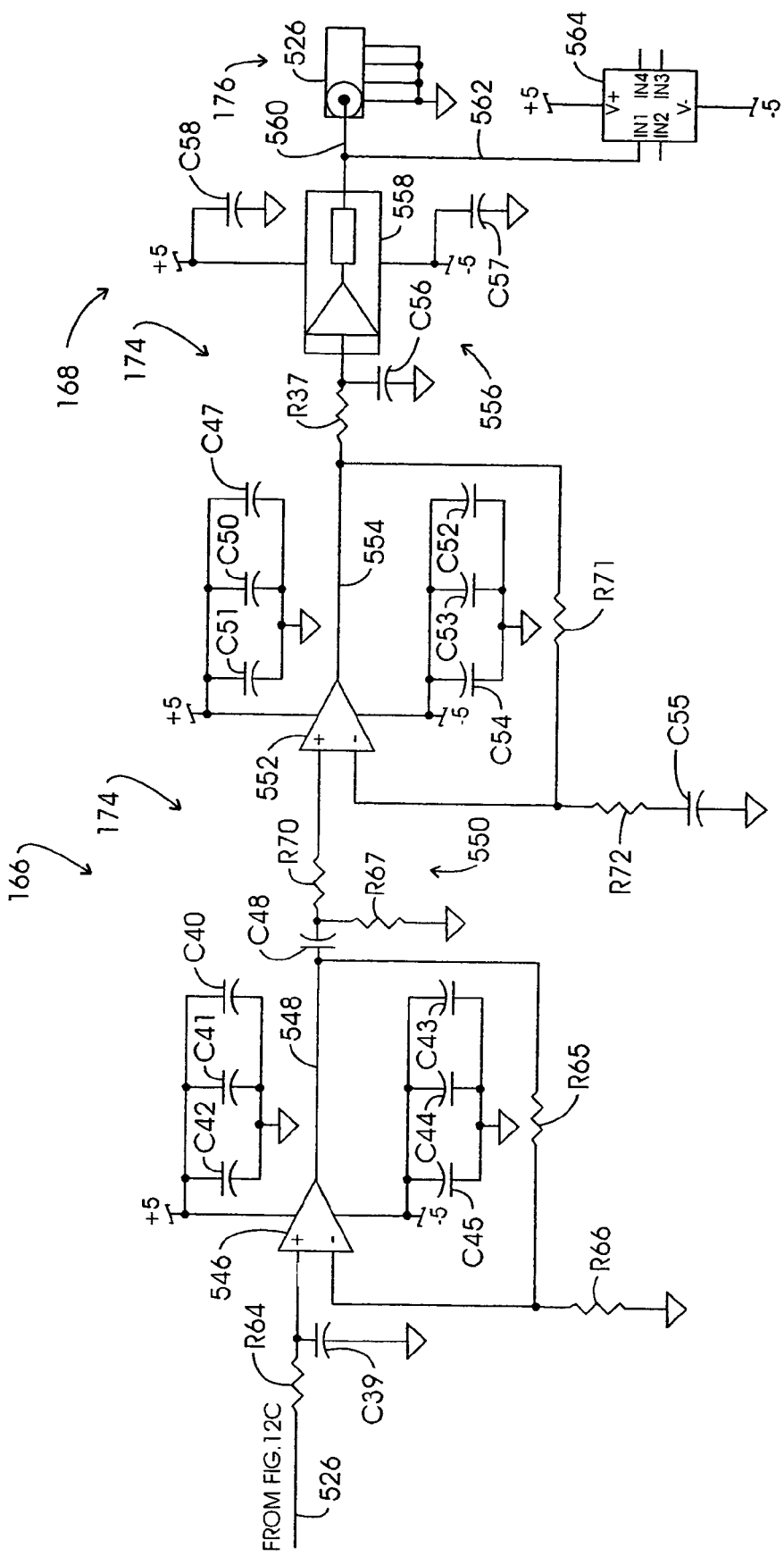

FIGS. 12F and 12D should be considered together in the manner labeled thereon. Referring to FIG. 12C, the linear power supply described in connection with FIG. 8 at 156 is identified in general with that same numeration. Power supply 156 receives line input at connector 440. Lines 442 and 444 extending from the connector are operatively associated with a current limiting varistor 446. Lines 442 and 448 as well as line 450 extend to one primary winding component of a step-down transformer represented generally at 452. Lines 448 and 450 are tapped by respective lines 454 and 456 which, in turn, extend to one primary winding component of a step-down transformer represented generally at 458. In similar fashion, lines 460, 462 and 464 extend to another primary winding component of transformer 452. Line 466 extending from line 464 and line 460 is coupled to another primary winding component of step-down transformer 458.

Secondary output windings of transformer 452 are coupled via lines 470 and 472 to a full wave rectifier represented generally at 474, the output of which is presented at line 476 in conjunction with ground level at line 478. Line 478 is seen connected to ground via line 480. A filter capacitor C29 extends between lines 476 and 478. Line 476 and line 478 via line 482 extend to a regulator 484 the output of which is directed to lines 486 and 488. The latter lines are filtered at capacitor C30 extending between lines 486 and 478. Device 484 may be provided as a Three-Terminal Positive 15 volt Regulator, model LM78M15CT marketed by National Semiconductor, Inc. of Santa Clara, Calif. With the arrangement shown, the output at line 488 is a regulated positive 15 volts.

The outputs of the secondary windings of transformer 458 are present at lines 490 and 492 which are directed to a full wave rectifier represented generally at 494. The positive output of rectifier 494 is provided at line 496, while the negative output thereof is provided at line 498. Ground level is present at line 500. Line 496 is filtered by capacitors C31 and C32, while line 498 is filtered by capacitor C33. Line 496 and line 502 extending from line 500 are coupled with a voltage regulator 504. Device 504 provides a regulated +5V output at line 506. Line 506 is filtered by a capacitor C34.

Now looking to the negative output, line 498 and line 508 extending from line 500 are directed to a negative voltage regulator 510 which functions to provide a regulated −5V output at line 512. Line 512 is filtered by a capacitor C35. Device 510 may be provided as a Three-Terminal Negative 5 volt Regulator, model LM79MO5CT marketed by National Semiconductor, Inc. (supra).

Sense antenna 118 as described in connection with FIG. 8 is a component of a detector assembly. The cable 148 extending from antenna 118 is coupled with a socket shown in FIG. 12C at 520. One side of antenna 118 is coupled to ground as represented at line 522 extending from socket 520, while the opposite side is coupled with input line 524. Input line 524 extends to the drain of MOSFET transistor Q5. The source terminal of device Q5 is coupled via line 524 to the source of another MOSFET transistor Q6. The drain of transistor Q6 is coupled with line 526. Note that transistors Q5 and Q6 are coupled in complimentary fashion. These transistors are normally in an off-state and function to block any excitation energy generated from excitation antenna 112 (FIG. 8) which tends to couple into the sense antenna 118. Two such transistors interconnected in complimentary fashion are necessitated inasmuch as their structures incorporate an intrinsic diode function which otherwise would pass a sinusoid half cycle. Gate drive to transistor Q6 is provided at line 528 incorporating gate resistor R58. Simultaneous gate drive is provided to transistor Q5 via line 530 incorporating gate resistor R59 and extending to line 528. Line 528 extends to the output terminal of a driver circuit 532. The Vcc terminal of device 532 is coupled with earlier-described power supply input line 488 while its Vee terminal is coupled via line 534 to line 524 extending intermediate transistors Q5 and Q6. Line 534 is coupled to ground through resistor R60 and filter capacitors C36 and C37 are seen to extend between lines 534 and 488. The C terminal of device 532 is coupled to ground as represented at line 536 and its input, A, terminal is coupled via line 538 to the drain terminal of MOSFET transistor Q7. Device 532 may be provided as a 2.0 Amp Output Current IGBT Gate Drive Opto-coupler, model HCNW 3120, marketed by Agilent Corp. (supra). It is actuated to gate transistors Q5 and Q6 into conduction upon application of the ACQUIRE signal to line 540 extending to the gate of transistor Q7. A pull-up resistor R61 couples line 540 to +5V. Transistor Q2 is configured such that its source is coupled to ground as represented at line 542 and its drain terminal is coupled through pull-up resistor R62 to +5V. The ACQUIRE signal is derived as represented at line 411 in FIG. 12A and is asserted under the control of PLD340 (FIG. 11F) following about a two microsecond delay which, in turn follows the one microsecond excitation of excitation antenna 112 (FIG. 8). With the arrangement shown, line 538 is normally retained in a high logic condition to retain transistors Q5 and Q6 in an off condition. Application of the ACQUIRE signal to the gate of transistor Q7 draws line 538 to the ground and effects a gating on of transistors Q5 and Q6. As these transistors conduct, a sense antenna output signal is conveyed along line 526 where it is treated by the low pass component of a bandpass filter network. These initial low pass components are represented generally at 544 and are comprised of capacitors C38 and C39 and resistors R63 and R64. Line 526 extends to the positive input of a bipolar amplifier 546, which is configured with filtering capacitors C40-C45 and provides an output at line 548. The gain of device 546 is established at resistors R65 and R66 and its output then is submitted to a high pass filter stage represented generally at 550 and comprised of capacitor C48 and resistor R67. Capacitor C48 further functions to remove any d.c. term. Next encountered resistor R70 provides noise suppression and line 548 is seen to be coupled to the positive terminal of bipolar amplifier 552. Amplifier 552 is configured with filtering capacitors C49-C55 and its gain is established by resistors R71 and R72. The output of device 552 at line 554 extends though a low pass filtering stage represented generally at 556 and comprised of resistor R73 and capacitor C56. Next in the treatment sequence is a line driver 558. Configured with filtering capacitors C57 and C58 device 558 may be provided as an Ultra-High-Speed, Low-Noise, Low-Power, Open-Loop Buffer, model MAX4201 ESA, marketed by Maxim, Inc. of Sunnyvale, Calif. The output of device 558 at line 560 is protected as represented at line 562 and device 564. In this regard, device 564 may be an SCR/Diode Array for ESD and Transient Over-Voltage Protection model number SP724AH, by Littelfuse, Inc. (supra). Line 560 is seen to extend to a BNC connector 566 which functions to connect with data acquisition components of the system. As noted above, the bandpass filtering will permit signal entry into the data acquisition system of from about 100 kHz to about 2 MHz. Resonant frequencies above the latter value tend to lack sufficient persistence beyond the interval of excitation activity. However, with improved circuit performance, the upper range, in particular, may be expanded.

Referring to FIG. 13 a process flow diagram of the system at hand is set forth. Looking to the figure, the process commences as represented at block 570 wherein the practitioner and the controller components activate a system START logic. Then, as represented at arrow 572 and block 574, the high voltage ENABLE function is activated. That signal is asserted, as described earlier herein in conjunction with lines 368 and 262. With the enablement of the switched power supply 226, as represented at arrow 576 and block 578 a determination is made as to whether the switched power supply has developed sufficient voltage level, for example, about 1000 volts. Where that is the case, then as represented at arrow 580 and block 582 a variety of interlock checks may be carried out. For example, the antenna cables, data carrying cables and interactive information cables must be secure. Where the system is thus correctly configured, then as represented at arrow 584 and block 586 PLD340 (FIG. 11F) derives a STATUS_OK signal which, as represented at arrow 588 is conveyed to the controller of the system. That controller, then as represented at arrow 590 and block 592 conveys a START or START_FRAME signal to the system as described in connection with line 414 in FIG. 12B. That START_FRAME signal is directed to PLD340 (FIG. 11F) which, in turn, develops the excite or FD signal which functions to apply a broad spectrum pulse to excitation antenna 112 (FIG. 8). As represented at arrow 594 and block 596, this broad spectrum half cycle pulse will have a duration of about one microsecond and will ring or oscillate in the manner of a full cycle sinusoid. Accordingly, as represented at arrow 598 and block 600 the system delays for about two microseconds to permit formation of the ending half cycle of excitation and to await its relaxation so as to minimize interference with the sense antenna. Following this delay, as represented at arrow 602 and block 604, PLD340 (FIG. 11F) develops an ACQUIRE signal which functions to enable the detector network as described in conjunction with line 540 in FIG. 12A. As represented at arrow 606 and block 608 the sense network is enabled by the gating on of transistors Q5 and Q6. Sense antenna 118 (FIG. 8) then acquires the signals broadcast from the resonating heat sensor implants. As represented at arrow 610 and block 612 the analog sensor signal then is submitted to low pass filter 544 and, as represented at arrow 614 and block 616 the signal then is submitted to bipolar amplification as represented at amplifier 546 in FIG. 12B. Next, as represented at arrow 618 and block 620 the analog signal is submitted to a high pass filtering stage and any d.c. term is stripped. Following this filtering, as represented at arrow 622 and block 624 the analog signal is again amplified as described at device 552 in connection with FIG. 12B. As represented at arrow 626 and block 628 the analog signal then is submitted to a low pass filter as described at 556 in FIG. 12B, whereupon, as represented at arrow 630 and block 632 the signal is introduced to line driver 558. Driver 558 then functions to convey the analog signal to the data acquisition and control features whereupon, as represented at arrow 634 and block 636 the analog signal is sampled at an analog to digital conversion stage. As represented at arrow 638 and block 640 the digitized equivalent of about 32 to about 500 sample waveforms are compiled and, as represented at arrow 642 and block 644 a point-by-point averaging of those sample digitized waveforms is carried out and as represented at arrow 646 and block 648 the averaged waveform data is analyzed to develop resonant frequency intensity data. The averaging of samples functions to minimize signal noise during use of the sensors within an animal body. Typically about 150 samples are averaged. In this regard, a sample may require about a 20 msec interval. Thus 150 samples will involve about 3 seconds, a time factor which is not long in terms of the thermal inertia of the tissue.

In general, the intensity will be of a Fourier approach wherein resonant center frequencies and their Fourier-based amplitudes are identified. Next, as represented at arrow 650 and block 652 controller logic is employed to identify the above-discussed relative amplitudes of the unique resonant frequencies associated with the sensor implants. Accordingly, a unique sensor resonant frequency is determined to be present along with its relative amplitude and is associated with the appropriate implant identifier. In this regard, the sensors may be given a numerical identification for readout purposes. With such status and identification data, then, as represented at arrow 654 and block 656 controller interface logic is employed to develop appropriate digital data for providing a readout to the operator. That function is represented at arrow 658 and block 660. Preferably, certain of the temperature sensor implants will have a Curie temperature at a lower threshold temperature, for example, 41° C., while others will be at an upper limit temperature, for example, 44° C. The readout information will apprise the operator as to whether temperature elevation toward threshold and upper limit temperatures are underway and whether the threshold temperatures have been reached or exceeded. With such information, the operator is aware that thermal therapy is underway and its status.

The discourse now turns to the physical structuring of the temperature sensing implants. Looking to FIGS. 14 and 14A, a temperature sensing implant is represented generally at 670. Implant 670 includes a ferrite core 672 disposed symmetrically about a core axis 674. Core 672 is selected having a Curie temperature exhibiting a desired transition range extending to an elected temperature. Such ferrite cores are marketed, for example, by Ceramic Magnetics, Inc., of Fairfield, N.J. In a preferred embodiment, disposed over the outward surface of ferrite core 672 is an electrically insulative polyimide internal sleeve represented generally at 676. Note that the oppositely disposed ends or edges of sleeve 676 as at 678 and 680 extend axially beyond the corresponding end surfaces 682 and 684 of core 672 to provide support for mounting the ferrite core/sleeve subassembly on an conduction coil winding apparatus. Alternately, the coil may be wound directly onto the ferrite core by securing both ends of the core in the induction winding apparatus. The end surface 682 and 684 optionally may be trimmed off, for example, with a scalpel blade prior to further assembly steps. Wound over internal sleeve 676 are the inductive winding turns defining the inductive component of the implant. Winding 686 commences with an axially extending lead portion 688, the tip 690 of which is bent at a 90° angle to provide for electrical contact with the axially disposed side 692 of a capacitor 694. The opposite end of the winding 686 extends axially beneath the winding wrap to a tip 696 (FIGS. 14B, 14C). Tip 696 is bent to define a right angle and is electrically coupled with the axially disposed side 698 of capacitor 694. Windings 686 are retained in position by an epoxy adhesive which is biocompatible for long-term implant within the human body, e.g., Epo-Tek 301 manufactured by Epoxy Technology, Billerica, Mass. Disposed over the assembly of ferrite core, internal sleeve, inductive winding and capacitor is an electrically insulative polyimide outer sleeve 700. Note that the end 702 of sleeve 700 extends beyond capacitor 694. Similarly, outer sleeve end 704 extends beyond internal sleeve 676. Assembly is completed by potting or filling the voids within sleeve 700 with the noted biocompatible epoxy adhesive. That epoxy adhesive is represented at 706 in FIG. 13A. As a final step in the implant fabrication process, its outer surfaces may be covered with a biocompatible coating represented at 708. Coating 708 may be provided as a Parylene C (polymonochloro-p-xylylene) coating of thickness ranging from about 0.00025 inch (0.00064 mm) to about 0.010 inch (0.254 mm) and preferably between about 0.0005 inch (0.012 mm) and about 0.001 inch (0.025 mm). These coatings are available from organizations such as Specialty Coating Systems, of Indianapolis, Ind.

Practitioners may find it beneficial to structure the implants as at 670 with an anchoring feature engagable with surrounding tissue to prevent any migration of the implants once implanted. One approach to providing such an anchoring structure is to extend the outer sleeve 700 beyond the outward surfaces of the epoxy potting material 706 and associated biocompatible conformal coating. For example, an outer sleeve 700 extension is represented in phantom at 714 in FIG. 14A extending outwardly from implant end surface 716. Similarly, extension of sleeve 700 is shown in phantom at 718 extending axially outwardly from implant end surface 720.

A variety of anchoring structures and techniques are employable with the implants at hand. FIG. 14 illustrates a resilient wire anchor 722 in phantom formed, for example, of a medical grade type 316 stainless steel. Anchor 722 is retained against the outer sleeve and associated conformal coating during an insertion or implantation procedure. When released from the implanting tool, the anchor will spring outwardly to engaged tissue. Other anchoring approaches are described in U.S. patent Ser. No. 10/246,347 (supra).

Temperature sensing implants as at 670 which are configured to identify lower threshold tissue temperatures may be combined with auto-regulating ferrite core based heater implants. Those ferrite core heater implants will be configured to exhibit a Curie temperature, for example, at an upper limit value above the lower threshold value. A physical structuring of such an auto-regulated heater implant is illustrated in connection with FIGS. 15 and 15A, 15B. Looking to those figures, the heater implant is represented generally at 730. Device 730 is formed having a cylindrically shaped ferrite core 732. Core 732 will exhibit a Curie temperature at an elected upper temperature limit value. Preferably, the ferrite core with exhibit a narrow Curie transition range as discussed above in connection with FIG. 5. Core 732 is surmounted by a cylindrical medical grade stainless steel sheath or tube 734. The internal diameter of sheath 734 is slightly greater than the outer diameter of cylindrical ferrite core 732 to facilitate the manufacturing procedure. Accordingly, a slight gap of annulus configuration is represented at 736. Note that the ends of sheath 734 at 738 and 740 extend outwardly along central axis 742 from the respective end surfaces 744 and 746 of ferrite core 732. The spaces defined by these stainless steel sheath extensions is filled or potted with an epoxy adhesive as described above which is biocompatible for long-term implant within the human body. This epoxy, in addition to filling the outboard regions, also migrates within the gap 736. When so constructed, the entire implant 730 is coated with a biocompatible conformal layer 748 layer such as the earlier-described Parylene. The heater structures as at 730 also may be configured with a tissue anchoring feature as described, for example, in connection with FIGS. 14, 15C and 15D. In their general operation, the heater components are inductively excited to evoke circumferentially developed currents which effect Joulian heating at monitored temperatures below the elected Curie temperature. See generally publication (9) above.

Biocompatible stainless steel heater collars or end caps can also be combined with extended ferrite cores within thermal sensing implants as at 670. However, such an arrangement generally is not recommended inasmuch as the temperature sensing components of the implant will be influenced by the Joulian heating of the heater sheaths, as opposed to the more appropriate responsiveness to surrounding tissue temperature. Combined ferrite-based temperature sensing and heater components are described in detail in the noted application for U.S. patent Ser. No. 10/246,347.

Figure 15C:
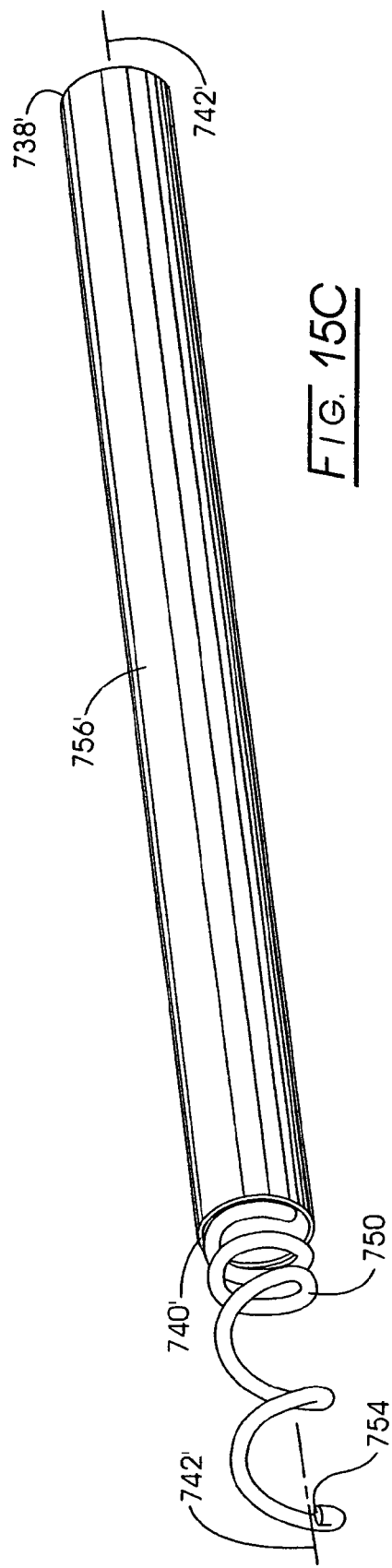
FIG. 15C is a perspective view of an implant according to the invention which incorporates an anchor.
Figure 15D:
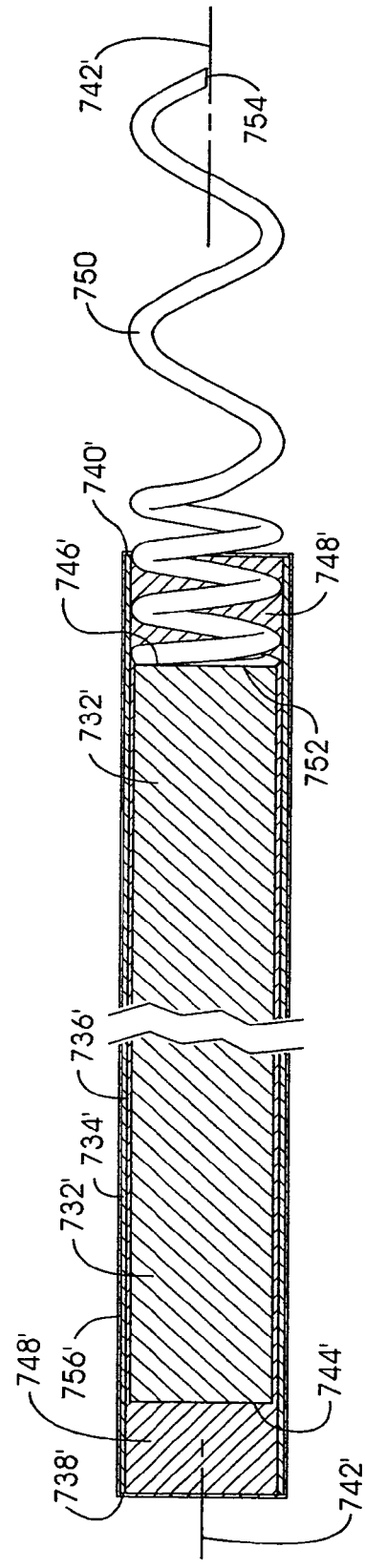
FIG. 15D is a sectional view of the auto-regulating heater of FIG. 15C.

Another anchor structure which may be employed with either temperature sensing implants as at 670 or auto-regulated heater implants as at 730 is represented in FIGS. 15C and 15D. Inasmuch as the heater implant component shown in these figures is identical to that described in FIGS. 15, 15A and 15B the same identifying numeration is employed but in primed fashion. For this anchoring embodiment, a nonmagnetic biocompatible somewhat expanded helical spring 750 is embedded within the epoxy mass 748'. In this regard, the base 752 of the spring 750 is ground so as to remain perpendicular to axis 742' and the end of the spring at 754 is cut square. In general, the epoxy embedded region of the spring 750 may be configured with three coils more closely compressed, for example, having a length of about 0.050 inch and may then integrally extend to tissue engaging two coils within an axial length of about 0.120 inch. Anchor 750 may be formed of a nonmagnetic stainless steel such as a Type 316 having a diameter ranging from about 0.1 mm to about 0.35 mm and preferably between about 0.15 mm to about 0.25 mm.

Figure 16:
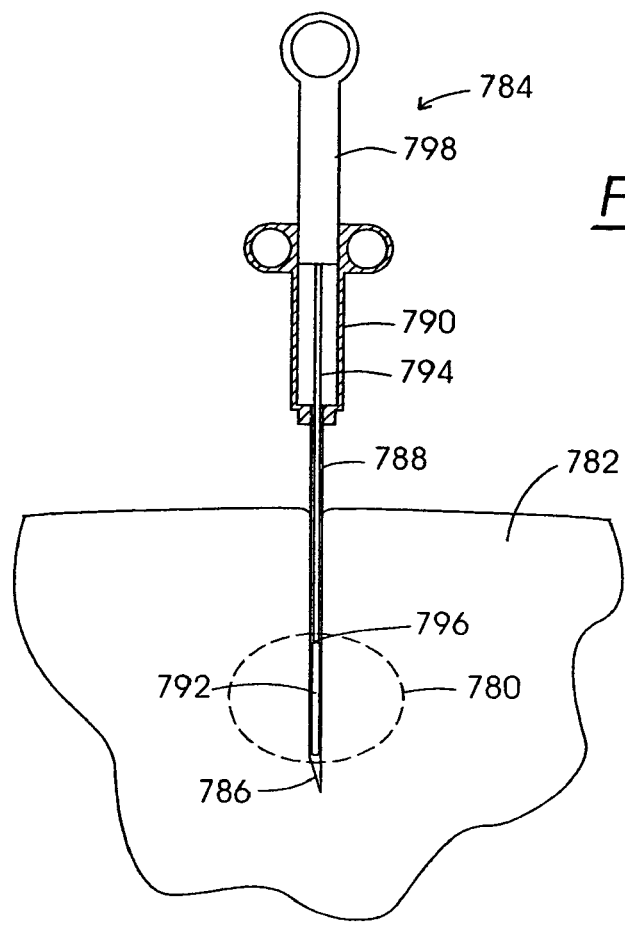
FIG. 16 is a schematic and sectional view of an implant locating instrument which may be used with the implants of the invention showing the instrument prior to releasing the implant in a targeted tissue volume'
Figure 17:
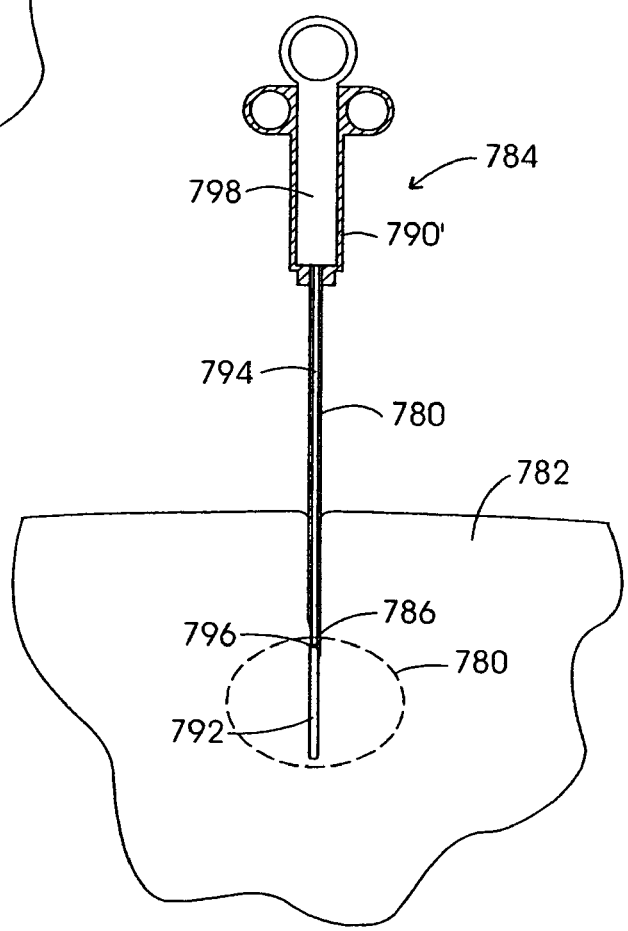
FIG. 17 is a schematic sectional view of the instrument of FIG. 16 showing the delivery of a sensor implant into a targeted tissue volume.

The implants described in conjunction with FIGS. 14 and 15 may be positioned in target tissue utilizing a variation of syringe-hypodermic needle technology. FIGS. 16 and 17 schematically represent one approach to implantation employing such technology. Radiographic, stereotactic, ultrasound or magnetic resonant imaging guidance methods or palpation are procedurally employed to position an implant within a target tissue volume. Of particular interest, the implants may be positioned intraoperatively as an aspect of open surgical procedures. For instance, a common approach to the treatment of cancer is that of tumor excision. Certain cases, for example, involving colorectal cancer will, upon gaining access to the abdominal cavity, reveal a substantially inoperative metastasis of the disease. Under such circumstances the surgical procedure typically is altered to a palliative one, for example, unblocking the colon and/or the incision is closed and other treatment modalities are considered.

However, with the instant system and method, the surgeon is given an opportunity for deploying hyperthermia-based temperature monitoring and/or heater implants by direct access. Of special interest, colorectal cancers tend to metastasize through the lymph system. Accordingly, the implants can be intraoperatively positioned within lymph nodes to provide for the induction of HSPs at the node-retained cancer cells. Other sites of tumor similarly can be implanted. Following surgical closure, the hyperthermia therapy procedures described herein can be undertaken in mitigation of the metastasis. In general, practitioners employing the method herein described with respect to hyperthermia will elect to implant the most or more accessible target tissue volume.

A target tissue volume is represented in FIGS. 16 and 17 at 780 internally within the body 782 of a patient. The syringe-type insertion device represented generally at 784 is percutaneously or intraoperatively inserted within the body 782, piercing the skin where called for by virtue of the presence of a sharp tip 786. Needle 786 is fixed to a barrel or finger graspable housing 790 and removably retains an elongate implant 792 within its internal core proximally from the tip 786. Immediately behind the implant 792 within the needle 788 is a plunger rod 794, the lower tip of which at 796 is in free abutment against the outwardly disposed end of implant 792 and which extends upwardly to a plunger handle 798. As is revealed, particularly with respect to FIG. 16, once the sharpened tip 786 of the needle 788 has been properly positioned with respect to the target tissue volume 780, then plunger rod 794 and associated handle 798 are stabilized positionally with respect to the body 782 and target tissue volume 780, whereupon housing 790 is retracted outwardly to the orientation shown at 790' in FIG. 17. This maneuver releases implant 792 at an appropriate location with respect to the target tissue volume 780. Implantation devices are described, for example, in U.S. Pat. No. 6,007,474.

Figure 18:
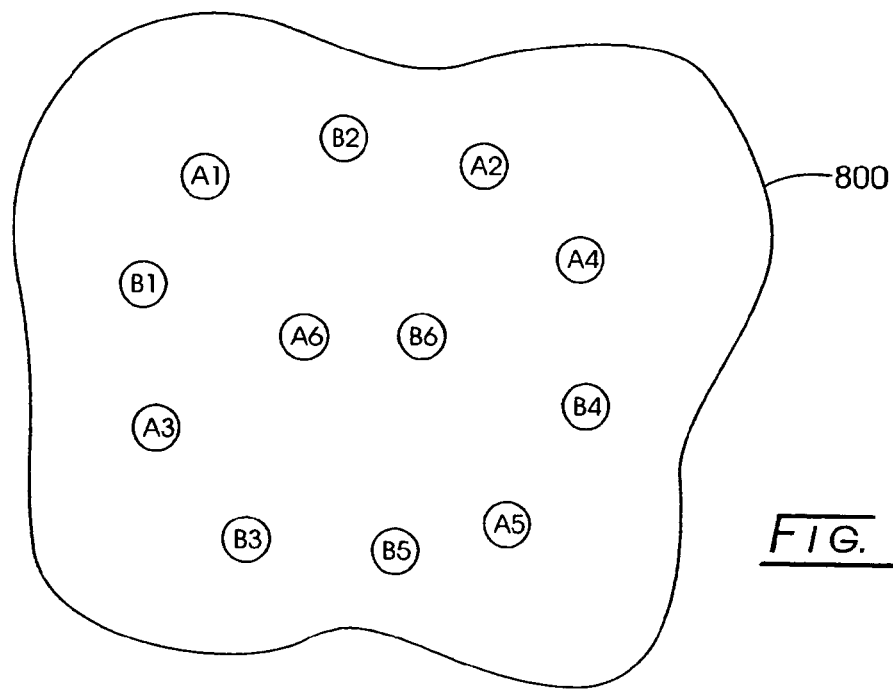
FIG. 18 is a schematic view of a target tissue volume with a map form of location of temperature sensing implants.

Upon the determining of the boundaries or periphery and the physiological state of a target tissue volume, the practitioner will determine the number of implants called for and their positioning within the localized tissue region. In effect, the location of the implants can be mapped such that their resonating responses or lack thereof may be utilized in conjunction with the map to adjust the aiming feature of the external heating system. Referring to FIG. 18, the periphery of a target tissue volume is schematically represented at 800. Within this tissue periphery 800 there are located twelve implants. In this regard, those implants labeled A1-A6 may be temperature sensing implants having inductors with a Curie temperature core establishing identifiable center frequency resonance at monitoring temperatures up to, for example, a Curie temperature of 40° C. As that Curie temperature is approached the relative amplitude of the center frequency will diminish. However, the second interspersed grouping of implants as at B1-B6 will incorporate inductors with cores exhibiting a Curie temperature of, for example, 43° C. Accordingly, implants B1-B6 will continue to resonate until the tissue volume within periphery 800 approaches 43° C. During that Curie transition range the relative amplitude of the analyzed resonant center frequency will diminish. Accordingly, the practitioner will strive to assure that implants A1-A6 are not resonating in the presence of a resonating output at implants B1-B6. In another embodiment of the instant system and method, for example, implants B1-B6 may be auto-regulating heater devices as described above having a Curie temperature at the noted 43° C. while implants A1-A6 remain as lower threshold temperature sensors having inductors with cores exhibiting a Curie temperature of 40° C.

Figure 19:
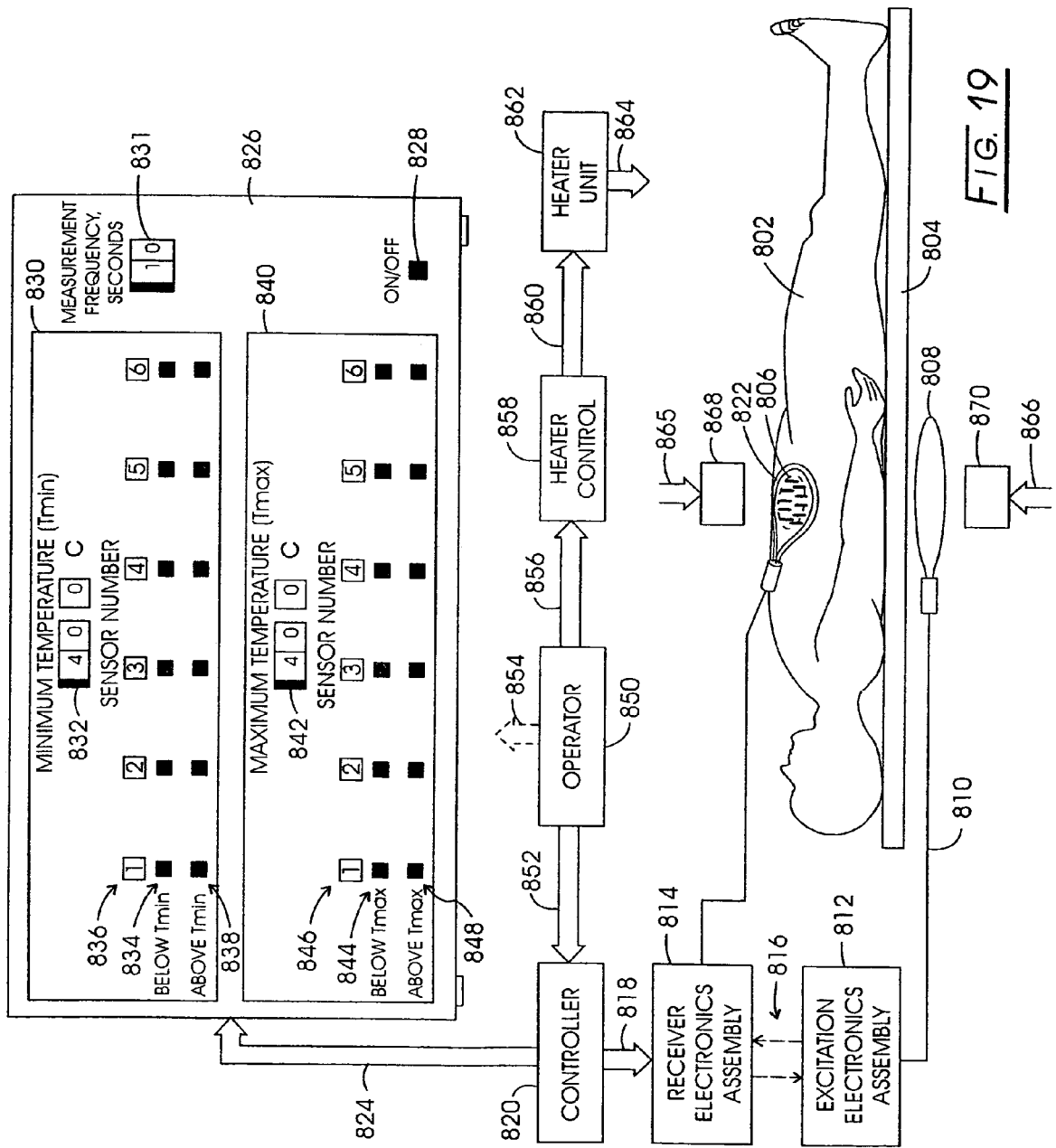
FIG. 19 is a schematic representation of one embodiment of the system of the invention.

Referring to FIG. 19, a somewhat basic implementation of the system and method at hand is schematically represented. In the figure a patient is represented at 802 in a supine position on a support 804. Support 804 is formed of a material such as a polymer permitting excitation energy to be broadcast therethrough. A target tissue volume within the body of patient 802 is schematically represented at 806 having a distribution of implants as described in connection with FIG. 18. For instance, six of the implants may be lower threshold temperature sensors which will resonate at temperatures approaching a Curie temperature of, for example, 40° C. The second grouping of six sensors will be structured to resonate at monitor temperatures approaching an upper limit value, for example, a Curie temperature 44° C. Located below the support 804 and at a location effective to cause the development of resonant outputs from the sensor implants is an excitation antenna 808 which is depicted as having a cable connection 810 with an excitation electronics assembly represented at block 812. Excitation electronics assembly 812 is configured for interactive communication with a receiver electronics assembly shown at block 814 as represented at dual dashed arrows 816. Arrows 816 may, for instance, be representative of opto-isolated communication lines. Control to excitation electronics assembly 812 and receiver electronics assembly 814 is represented by arrow 818 and a controller as represented at block 820. A sense antenna is represented schematically at 822. Antenna 822 may be flexible and essentially conform over or drape over the patient 802 in surrounding relationship about target tissue volume 806. The data acquisition and analysis components of controller 820 communicate as represented at arrow 824 with a readout schematically represented at 826. Readout or user interface 826 includes an on/off switch 828 and a measurement frequency input switch 831. The upper readout of device 826 at 830 includes an indicator apprising the operator of the lower threshold temperature elected for the therapy as represented at 832. In this regard, the indicator 832 shows a temperature of 40° C. as being the Curie temperature of the inductor component ferrite core of six implants. Below the indicator 832 are two linear arrays of visibly perceptible readouts implemented, for example, as light emitting diodes (LEDs). The upper array of LEDs is represented at 834 and is configured with six blue output LEDs each associated with a number which will be illuminated in the presence of monitoring temperatures below and approaching 40° C., i.e., below Tmin. As shown by the numeric sequence of identifiers immediately above the LEDs of array 834, each LED is assigned to be illuminated in the presence of the select resonant center frequency of a given unique implant now numbered 1-6. Below LED array 834 is an LED array 838 comprised of six spaced apart green LEDs corresponding with the numeric array 836 and configured to be illuminated when their corresponding implant will have reached the elected relative amplitude of the processed counter frequency data at a temperature approaching the lower threshold Curie temperature of, for example, 40° C. Accordingly, the green LEDs of array 838 are illuminated when their corresponding sensor implants are above the lower threshold temperature value of 40° C. and are not illuminated at monitor temperatures below that value.

A lower readout 840 is configured in the same manner as readout 830. Lower readout 840 includes a Curie temperature indicator 842 representing the programmed upper limit Curie temperature for the remaining six implants, for instance, 43° C. Each of the upper limit implants will have a unique resonant frequency when interrogated at monitor temperatures below 43° C. and those unique resonant center frequencies will provide relative amplitude data of diminishing value at temperatures approaching that upper limit value. Lower readout 840 incorporates six yellow LED implemented visual readout components represented at linear LED array 844. LEDs within the array 844 will illuminate in a yellow coloration at monitor temperatures below and approaching the upper limit of 43° C., i.e., below Tmax. Each LED will be illuminated when its associated implant is resonating at its designated unique center frequency in the presence of monitoring temperatures below the upper limit temperature, i.e., below Tmax. Aligned below LED array 844 is a red LED array represented generally at 848. As before, each of the red indicators within array 848 is associated with a numerically assigned implant identifier as at numeric sequence 846. The LEDs at 848 will be illuminated at monitor temperatures above or closely approaching the upper limit temperature, for example, of 43° C. Above that temperature any so thermally influenced implant will cease to provide the assigned unique resonant center frequency.

The system of FIG. 19 is quite basic and thus calls for active participation on the part of the practitioner or operator. That operator or practitioner is represented at block 850 providing controls to controller 820 as represented at arrow 852 and interacting with the readout or interface 826 as represented at dashed arrow 854.

The type of heater unit employed with the instant arrangement is one which employs broadcast frequencies which are non-interfering with the frequency band employed with the temperature sensing implants at hand. In this regard, the heater unit will operate at frequencies above, for instance, 2 MHz. Such heaters, for example, are employed to carry out thermotherapy by applying microwave, radiofrequency or ultrasonic energy from a variety of antenna components, for example, phased array antennae. Such products are marketed, for example, by BSD Medical Corporation of Salt Lake City, Utah.

For the instant demonstration operator 850 is shown providing interaction with a heater control function as represented at arrow 856 and block 858. Control 858, in turn, as represented by arrow 860 and block 862 provides control to such an above-described non-interference heater unit. The output is represented at arrows 864-866. The latter arrows extend to blocks 868 and 870 representing antennae of such a focused heating system.

As is apparent, the operator 850 will wish to effect control of the heater unit 862 such that LED array 834 is off, and array 838 is on at upper readout 830, while LEDs of array 844 of the lower readout 840 are illuminated and the LEDs of arrays 848 are off. Accordingly, the operator adjusts to maintain green and yellow LED excitation.

Figure 20:
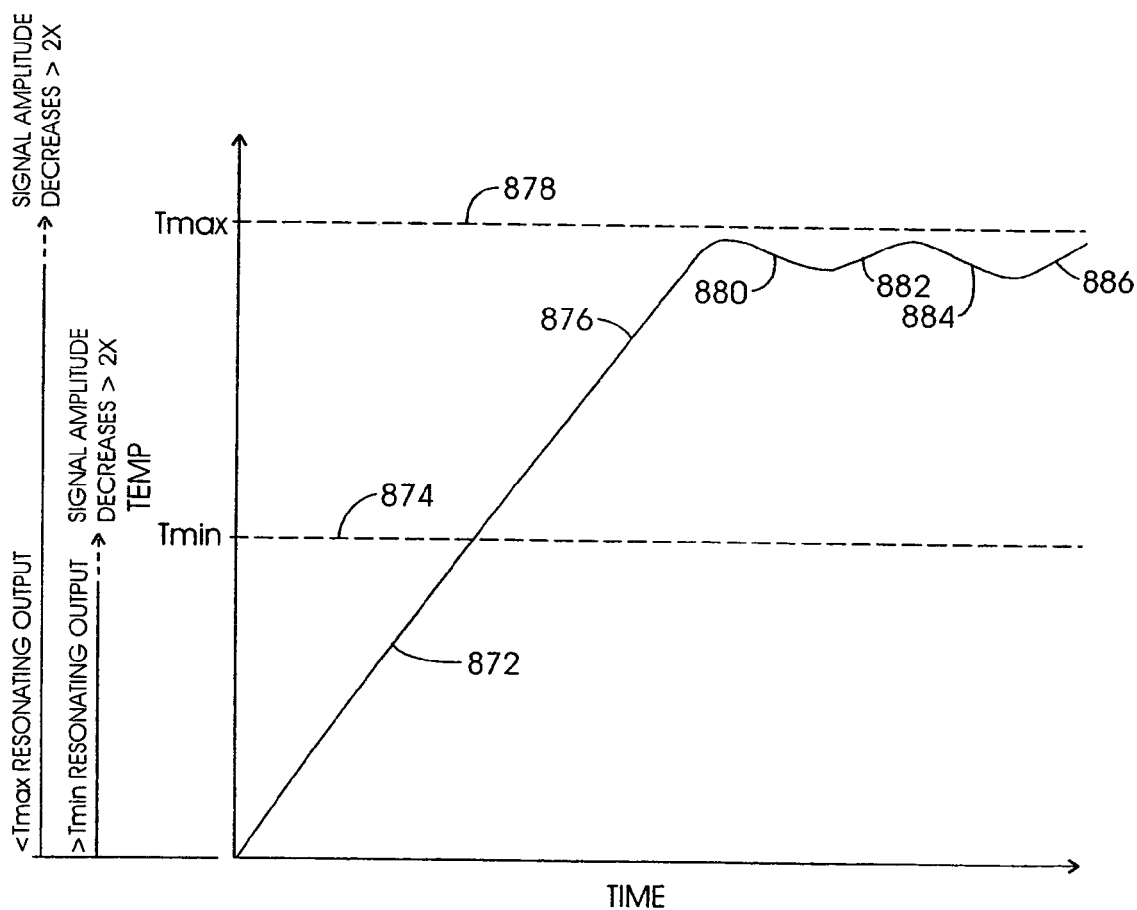
FIG. 20 is a graph schematically showing tissue temperature response to controlled extra body heating according to the invention.

Looking additionally to FIG. 20, the thermal performance of the arrangement of FIG. 19 is schematically plotted. In this regard, the figure shows a time domain abscissa and a target tissue volume temperature ordinate. As the heater unit 862 is turned on, the temperature of the target tissue volume 806 will gradually increase as represented by plot component 872. During this interval, the blue LED indicators at array 834 will be illuminated as the target tissue temperature is below the lower temperature threshold level Tmin as represented at horizontal dashed line 874. When the temperature level 874 is approached, i.e., falls within the Curie transition range with a progressive diminution is the processed relative amplitude representing an assigned resonant center frequency, the LEDs of array 834 will turn off, while those at array 838 will turn on with the noted green color. Typically a relative amplitude diminution by a factor greater than 2 (ratio of 0.5 or less) will trigger the LED performance. Resonant center frequencies of the lower threshold based implants at temperatures above their Curie temperatures will shift to a much higher resonant frequency which is not detected by the system. The heating control is now under the judgment of the operator 850 with LED arrays 838 and 844 being illuminated. During this thermotherapy period of time there may be excursions toward the upper limit target tissue temperature, Tmax as represented at plot component 876 and dashed horizontal line 878. As this temperature is approached, pertinent ones of the implants will exhibit a diminution of the processed relative amplitude representing their resonant center frequency and certain or all of the red LEDs within array 848 will illuminate. The operator then asserts control over the heater unit 862 to effect a lowering of the target tissue temperature as represented by plot component 880 and this sequence of events may continue for the interval of therapy as represented by subsequent plot components 882, 884 and 886. With the advantage of the predictable relative amplitude at center frequencies practitioners should be able to operate the system at hand such that the temperatures remain above Tmin at level 874 and below Tmax at level 878.

Referring to FIGS. 21A-21G a procedural block diagram is presented corresponding with the basic system described in connection with FIGS. 19 and 20. In this regard, operator or practitioner involvement is accentuated and non-interfering heater units, for example, in the ultrasound region are employed. Additionally, the procedure looks to thermal therapy, which includes not only hyperthermia therapy but also higher level temperature thermal therapy leading to cell necrosis. The diagram set forth in the figures considers looking to hyperthermia therapy with HSP induction.

Figure 21B:
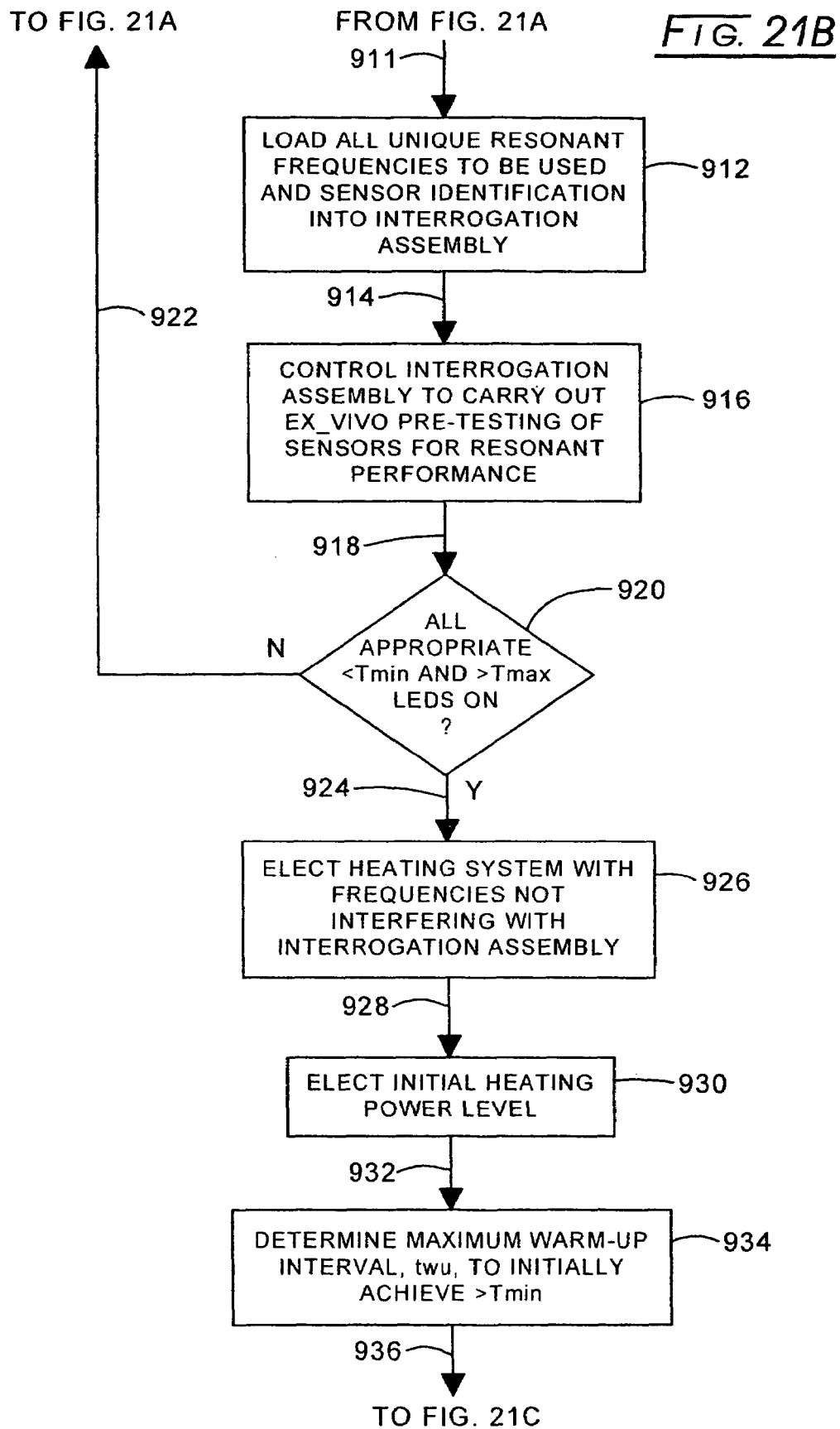
Figure 21C:
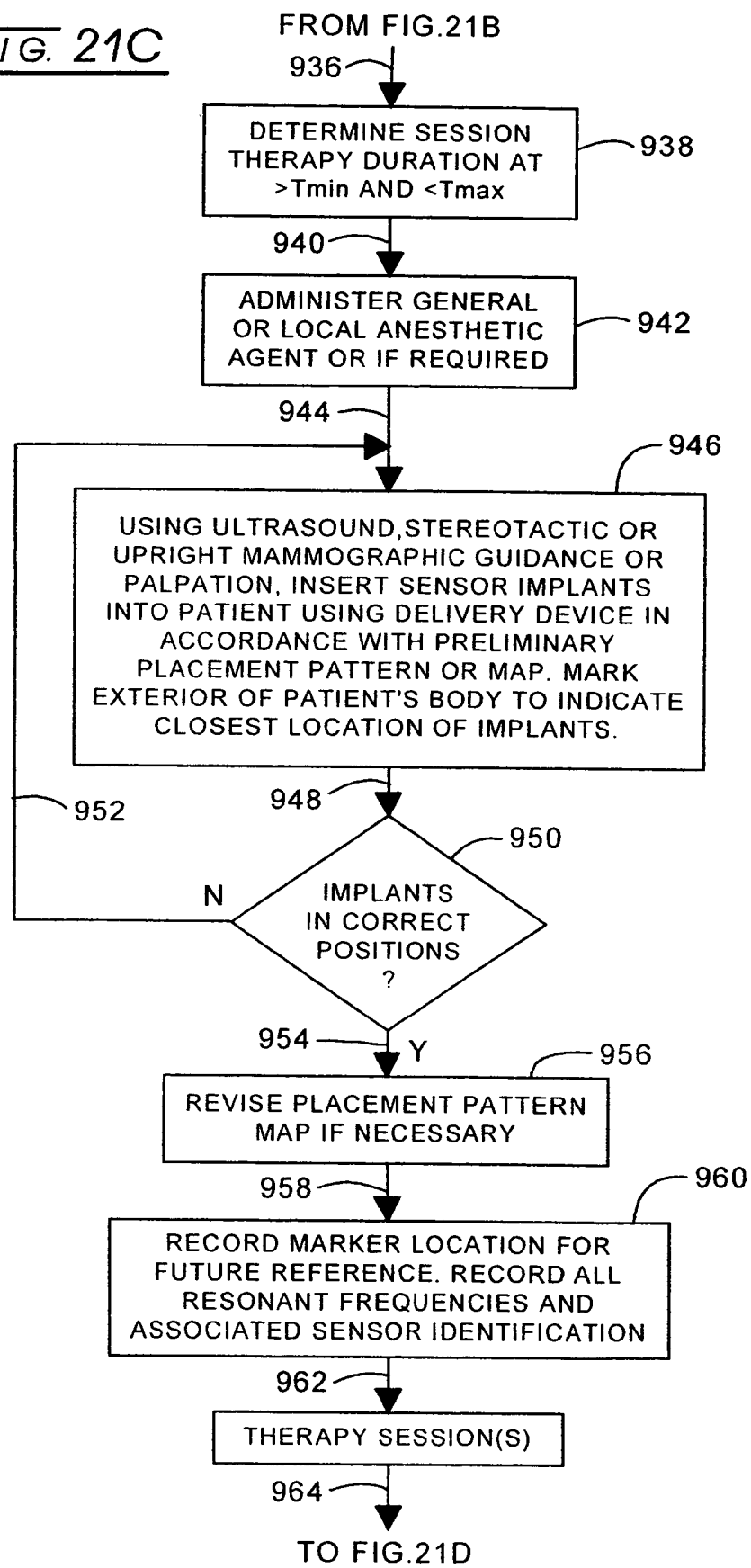
Figure 21G:
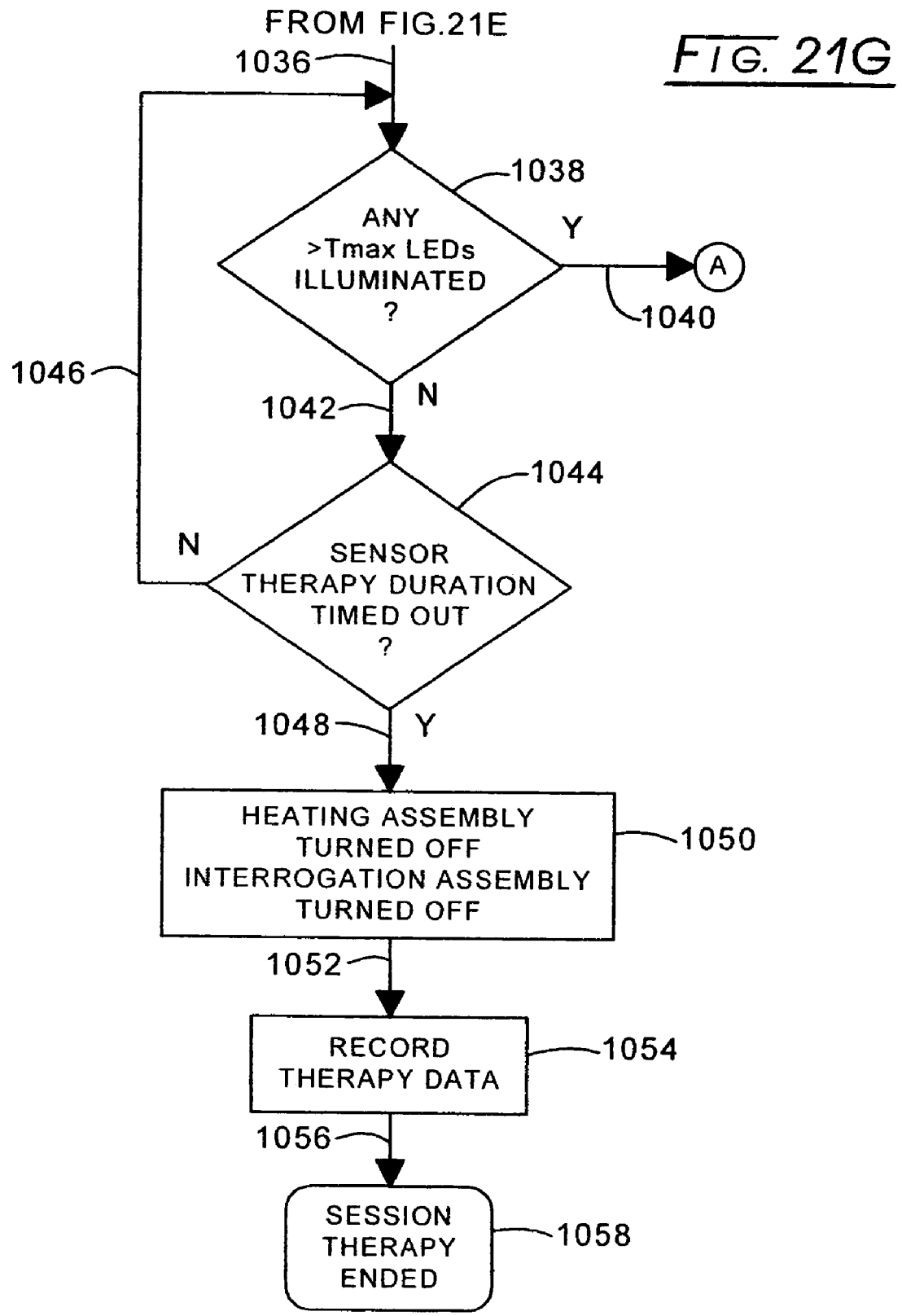

Looking to FIG. 21A, the procedure commences as represented at start node 890 and line 892 extending to block 894. Block 894 provides for the election of target therapy temperatures for hyperthermia with a consideration of HSP induction and a susceptibility to adjunct therapy such as radiation therapy or chemotherapy. Then, as represented at line 896 and block 898, implant sensors are selected based upon the thermotherapy goals. For the instant demonstration, the practitioner will consider the lower threshold temperature and the upper limit temperature levels. As represented at line 900 and block 902, the practitioner next accesses the target tissue imaging data concerning its location, size and any thermal response attributes such as the degree of vascularity which the tissue may have. With that data, as represented at line 904 and block 906 the practitioner develops a preliminary placement pattern map with an identification of the sensors with respect to their resonant center of frequency signatures. In this regard, as represented at line 908 and block 910 the temperature sensor implants are selected and compiled for ex-vivo testing assuring the presence of a unique resonant center frequency at monitoring temperatures which are temperatures considered to be below the Curie temperature of their inductor component ferrite core members. Then as represented at line 911 and block 912 (FIG. 21B) the data acquisition and control features are loaded with the resonant frequency information and numerical sensor implant identification. Those components of the control assembly are referred to as an interrogation assembly. With that data loaded, then as represented at line 914 and block 916 the control assembly or interrogation assembly is operated to carry out an ex-vivo pre-testing of the temperature sensor implants for their resonant center frequency performance. This ex-vivo testing then provides for the determination made as represented at line 918 and block 920. Harkening to FIG. 19, and assuming six lower threshold and six upper limit implants are employed, then the blue LEDs of array 834 should be illuminated as well as the yellow LEDs of array 844. In the event that one or more of these LEDs is not illuminated, then as represented by return line 922, the procedure reverts to line 908 and reselection of implant sensors.

Where the test posed at block 920 is affirmative and all implants are operational, then as represented at line 924 and block 926 a heating system is elected which performs at frequencies not interfering with the implant interrogation procedure. As represented at line 928 and block 930 an initial or starting heating level for the heating unit elected then is selected. This level may or may not be adjusted in the course of therapy. In this regard, as represented at line 932 and block 934 the practitioner determines what the maximum interval should be to reach the lower threshold temperature at the target tissue volume. This is referred to as the maximum warm-up interval, $t_{wv}$. Correspondingly, as represented at line 936 and block 938 FIG. 21C), the practitioner determines what the total therapy duration should be. In this regard, a quanta of heat energy is to be administered to the target tissue volume as determined by the intensity level of the heating unit and the duration of thermal energy application at temperatures above Tmin.

With the above basic procedures being completed, as represented at line 940 and block 942 a general or local anesthetic agent is administered and, as represented at line 944 and block 946 the practitioner employs ultrasound, stereotactic systems, upright mammographic guidance or palpation to insert the sensor implants into the target tissue volume using an appropriate delivery device as generally discussed in connection with FIGS. 16 and 17. Placement of the implants is made in accordance with the preliminary placement pattern or map. It is recommended that the skin of the patient be marked to indicate the closest location of the implants for purposes of focusing the heating unit. Following implantation, as represented at line 948 and block 950 a query is made as to whether the implants are in their correct positions. In the event that they are not, then as indicated at line 952 the procedure reverts to line 944 for purposes of carrying out correct positioning. Where the implants are in appropriate locations then as represented at line 954 and block 956 the practitioner revises the placement pattern map if necessary. Additionally, as represented at line 958 and block 960 the practitioner records the skin-carried marker location for future reference as well as records all resonant frequencies and associated sensor identification numbers with respect to the placement pattern map.

It may be recalled that these tetherless implants will remain in place indefinitely and that the patient typically will undergo several therapeutic sessions. Accordingly, it is necessary that the implant information be recorded. Thus, the next line 962 is shown leading to therapy session procedures as labeled. Each of these procedures commences as represented at line 964 extending to block 966. At block 966, the practitioner reproduces the skin-carried markers if necessary. Next, as represented at line 968 and block 970 the patient is positioned upon a treatment fixture such as a table or chair such that the skin surface carried markers are clearly visible. Then, as represented at line 972 and block 974, guided by the skin-carried marker, the practitioner positions the heating assembly output component, for example, phased array antennae as close as practical to the target tissue volume. Additionally, as represented at line 976 and block 978, again guided by the skin-carried marker, the practitioner positions the excitation and receiver or sense antennae as close as practical to the target tissue volume. In this regard, the sense antenna may be flexible and, in effect drapes over the body surface of the patient. Additionally, where necessary, as represented at line 980 and block 982 all of the recorded unique resonant center frequencies and associated sensor identification numbers are loaded into the interrogation assembly controller or data acquisition system. That interrogation controller then is turned on as represented at line 984 and block 986 and the procedure continues as represented at line 988 to the query at block 990. At this time, a determination is made as to whether all appropriate lower threshold and upper limit implants are resonating in response to monitoring or body level temperature, for example, with respect to FIG. 19 a determination is made as to whether the appropriate LEDs within array 834 are illuminated as well as the LEDs within array 844. If they are not, then as represented at line 992 and block 994 the practitioner again consults the implant map and carries out adjustments of the excite and sense antennae. The test at block 990 then is reiterated as represented at line 996 extending to line 988. Where the interrogation system is performing appropriately, then as represented at line 998 and block 1000 (FIG.

21E) the heating assembly is activated with the predetermined initial heating power level and, as represented at line 1002 and block 1004, a time-out of the maximum warm-up interval, $t_{WU}$ commences. Next, as represented at line 1006 and block 1008 a check is next made as to whether all appropriate LEDs of arrays 838 and 844 (FIG. 19) are illuminated. In the event they are not, then as represented at line 1010 and block 1012 a determination is made as to whether the maximum warm-up time has timed out. In the event that it has not, the procedure continues as represented at line 1014 to the query posed at block 1016 again determining whether the LED arrays 838 and 844 are appropriately illuminated. In the event that they are appropriately illuminated, the procedure continues as represented at line 1018.

Returning to block 1008, in the event that all appropriate LEDs of the arrays 834 and 844 are illuminated, then the procedure continues as represented at line 1020 extending to line 1018. Where the query posed at block 1012 indicates that the maximum warm-up time has been timed out, then as represented at line 1022 the program reverts to node A, which reappears in FIG. 21F. Looking to the latter figure, line 1024 extends from node A to block 1026 providing for practitioner adjustment of the heating assembly output component position and/or the heating power level. Then, as represented at line 1028 the program reverts to node B which reappears in FIG. 21E in connection with line 1030 extending to line 1006.

Returning to the query posed at block 1016, where LED array 838 indicates that the target tissue volume temperature is above the lower threshold temperature, Tmin and below the upper limit temperature as represented at LED array 846, then the program continues as shown at line 1018 to block 1034 representing the commencement of a session of a predetermined therapy duration. That therapy duration commences to be timed out. Where proper therapy temperatures are not present, the procedure reverts to node B a represented at line 1032. The program continues as represented at line 1036 leading to the query posed at block 1038 (FIG. 21G) where a determination is made as to whether any of the upper limit temperatures has been exceeded as indicated by an illumination of one or more LEDs within the LED array 848 (FIG. 19). In the event any such temperature elevation excursions have occurred, then the procedure reverts as represented at line 1040 to node A providing for the carrying out of adjustment of the heating assembly output component or components and heating power level. In the event of a negative determination with respect to the query posed at block 1038, then as represented at line 1042 and block 1044, a determination is made as to whether the therapy duration has timed out. In the event that it has not timed out, then the procedure reverts as represented at line 1046 to line 1036. Where the therapy duration has timed out, then as represented at line 1048 and block 1050 the heating assembly or unit and the interrogation assembly or controller are turned off and, as represented at line 1052 and block 1054, all therapy data are recorded and as represented at line 1056 and node 1058 the therapy session is ended. As noted above, in general, several therapy sessions will be involved in carrying out a complete treatment. The untethered nature and essentially permanent positioning of the implants beneficially facilitates the carrying out of several therapy sessions.

Where auto-regulating heater implants as described in connection with FIGS. 15 and 15A-15D, are employed as the upper temperature limit devices, then the heating units employed typically will be of an inductive variety. As a consequence, the electromagnetic energy broadcast by them will interfere with the interrogation equipment employed in accordance with the invention. Accordingly, an intermittent approach is utilized wherein the inductive heating assembly is activated for a heating interval and then turned-off, whereupon the interrogation assembly is activated. Where this intermitting is carried out automatically as opposed to the basic system of FIG. 19, then, for instance, the heating assembly may be enabled for about 100 milliseconds to about 1000 milliseconds and the interrogation assembly then is enabled for a sequential 10 milliseconds to about 100 milliseconds. This provides for almost continuous noise-free interrogation and the off interval for the heating assembly permits a modicum of accommodation for thermal inertia-based "overshoot" which may be encountered.

Figure 5:
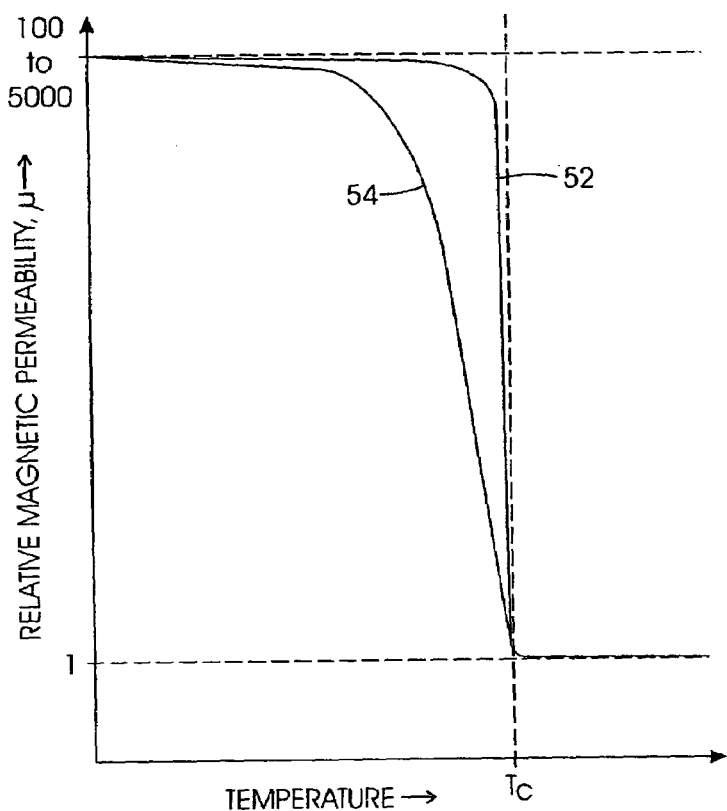
FIG. 5 shows curves relating relative permeability under low level applied magnetic field intensities and under high level applied magnetic field intensities.

A further effect of the noted inductive interference has been described in connection with FIG. 5. It may be recalled in that figure that with a high magnetic field intensity applied to the sensors or auto-regulating heaters, the Curie transition range will soften. However by intermitting, the original transition range of the sensors essentially is maintained.

Figure 22:
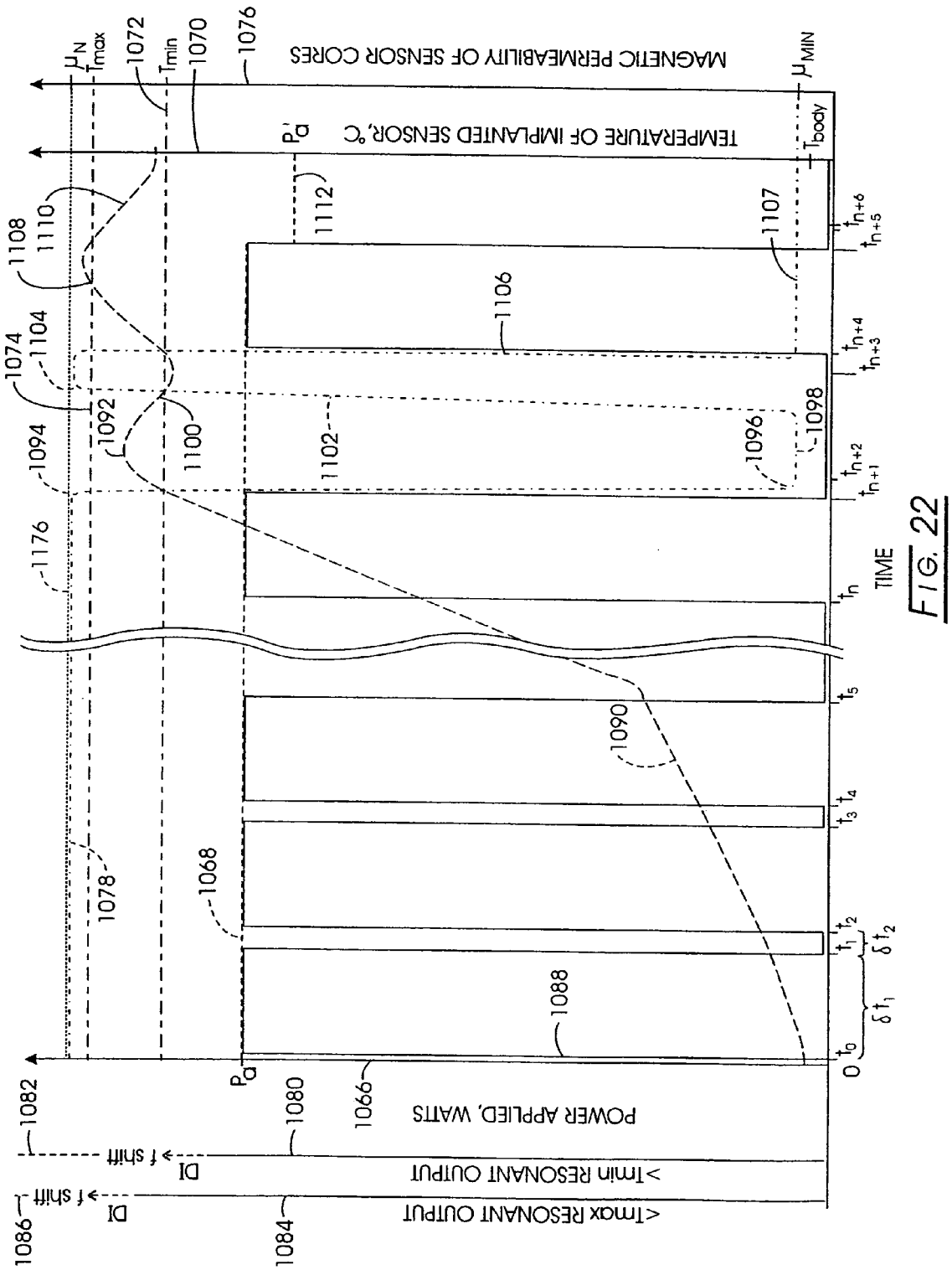
FIG. 22 is a chart illustrating an intermittent heating and interrogating feature of the system of the invention, the chart being broken along its timeline in the interest of clarity.

A graphic illustration of the intermitting performance of the system is provided in connection with FIG. 22. Referring to that figure, it may be noted that the graph is sectioned in terms of time along its abscissa, while power applied to the target tissue volume and, in particular, to the heater implant is represented along a left ordinate. The noted power is seen to be identified along ordinate 1066 as extending in value essentially from zero to an initial applied power $P_a$ at an initial power level represented at dashed line 1068. While shown in horizontal fashion, the level 1068 may vary in accordance with power adjustments. The temperature witnessed by the sensor implants and/or heater implants is shown at ordinate 1070 extending from body temperature $T_{body}$ to a lower threshold temperature, Tmin, represented at dashed line 1072 as well as to an upper limit temperature, Tmax represented at dashed line 1074. Related permeability of the core components of the implanted temperature sensors and/or implanted heaters is represented along ordinate 1075 as extending from $\mu_{MIN}$ (unity value for relative permeability) and extends to generally starting relative permeability which may fall within a substantial range, for example to values of about 100 to about 10,000. A maximum relative permeability level, $\mu_N$ for the given sensor at hand is represented at dotted horizontal line 1076, while the relative permeability of the ferromagnetic core component of the sensors or heaters is represented at dashed curve 1078. Leftward ordinate 1080 extends as an arrow having a dashed upper component representing diminished intensity, DI of the sensor output at a stable resonant center frequency as temperature approaches Curie point temperature within the Curie transition range. Recall that control is based upon the corresponding relative amplitudes. The arrow extends to lower threshold temperature, Tmin. That ordinate extends upwardly in dashed form at 1082 to represent the substantial resonant frequency shift should Curie temperature be reached for the lower threshold. Implants having a Curie temperature corresponding with the upper limit level 1074 identified as Tmax are represented at the arrow 1084 having a dashed upper component representing diminished intensity, DI of the sensor output at a stable resonant center frequency as temperature approaches Curie point temperature with the Curie transition range. Should level 1078 be reached, then the resonant frequencies of upper limit temperature sensor components will shift substantially upwardly in value as represented at dashed line 1086.

Now considering the intermittent activation or duty cycle-defined application of power and activation/enablement of the interrogation components, it may be observed that power is represented as initially being applied as shown at power curve 1088 between times $t_0$ and $t_1$, representing a power application increment of time $\delta t_1$. Following this power application interval the heating function is turned off for a sensing or interrogation time extending between times $t_1$ and $t_2$, representing an increment of measurement or sensor interrogation time, $\delta t_2$. Because the electromagnetic field applied for sensor interrogation purposes is relatively low in power, the Curie transition range characteristic elected for the sensors remains quite stable. Recall the discussion associated with FIG. 5, Note that during the intervals, $\delta t_1$ and $\delta t_2$ the temperature value of the implanted sensor as indexed along ordinate 1070 and shown at dashed curve 1090 commences to rise and is seen to exhibit a modicum of thermal inertia during interrogation interval $\delta t_2$. This power-on-power-off-interrogation sequence continues, for example, a power-on condition being applied between times $t_2$ and $t_3$ with an interrogation interval occurring between times $t_3$ and $t_4$. As these power-on and interrogation intermitting cycles continue, curve 1090 is seen to rise, eventually approaching the lower threshold temperature, Tmin at dashed horizontal line 1072. For illustrative convenience, note that the figure is broken following time $t_5$. Power is indicated as being applied during the heating interval $t_n$ to $t_{n+1}$. At the termination of that power application time interval, tn+1, lower threshold Curie temperature is approached or achieved at the implant sensor inductor core component and may produce a slight thermal overshoot at 1092 within the acceptable range of temperatures between dashed lines 1072 and 1074. Note, as this occurs, that a permeability curve for the lower threshold sensor implants at knee 1094 change of state is experienced and the relative permeability of the implanted sensor component for this lower threshold drops dramatically essentially to a unity value as represented at curve 1078 inflection point 1096 occurring at time $t_{n+2}$. Under the ensuing time element, unless the temperature being sensed by the lower threshold devices drops, for example, below the lower threshold at dashed line 1072, the relative permeability of the core of the sensor will remain at a unity level as represented at 1098. Should the temperature being sensed by the lower threshold component drop in temperature below the lower threshold at dashed line 1072 as represented at point 1100, then as shown at permeability curve portion 1102, relative permeability abruptly rises, for example, to level 1104. Should the lower threshold temperature sensor again experience a drop in temperature below the threshold level 1072 then as represented at curve portion 1106 relative permeability again will abruptly change toward unity. Assuming that the temperature remains elevated, the unity value for relative permeability for the lower threshold sensor components will remain at a unity level as represented at curve portion 1107. Should the heating unit cause the target tissue volume approach or to exceed the upper limit temperature Tmax as represented at point 1108 then a power adjustment is called for to return the temperature to its proper range as represented at curve portion 1110. This results in a lowering of the power applied, Pa', as represented at dashed level 1112.

Figure 23C:
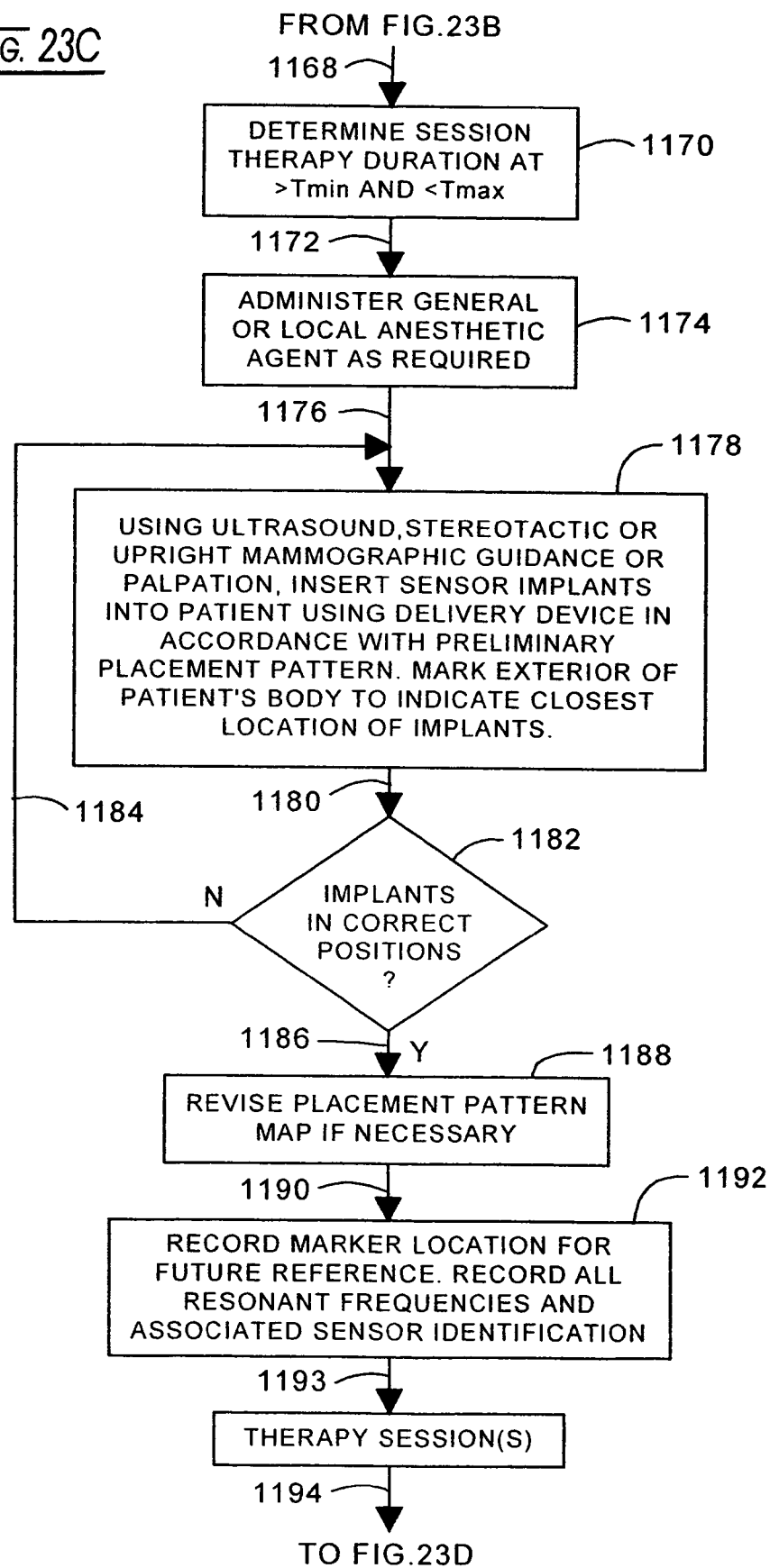

Referring to FIGS. 23A-23H a procedural block diagram is presented detailing the activities undertaken with the intermittent operation of the system as discussed in connection with FIG. 22. Looking to FIG. 23A, the procedure commences as represented at node 1120 and line 1122 extending to block 1124. As before, the practitioner elects the target therapy temperatures, for example, for hyperthermia and a consideration of HSP induction as well as susceptibility to adjunct therapies. Next, as represented at line 1126 and block 1128 the implants are selected for the target therapy temperatures. As before, the practitioner will consider a lower threshold based temperature sensing device as well as an upper limit based device. As represented at line 1130 and block 1132, the practitioner accesses target tissue imaging data concerning the location size and thermal response attributes of the target tissue volume. With that information, as represented at line 1134 and block 1136 the practitioner develops a preliminary implant placement pattern map with an identification of the sensors and/or auto-regulating heater implants. This map having been selected, as represented at line 1138 and block 1140 the practitioner selects and compiles the sensors such as the lower threshold temperature sensors and any upper limit temperature sensor implants to be employed. Ex-vivo testing is carried out of the temperature sensing implants to determine that they are indeed developing the appropriate resonant center frequencies at monitoring temperatures below associated Curie point temperature. Next, as represented in FIG. 23B at line 1142 and block 1144 the interrogation assembly or data acquisition components are loaded with the unique resonant center frequencies involved and the associated sensor implant identifications. Next, a testing of the temperature sensor implants is carried out as represented at line 1146 and block 1148. This test determines whether the appropriate resonant center frequencies are detected at room temperature. That determination is represented at line 1150 and the query posed at block 1152. In effect, the test determines whether the appropriate LEDs of arrays of 834 and 844 are illuminated as described in connection with FIG. 19. In the event one or more of these LEDs is not illuminated, then as represented at line 1154 the procedure reverts to line 1138. Where all temperature sensor implants are performing at room temperature, then as represented at line 1156 and block 1158 an alternating current (ACF) field heating system, for example, an inductive system is elected and as represented at line 1160 and block 1162 an initial power level is selected for the heating system. Next, as represented at line 1164 and block 1166 the practitioner determines the maximum warm-up interval, $t_{WU}$ for initially achieving the lower threshold minimum temperature, Tmin. The practitioner then determines the therapy session duration at temperatures above the lower threshold and below the upper limit as represented at line 1168 and block 1170 (FIG. 23C). With this accomplished, as represented at line 1172 and block 1174 a general or local anesthetic agent is administered to the patient and, as set forth at line 1176 and block 1178, the target tissue volume is analyzed using such modalities as ultrasound, sterotactic, or upright mammographic guidance or palpation. The temperature sensor implants are located as well as any auto-regulating heater implants at the target tissue volume in accordance with a preliminary placement pattern or map. Further, the skin surface of the patient's body is marked to identify the implant locations. As represented at line 1180 and block 1182 a determination is made as to whether the implants are in the proper location. If an implant is not properly located, then as represented at line 1184 the procedure reverts to line 1176. With the implants being properly located, then as represented at line 1186 and block 1188 any revisions to the implant pattern map are carried out and the program continues as represented at line 1190 and block 1192 where the skin carried marker location is recorded for future reference and all resonant frequencies and associated sensor identification numbers further are recorded.

As then labeled in conjunction with at line 1193, one or more therapy sessions are carried out. As noted above, inasmuch as the sensors are untethered and essentially permanently implanted, multiple therapy sessions can be carried out without a requirement for re-implanting such devices. As multiple therapy sessions are carried out, the skin carried marker may somewhat disappear. Accordingly, lines 1193 and 1194 extend to block 1195 (FIG. 23C) calling for the reproduction of the marker if necessary. Line 1196 and block 1198 provide for the positioning of the patient on a table or chair such that the marker is clearly visible and properly oriented. That marker, then as represented at line 1200 and block 1202, is utilized in positioning the heating assembly output component with respect to the target tissue volume. Additionally, as represented at line 1204 and block 1206 the interrogation assembly excitation and receiver or sense antennae are appropriately positioned. As noted above, the sense or receiver antenna is configured as being flexible and in effect drapes across the patient's body. From block 1206, as represented at line 1208 and block 1210 if not carried out beforehand, the practitioner loads all unique resonant center frequencies into the interrogation assembly controller. Then, as represented at line 1212 and block 1214 a test of the interrogation system is carried out by initially turning on the interrogation assembly controller and carrying out excite and sense cycles as represented at line 1216 and block 1218. A determination then is made as to whether all appropriate LEDs within arrays 834 and 844 as described in conjunction with FIG. 19 are illuminated. In the event that they are not so illuminated, then as represented at line 1220 and block 1222 the practitioner consults the implant placement map and adjusts the interrogation antennae appropriately. The procedure then returns to line 1216 as represented at line 1224. Where all appropriate LEDs have been illuminated, the procedure continues as represented at FIG. 23E and line 1226 and block 1228 providing for the actuation of the heating assembly with the initial heating ACF power level for a heating period. At the same time, as represented at line 1230 and block 1232 timing is commenced with respect to the warm-up time, $t_{WU}$. At the termination of the heating period, as represented at line 1234 and block 1236 the heating assembly is turned off and as provided at line 1238 and block 1240 the interrogation controller is activated with the generation of the earlier-described excite and acquire signal activities. These activities are carried out for an interrogation interval and following that interval as represented at line 1242 and block 1244 a query is made as to whether the lower threshold LED array 838 and upper limit LED array as at 844 (FIG. 19) are illuminated to represent that the therapeutic temperature range has been reached. In the event of a negative determination to this query, then as represented at line 1246 and block 1248 a determination is made as to whether the warm-up time, $t_{WU}$ has timed out. In the event that it has not timed out, then as represented at line 1250 and block 1252 the query posed at block 1244 is reiterated. Where these LED arrays are illuminated, the procedure continues as represented at line 1254. On the other hand, where all of the noted LEDs are not illuminated then the procedure continues as represented at line 1256 and node A. Note additionally, that in the event that the warm-up time, $t_{WU}$ indeed has timed out in connection with the query at block 1248, then the procedure also extends as represented at line 1258 to node A.

Looking momentarily to FIG. 23F, node A reappears in conjunction with line 1260 extending to block 1262 providing for manually adjusting the heating assembly output component position and/or the heating power level. Next, as represented at line 1264 and block 1266, the heating assembly is turned on for the noted heating period. As represented at line 1268, the procedure then extends to node B. Node B reappears in FIG. 23E in connection with line 1270 extending to earlier described block 1236 providing for turning off the heating unit power following the heating period.

In the event of an affirmative determination with respect to the query posed at block 1252, then as represented at line 1254 and block 1272 the session therapy duration time-out commences. Where the query at block 1244 indicates that all appropriate LEDs are illuminated, the procedure extends as represented at line 1274 to line 1254. With the commencement of therapy duration time-out, as represented at line 1276 and block 1278 the interrogation assembly is turned off and as represented at line 1280 and block 1282 (FIG. 23H) intermitting continues with the turning on of the heating assembly for the heating period. At the termination of that heating period, as represented at line 1284 and block 1286 the heating assembly is turned off and as represented at line 1288 and block 1290 the interrogation assembly again is activated. The procedure then continues as represented at line 1292 to the query posed at block 1294. Block 1294 questions whether any of the LEDs representing a temperature excursion above the upper limit have been illuminated, for example, the illumination of any of the LEDs of array 848 described in connection with FIG. 19. In the event of an affirmative determination, then as represented at line 1296 the procedure reverts to node C. Looking momentarily to FIG. 23H, node C reappears in connection with line 1298 extending to block 1300 providing for turning off the heating unit. Upon the heating unit being turned off, as represented at line 1302 and block 1304. The interrogation assembly is activated and as represented at line 1306 the procedure reverts to node D.

Node D reappears in conjunction with line 1308 in FIG. 23G. In this regard line 1308 extends to line 1292 and the query at block 1294. Where none of the LEDs of array 848 (FIG. 19) are illuminated, then as represented at line 1310 the procedure carries out the query posed at block 1312. At block 1312 a determination is made as to whether the therapy duration has timed out. In the event that it has not, then the procedure loops as represented at line 1314 to line 1280. Where a therapy duration has timed out, then as represented at line 1316 and block 1318 both the heating assembly and interrogation assembly are turned off and, as represented at line 1320 and block 1322 therapy data are recorded and as represented at line 1324 and node 1326 the therapy session is ended.

Figure 24B:
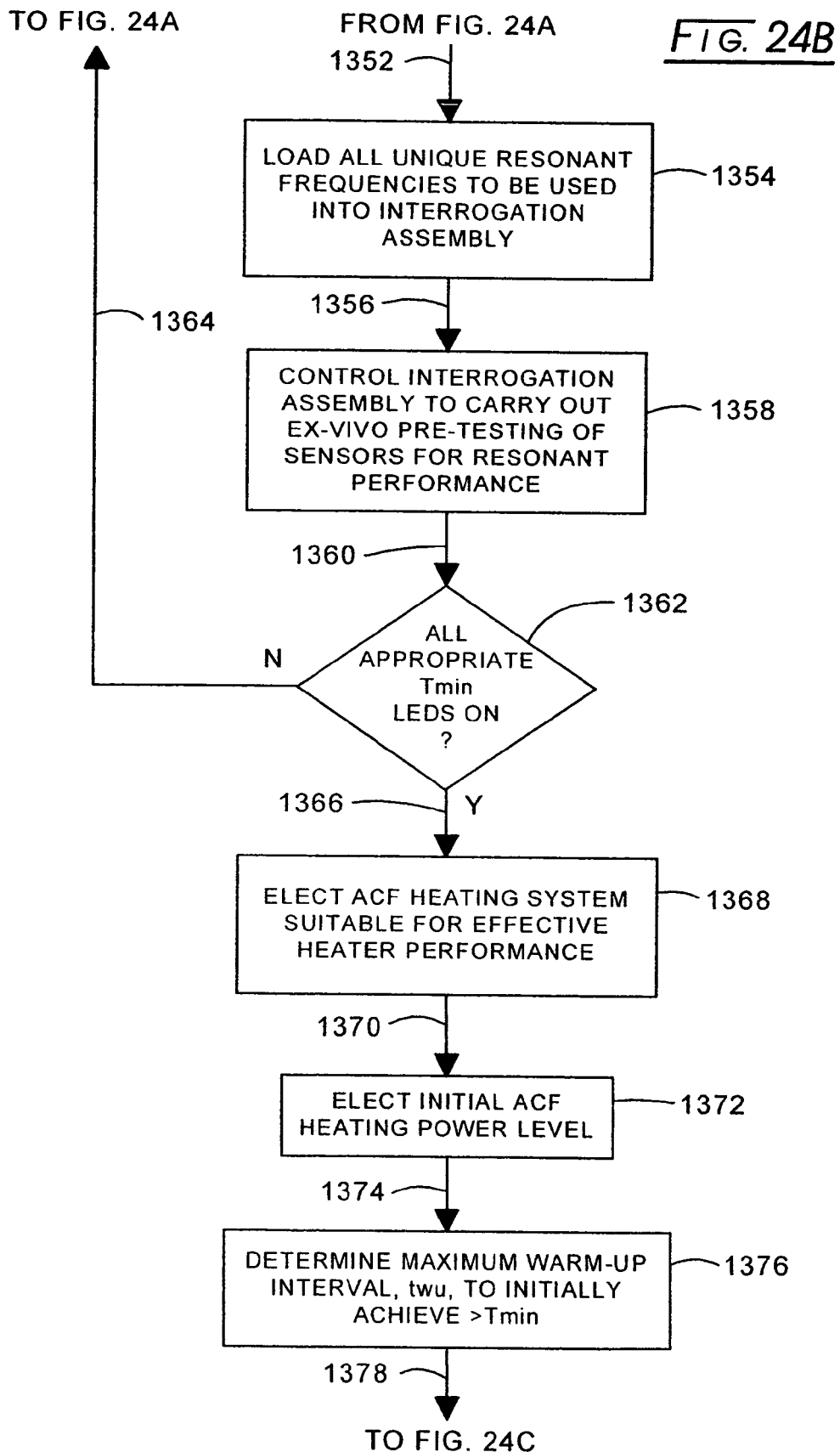
Figure 24C:
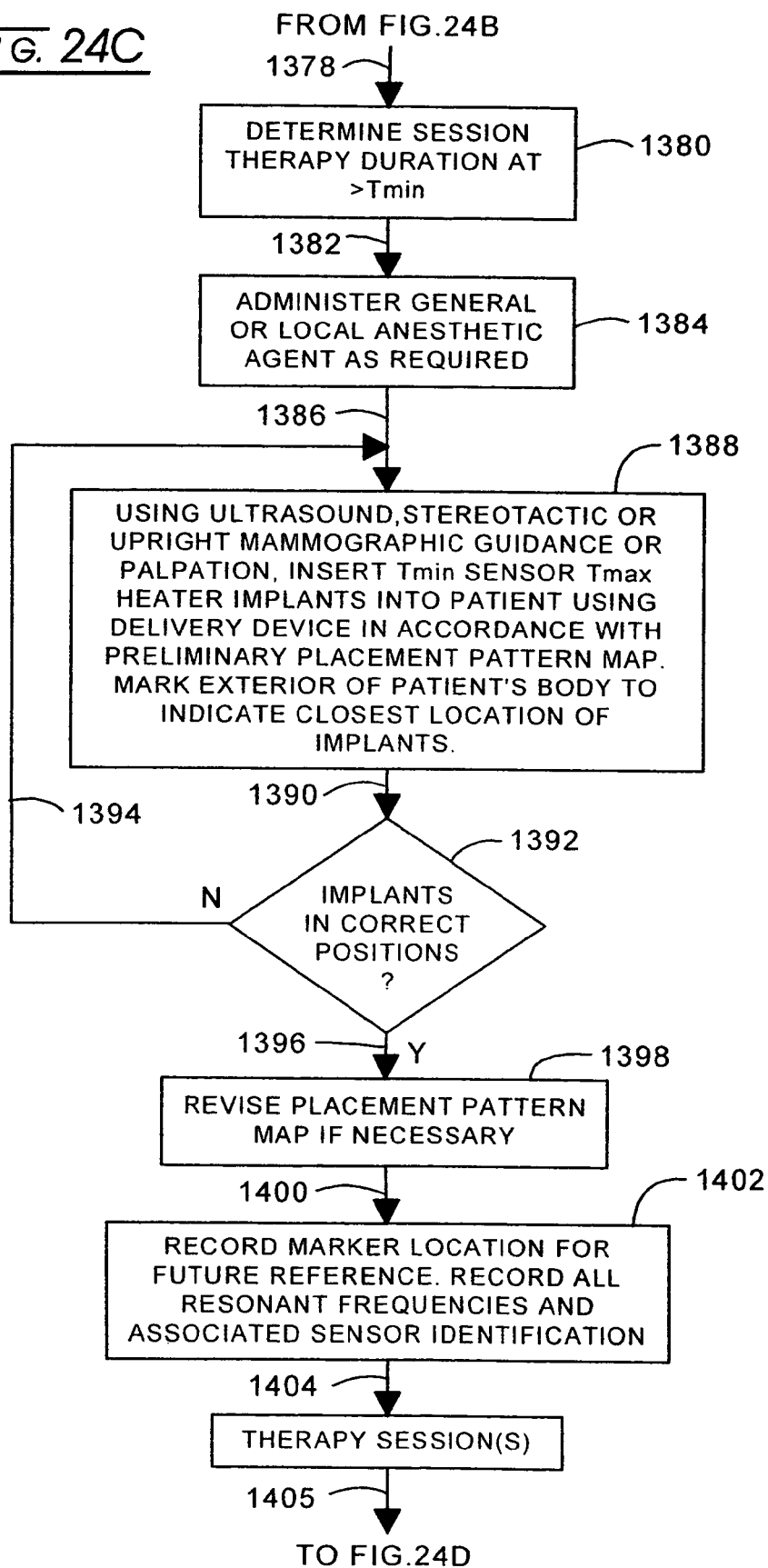

The intermitting approach also can be employed with temperature sensor implants which respond to identify a lower temperature threshold and upper limit temperature heater implants as described earlier in connection with FIGS. 15 and 15A-15D. Inasmuch as the heater implants typically will require an inductive form of alternating field current excitation, intermitting is called for to both avoid interference with the interrogation procedure. The procedure for carrying out this intermitting approach with this combination of implants is provided in connection with FIGS. 24A-24G. Looking to those figures, a procedure commences with start node 1330 and line 1332 extending to block 1334. At block 1334, the practitioner elects target temperatures for thermotherapy and susceptibility to adjunct therapy such as radiation therapy or chemotherapy. Those target temperatures will involve the noted lower threshold sensed temperature and the upper limit auto-regulating heater temperature. Next, as represented at line 1336 and block 1338 the implant sensors with lower threshold temperatures are selected as well as the auto-regulating heater implants with regulation to the upper limit temperature. Then, as represented at line 1340 and block 1342 target tissue imaging data is accessed, such data concerning location, size and thermal response attributes of the target tissue volume. As represented at line 1344 and block 1346 the practitioner develops a preliminary placement pattern map for the heater implants and temperature sensor implants within the identified target tissue volume. Upon developing this map, as represented at line 1348 and block 1350 the lower threshold temperature sensing implants are selected and compiled for ex-vivo testing with respect to room temperature. Additionally, as represented at line 1352 and block 1354 the unique resonant center frequencies to be used with respect to the lower threshold sensor implants are loaded into the interrogation assembly and, as represented at line 1356 and block 1358 the interrogation assembly is controlled to carry out the ex-vivo pre-testing of the lower threshold sensor implants. This test results in the illumination of appropriate LEDs. In this regard, line 1360 extends from block 1358 to block 1362 wherein the question is posed as to whether all appropriate Tmin LEDs are on. Those LEDs will be, for example, within the array 834 described in conjunction with FIG. 19. In the event that the appropriate LEDs are not on, then as represented at line 1364 the procedure reverts to line 1348. Where all appropriate lower threshold temperature LEDS have been illuminated, then as represented at line 1366 and block 1368 an ACF heating system is elected which is suitable for performance with the auto-regulating heater implants. Such a system typically will be an inductive one. Upon electing the ACF heating system, then as represented at line 1370 and block 1372 the initial ACF heating power level is selected. With that selection, as represented at line 1374 and block 1376 a maximum warm-up interval to initially achieve the lower threshold temperature is determined. As represented at line 1378 and block 1380 (FIG. 24C) a determination is made as to the length of the session therapy while the target volume is at or above the lower threshold temperature. With that determination, as represented at line 1382 and block 1384 a general or local anesthetic agent is administered and the temperature sensing implants and heater implants are located within the target tissue volume as represented at line 1386 and block 1388. The positioning of the implants is carried out using ultrasound, stereotactic or upright mammographic guidance or palpation. Additionally, the patient's skin or the exterior of the patient's body is marked to indicate the closest location of the implants. As represented at line 1390 and block 1392 a determination is made as to whether the implants are in correct positions. In the event they are not, then the procedure loops as represented at line 1394 to line 1386. Where a determination is made that the implants are in their correct positions, then as represented at line 1396 and block 1398 a revision of the placement pattern map is made if it is necessary. Next, as represented at line 1400 and block 1402 the marker location is recorded for future reference as well as all resonant frequencies and associated lower threshold sensor identifications. As labeled in conjunction with line 1404 the patient is now prepared to undergo a number of therapy sessions. Lines 1404 and 1405 extend to block 1406 (FIG. 24D) providing for the reproduction of the marker if necessary. Next, as represented at line 1408 and block 1410 the patient is positioned on the support such that the marker on the patient's skin is clearly observable and the target tissue volume is accessible to heating and interrogation procedures. Next, as represented at line 1412 and block 1414 the heating assembly output component is positioned as close as practical to the target tissue volume. Additionally, as represented at line 1416 and block 1418 the excitation and sense or receiving antennae are located with respect to the target tissue volume. If not accomplished earlier, as represented at line 1420 and block 1422 all of the unique resonant frequencies and lower threshold temperature implant identifiers are loaded into the interrogation assembly. Next, as represented at line 1424 and block 1426 the interrogation assembly controller is turned on and a performance of the lower threshold temperature sensor implants is evaluated as represented at line 1428 and block 1430. At block 1430 a determination is made as to whether the appropriate lower threshold LEDs are illuminated. Those LEDs were described in connection with FIG. 19 at array 834. In the event certain or all of those appropriate LEDs are not illuminated, then as represented at line 1432 and block 1434 the practitioner consults the implant placement map and adjusts the excite and/or sense antennae as appropriate and the procedure returns as represented at line 1436 to line 1428. Where all appropriate LEDs have been illuminated, as represented at line 1438 and block 1440 (FIG. 24E) the heating assembly is actuated with initial alternating current field heating power for a heating period. As the heating assembly is activated, as represented at line 1442 and block 1444 timing is commenced for the time to warm-up and the procedure continues as represented at line 1446 extending to block 1448. Block 1448 provides for turning off the heating assembly power, whereupon as represented at line 1450 and block 1452 the controller/interrogation assembly is turned on to carry out the excite and acquire functions. Based upon that interrogation, as represented at line 1454 and block 1456 a determination is made as to whether the lower threshold heating level has been reached as determined by the illumination of appropriate ones of LED array 838 (FIG. 19). Where all appropriate such LEDs are not illuminated, then as represented at line 1458 and block 1460 a determination is made as to whether the warm-up time interval has timed out. If it has not, then as represented at line 1462 and block 1464 the query posed at block 1456 is reasserted. Where all appropriate LEDs have been illuminated the procedure continues as represented at line 1466 and block 1468 providing for the timing out of the session therapy duration. Returning to block 1456 where all appropriate LEDs have been illuminated, then the procedure continues as represented at line 1470 to line 1466. Where the determination at block 1460 is that the warm-up time interval has expired, then as represented at line 1472 the procedure reverts to node A. Similarly, where the determination at block 1464 is that all appropriate LEDs have not been illuminated the program reverts to node A as represented at line 1474.

Looking momentarily to FIG. 24F node A reappears in conjunction with line 1476 extending to block 1478. Block 1478 provides for the manual adjustment of the heating assembly output component and/or heating power level. Additionally, as represented at line 1480 and block 1482 the heating assembly power is turned on for a heating period and the program continues as represented at line 1484 and node B.

Returning to FIG. 24E, node B reappears with line 1486 extending to line 1446.

Figure 24G:
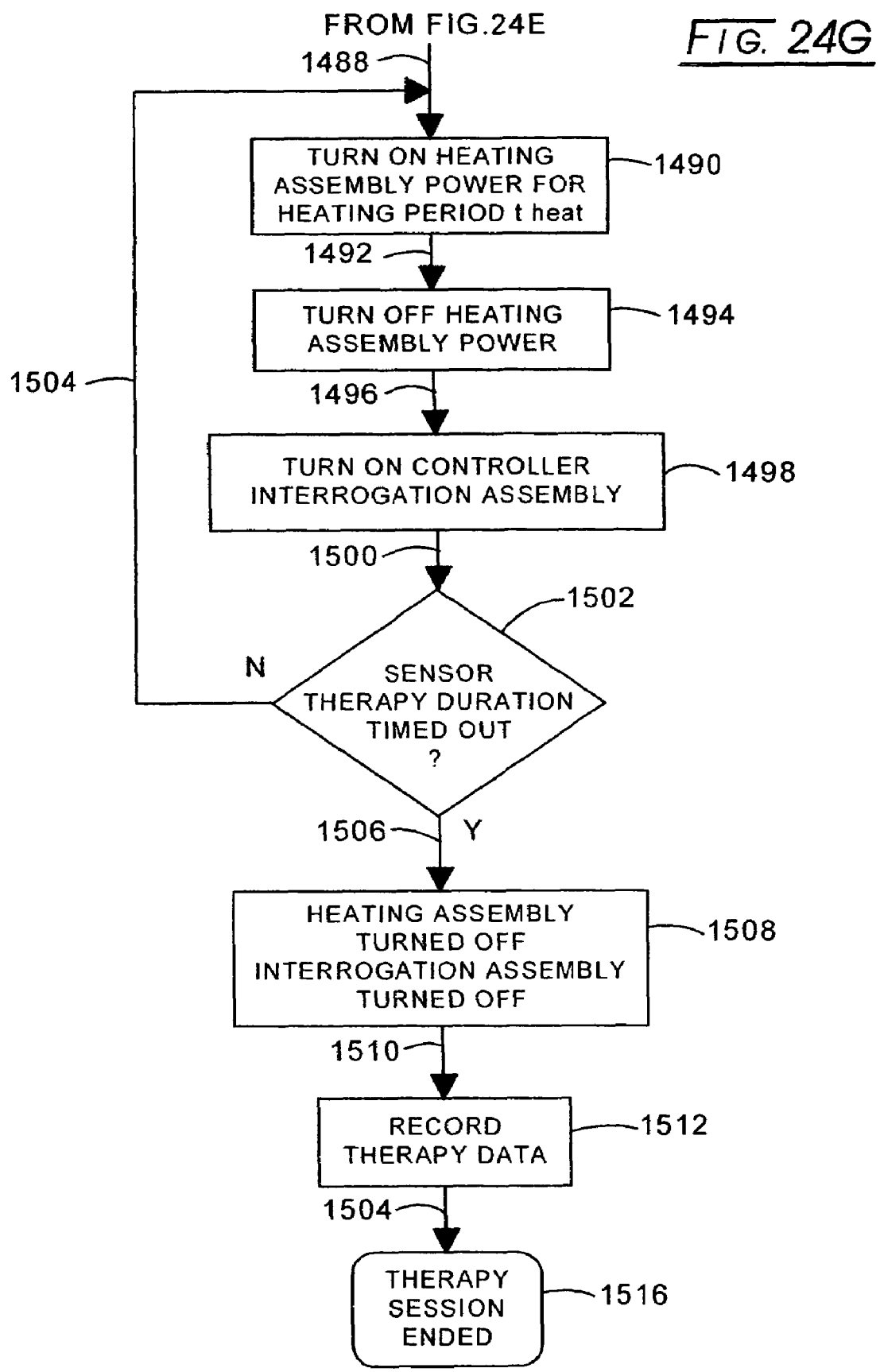

With the commencement of session therapy duration timeout as represented at block 1468, the procedure turns on the heating assembly for the noted heating period as represented at line 1488 and block 1490 (FIG. 24G). Following the heating period, as represented at line 1492 and block 1494 the heating assembly is turned off and as represented at line 1496 and block 1498 the controller/interrogation assembly is turned on. The procedure then queries as to whether the session therapy duration has timed out as represented at line 1500 and block 1502. Where that is not the case, then as represented at line 1504 the procedure reverts to line 1488. However, where the session therapy has timed out, then as represented at line 1506 and block 1508 the heating assembly and the interrogation assembly are turned off and, as represented at line 1510 and block 1512 therapy data are recorded. With such recordation, as represented at line 1514 and node 1516 the therapy session is ended.

Figure 25:
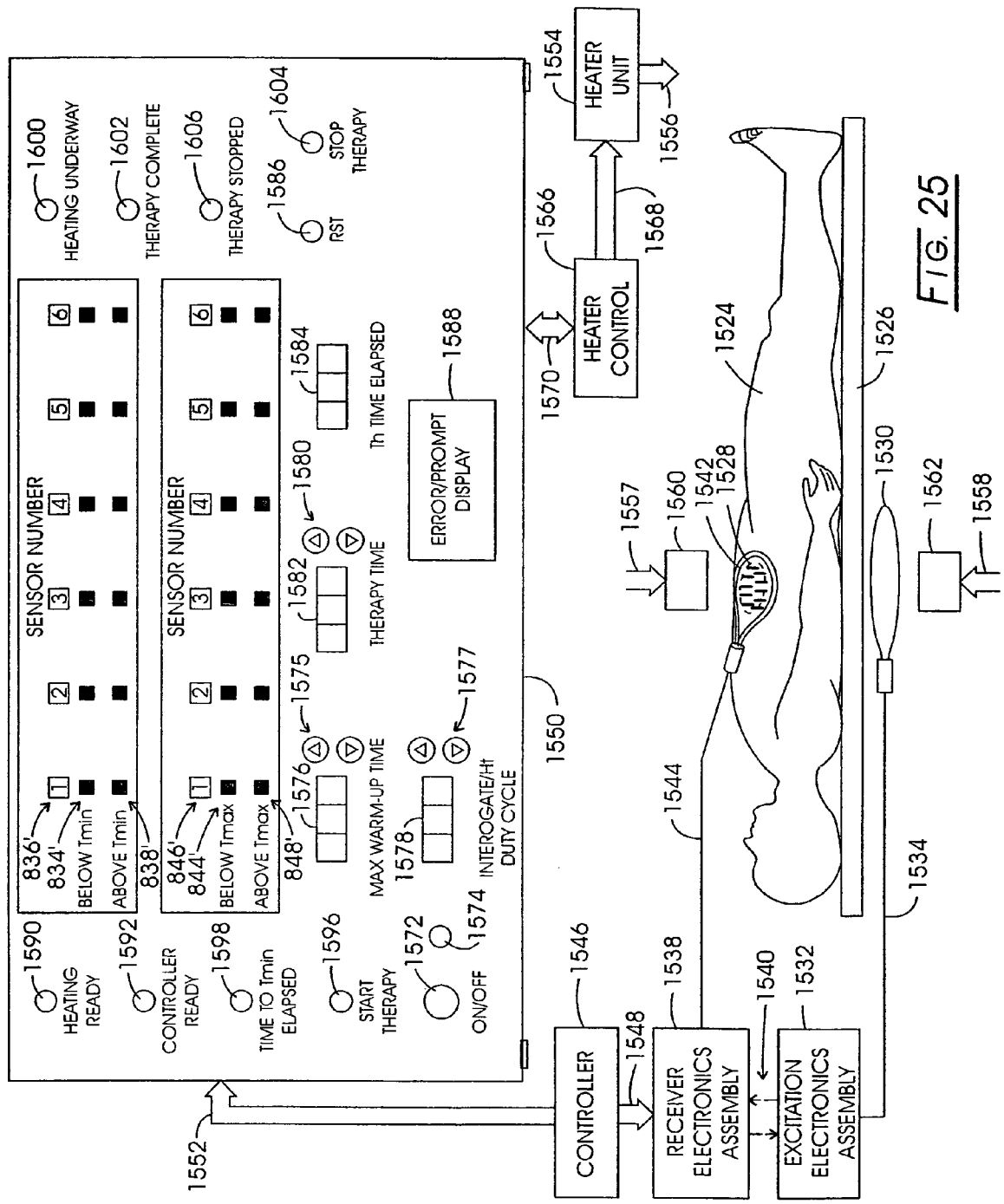
FIG. 25 is a schematic representation of another embodiment of the system of the invention.

Referring to FIG. 25 the system at hand is illustrated in connection with a controller exhibiting more elaborate interface features. Looking to the figure, the patient reappears at 1524 supine upon a support or table 1526 and the target tissue volume is represented at 1528. An excitation antenna 1530 is located beneath patient 1524 in the vicinity of target tissue volume 1528. Antenna 1538 is operatively associated with the excitation electronics assembly represented at block 1532 by a cable 1534. Assembly 1532, in turn, is interactively associated with a receiver electronics assembly represented at block 1538 by an opto-isolated coupling represented at arrows 1540. Receiver assembly 1538 is coupled with a sense antenna 1542 by cable 1544. As before, antenna 1542 may be flexible and draped upon the surface of the patient 1524 in the vicinity of target tissue volume 1528. A controller is represented at block 1546 which is operatively associated with receiver assembly 1538 and excitation electronics assembly 1532 as represented by arrow 1548 and the controller is interactively coupled with a control console 1550 as represented at arrow 1552. A heater unit is represented at block 1554 having an output represented at arrows 1556-1558 extending to output components 1560 and 1562. Heater unit 1554 is controlled from a heater control assembly as represented at arrow 1564, block 1566 and arrow 1568. Control 1566 is operatively associated with the console 1550 as represented by arrow 1570.

Console 1550 incorporates LED arrays as have been earlier-described in connection with FIG. 19. Accordingly, those arrays as well as their associated implant identifications are shown with the same numerical representation but in primed fashion. An on/off switch is represented at 1572 in combination with an on/off indicator LED 1574. Maximum warm-up time is inserted by the operator into the system with up-down switches 1575 in association with a time read-out 1576. Where an intermitting type interrogate/heat operation is employed, the corresponding duty cycle is loaded into the system by actuation of up-down switches 1577 in conjunction with read-out 1578. Total therapy time also is inserted with up-down switches 1580 which are operated in association with read-out 1582. A read-out 1584 provides the operator with data as to the therapy time elapsed. Read-out 1584 may be reset at reset switch 1586 and an error/prompt display is provided at 1588. A heater unit ready green LED is provided at 1590 and a corresponding controller ready green LED cueing device is represented at 1592. Therapy is started by actuating switch 1596 and the time to reach the lower threshold temperature level elapsing is represented by red LED cueing output 1598. At such time as that lower threshold of heating has been achieved, therapy timing is commenced with a green LED based cue 1600. As LED 1600 is illuminated, therapy time elapsed information at read-out 1584 is actuated. At such time as the therapy time elapsed 1584 is equivalent to the therapy time 1582, an LED cue is provided by green LED 1602 indicating that therapy is complete. In the course of therapy, the practitioner may wish to stop the therapy. Accordingly, a stop therapy switch 1604 is provided with an associated red LED cue representing a stop therapy condition at 1606.

Figure 26C:
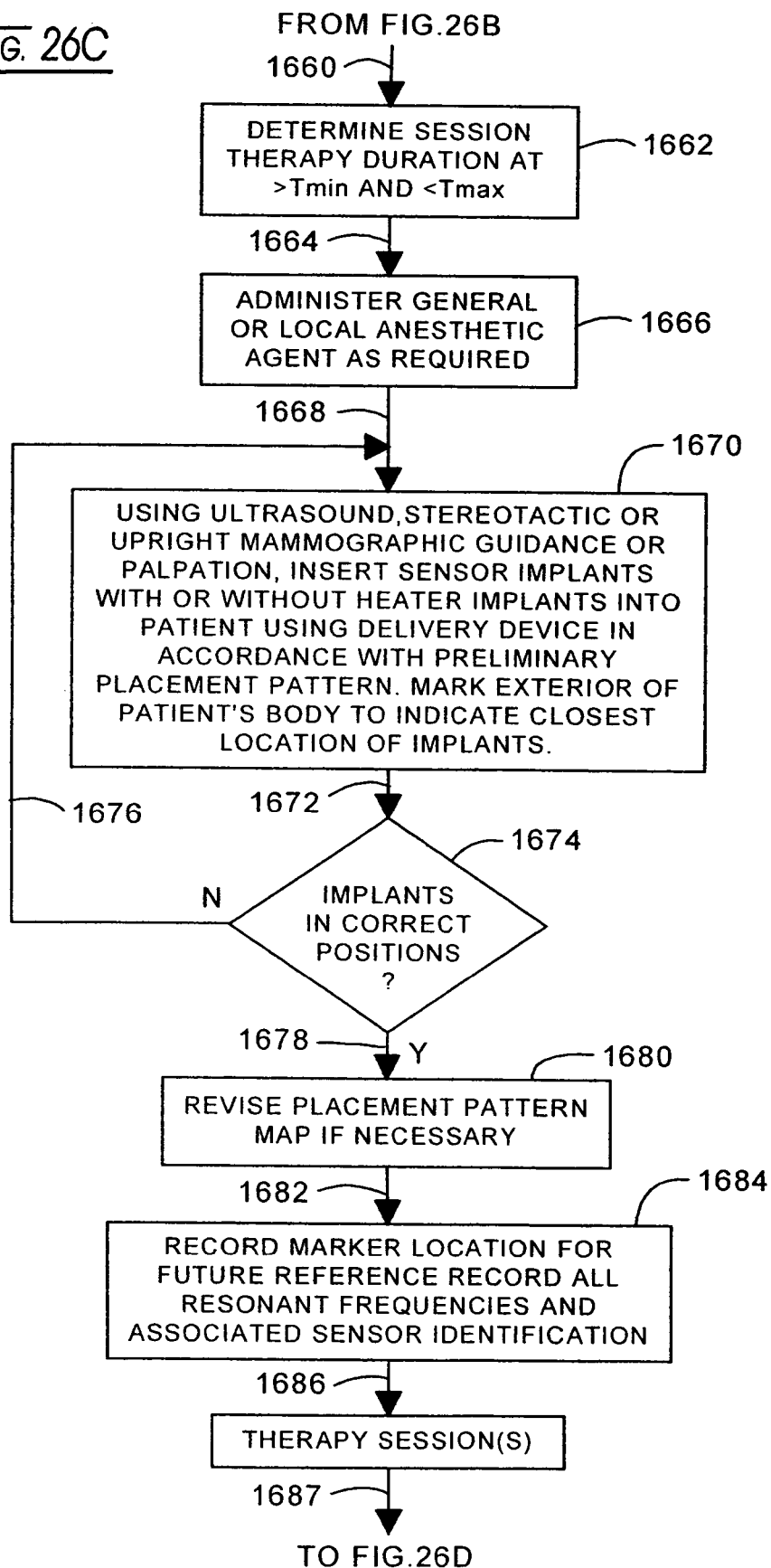
Figure 26E:
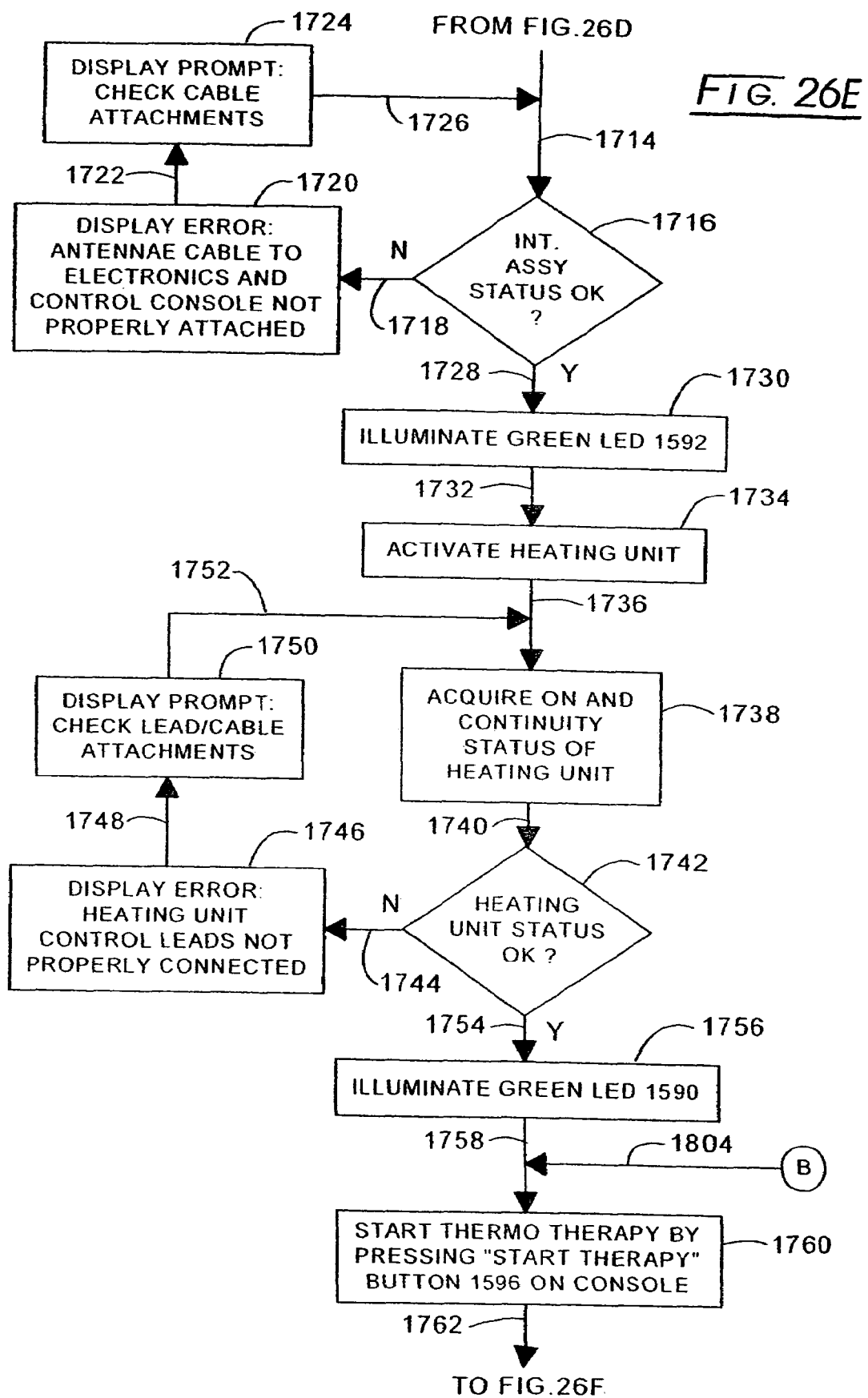
Figure 26G:
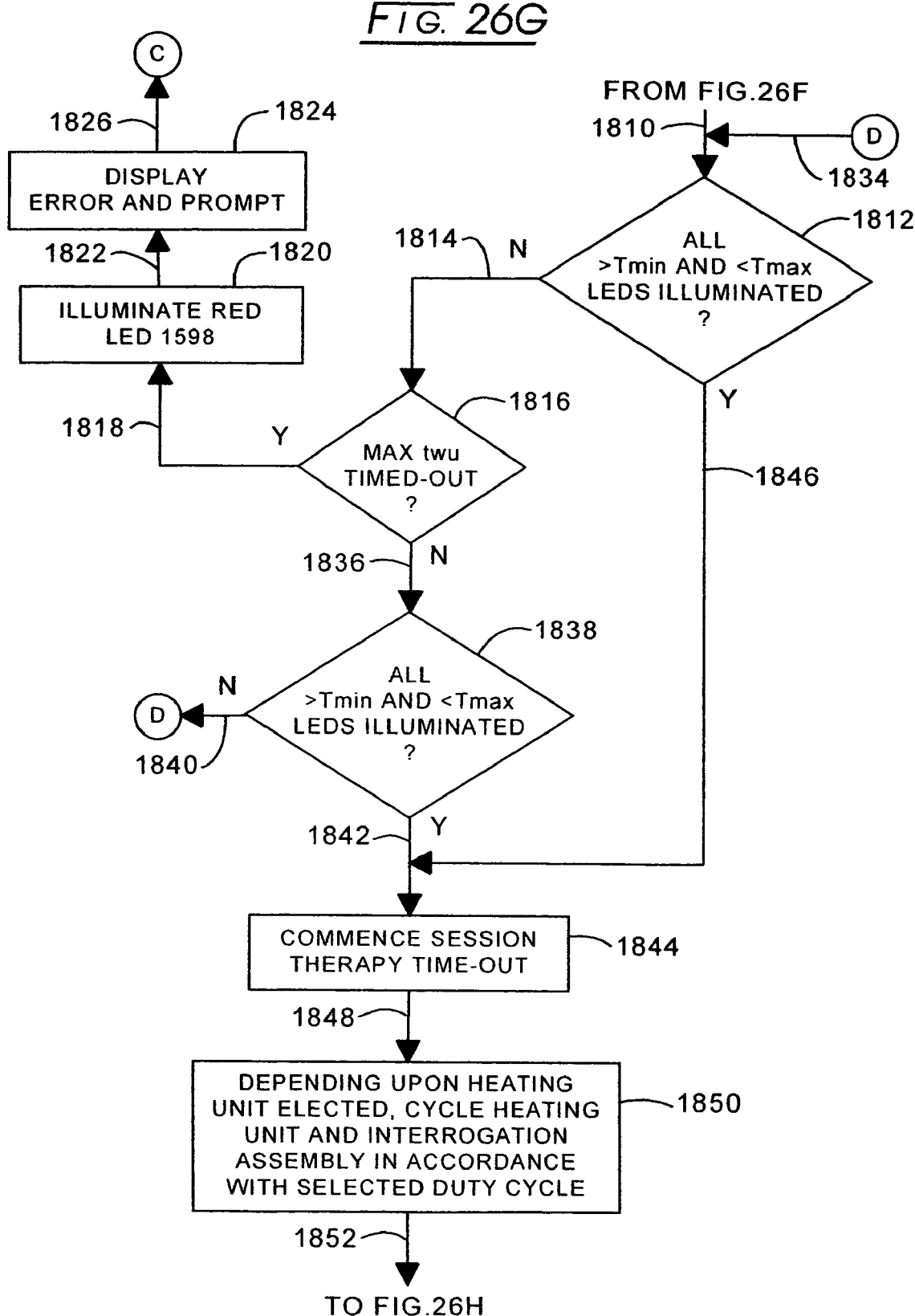

Referring to FIGS. 26A-26J the procedure associated with the enhanced system of FIG. 25 is set forth in block diagrammatic fashion. In FIG. 26A, the procedure is shown to start at node 1612 and line 1614 extending to block 1616. Block 1616 provides for the election of the target therapy temperatures, for example for hyperthermia with a consideration of HSP induction as well as adjunct therapies. Following this election, as represented at line 1618 and block 1620, implant sensors are selected based upon the target therapy temperatures. As before, this selection may include lower threshold temperature based implants and upper limit temperature based implants. As represented at line 1622 and block 1624 the practitioner accesses target tissue imaging data with respect to its location, size and thermo response attributes. With that data at hand, then as represented at line 1626 and block 1628 an implant placement pattern map is developed with the identification of sensors and their proposed location within the target tissue volume. Next, as represented at line 1630 and block 1632 the sensor implants to be utilized are selected and compiled for ex-vivo testing. For this purpose, as represented at lines 1634 and block 1636 (FIG. 26B) the unique resonant center frequencies and identification of the sensor implants is loaded into the control system. The ex-vivo test then is carried out as represented at line 1638 and block 1640. As represented at line 1642 and block 1644 a test is carried out to determine that the appropriate LEDs within arrays 834' and 844' are illuminated. In the event the test fails, the procedure reverts as represented at line 1646 to line 1630. With an affirmative response to the query posed at block 1644, then as represented at line 1648 and block 1650 a heating system may be elected with frequencies not interfering with the interrogation assembly. Where such interference may occur, then the intermittent form of operation of the system is called for. Next, as represented at line 1652 and block 1654 the practitioner elects an initial heating power level and, as represented at line 1656 and block 1568 a maximum warm-up interval is determined. That interval is loaded into the system by actuation of up-down switch 1575 in conjunction with readout 1576 (FIG. 25). As represented at line 1660 and block 1662 (FIG. 26C) the session therapy duration is determined. That duration will be monitored at such time as the lower threshold temperature is reached. Locating the implants then is commenced as represented at line 1664 and block 1666 with the administration of a general or local anesthetic agent following which, as represented at line 1668 and block 1670 the sensor implants are positioned utilizing guidance techniques in accordance with a preliminary placement pattern and the exterior or skin of the patient is marked to identify the closest location of the implants. Then, as represented at line 1672 and block 1674 a determination is made as to whether the implants are correctly positioned. In the event they are not, then the procedure returns as represented at line 1676 to line 1668. Where implant positioning is correct, then as represented at line 1678 and block 1680 the implant placement pattern map is updated if necessary. As a final step before commencement of a therapy session, as represented at line 1682 and block 1684 the marker location is recorded as well as all resonant center frequencies and associated sensor identification.

The patient is now prepared for undertaking one or many therapy sessions as labeled in correspondence with lines 1686 and 1687, extending to block 1688 (FIG. 26D) providing for the reproduction of the marker if necessary. Where therapy sessions subsequent to the initial ones are at hand, then the practitioner may wish to reconsider the election of the heating unit; determination of a maximum warm-up interval; the selection of session therapy duration; and the reloading of previously recorded unique resonant center frequencies into the interrogation assembly. As represented at line 1690 and block 1692 the practitioner selects the interrogate/heat duty cycle if an intermittent type control is at hand. That selection is made by actuation of up-down switches 1575 in conjunction with readout 1577 as shown in FIG. 25. Next, as represented at line 1694 and block 1696 the therapy time elapsed reset button or switch 1586 is actuated. The procedure continues as represented at line 1698 leading to block 1700 which provides for positioning the patient on a table or chair and appropriately orienting the marker, whereupon as represented at line 1702 and block 1704 the heating assembly output component or components are positioned as close as practical to the target tissue volume. Additionally, as represented at line 1706 and block 1708, utilizing the marker on the patient the excitation and receiver or sense antennae are positioned with respect to the target tissue volume. As represented at line 1710 and block 1712 the controller then acquires the on and continuity status of the interrogation assembly. With that information, as represented at line 1714 and block 1716 (FIG. 26E) a determination is made as to whether the interrogation assembly status is ok. In the event that it is not, then as represented at line 1718 and block 1720 an error cue is presented at display 1588 indicating that the antennae cables to the electronics and control console are not properly attached. Additionally, as represented at line 1722 and block 1724 a prompt is presented at display 1588 indicating that cable attachments should be checked and the procedure returns to line 1714 as represented at line 1726. Where the interrogation assembly status is ok, then as represented at line 1728 and block 1730 green LED 1590 is illuminated. Next, as represented at line 1732 and block 1734 the heating unit is actuated following which, as represented at line 1736 and block 1738, the control system acquires on and continuity status of the heating unit and determines, as represented at line 1740 and block 1742, whether that status is ok. Where that status is not ok, then as represented at line 1744 and block 1746 an error message is presented at display 1588. Additionally, as represented at line 1748 and block 1750 a prompt is presented at display 1588 advising the operator to check lead/cable attachments and the procedure returns to line 1736 as represented at line 1752. Where the heating unit status is ok, then as represented at line 1754 and block 1756 green LED 1592 is illuminated. With the above checks being made, as represented at line 1758 and block 1760, thermotherapy is started by actuating the "start therapy" button or switch 1596. With this actuation, as represented at line 1762 and block 1764 (FIG. 26F) the heating underway green LED 1600 is illuminated and the procedure continues as represented at line 1766 to the query at block 1768 determining whether all of the appropriate LEDs of LED arrays 834' and 844' are illuminated, indicating that heating is underway but that the lower threshold temperature has not been detected. In the event these LEDs are not illuminated, then as represented at line 1770 and block 1772 the practitioner is prompted to press the stop therapy button or switch 1604. As this occurs, as represented at line 1774 and block 1776, red LED 1606 is illuminated and, as represented at line 1778, the procedure extends to node A which reappears with line 1780 extending to line 1702. In the event of an affirmative determination with respect to the query posed at block 1768, then the procedure continues as represented at line 1782 and block 1784. Timing for maximum warm-up interval commences and the procedure continues as represented at line 1786 and block 1788. At block 1788, the control program queries as to whether the stop therapy button or switch 1604 on the control console has been pressed. If it has been pressed, then as represented at line 1790 and block 1792 the heating unit is turned off; red LED 1598 is illuminated; and green LED 1600 is turned off. The procedure then, as represented at line 1794 and block 1796, determines whether therapy is to be resumed. In the event it is to be resumed, as represented at line 1800 and block 1802 the therapy may be resumed for the remaining duration of the maximum warm-up interval or unlapsed therapy time by actuating or pressing the start therapy button or switch 1596. This will cause a turning off of red LED 1598 and as represented at line 1802, the procedure reverts to node B. Node B reappears in FIG. 26E in conjunction with line 1804 extending to line 1758. Where the determination at block 1798 is that the therapy is not to be resumed, then as represented at line 1806 and node 1808 the therapy session is ended.

Returning to block 1788, where the stop therapy button or switch has not been pressed, then as represented at line 1810 and block 1812 a determination is made as to whether all appropriate LEDs within array 834' and array 844' are illuminated. In the event they are not, then as represented at line 1814 and block 1816 a determination is made as to whether the maximum time of warm-up has timed out. If the maximum time of warm-up has timed out, then as represented at line 1818 and block 1820, red LED 1598 is illuminated and as represented at line 1822 and block 1824 an error message and prompt is presented at display 1588 and the procedure advances to node C as represented at line 1826.

Looking momentarily to FIG. 26I, node C reappears with line 1828 extending to block 1830 which provides for the adjustment of the heating unit output component position and/or the heating power level. The procedure then continues to node D as represented at line 1832. Node D reappears in FIG. 26G with line 1834 extending to line 1810.

Returning to the query at block 1816, where the maximum time to warm-up has not timed out, then as represented at line 1836 and block 1838 a determination is made as to whether all appropriate LEDs within arrays 838' and 844' are illuminated. In the event that they are not, then the program reverts to node D as represented at line 1840. Where those LEDs are appropriately illuminated, the program continues as represented at line 1842 extending to block 1844 providing for the commencement of therapy time-out. Returning to the query at block 1812, where the condition represented at block 1838 obtains, then the procedure diverts to line 1842 as represented at line 1846.

Returning to block 1844, where therapy time-out has commenced, then as represented at line 1848 and block 1850 where the heating unit elected is one requiring intermittent heating and interrogation, then that form of system activation is utilized in accordance with the interrogate/heat duty cycle elected in connection with up-down switches 1577 and readout 1578. The procedure then continues as represented at line 1852 (FIG. 26H) to the query posed at block 1854. Where any of the LEDs in the array 848' are illuminated, then as represented at line 1856, the program looks to node E. Looking momentarily to FIG. 26J, node E reappears in conjunction with line 1858 extending to block 1860. Block 1860 provides for turning off the heating unit, whereupon as represented at line 1862 and block 1864, the interrogation assembly is turned-on and, as represented at line 1866 the procedure reverts to node C (FIG. 26I).

Returning to the query at block 1854, where none of the temperature excursion LEDs at array 848' are illuminated, then the procedure progresses as represented at line 1868 and block 1870. Block 1870 determines whether or not the therapy duration has timed-out. In the event that it has not, then as represented at loop line 1872 extending to line 1852, the procedure dwells until such time-out occurs. At such time-out, as represented at line 1874 and block 1876 green LED 1602 is illuminated and green LED 1600 is turned off. As represented at line 1878 and block 1880 the heating unit and interrogation assembly are turned off and, as represented at line 1882 and block 1884 therapy data are recorded and as represented at line 1886 and node 1888 the therapy session is ended.

Hyperthermia currently is employed for purposes of limiting restenosis at the location of implanted stents in blood vessels. In general, such stents, for example, may be utilized in percutaneous transluminal coronary angioplasty (PTCA) for purposes of avoiding a collapse of arteries subsequent to balloon implemented dilation. Thermal treatment at the site of the stent will typically fall within a temperature range from about 40° C. to about 45° C. As in other thermotherapeutic procedures, necessary sensing of temperature heretofore has been carried out in an invasive manner. Specifically, a transluminal catheter borne thermal sensor is maneuvered within the stent structure in the course of the thermal therapy procedure. As is apparent, such an invasive positioning of the temperature sensor is required each time the hyperthermia therapy is performed, a procedure which may be called for relatively often. In addition to the risk of this invasive positioning of the temperature sensor, the catheterization of the patient involves a substantial cost. See the following publications in this regard:

(43) Stefanadis, C., et al., "Hyperthermia of Arterial Stent Segments by Magnetic Force: A New Method to Eliminate Intimal Hyperplasia." *Journal of the American College of Cardiology*, 37 (2) Supp. A: 2A-3A (2001).

(44) See additionally European Patent Application No. EP 1036574A1.

Figure 27:
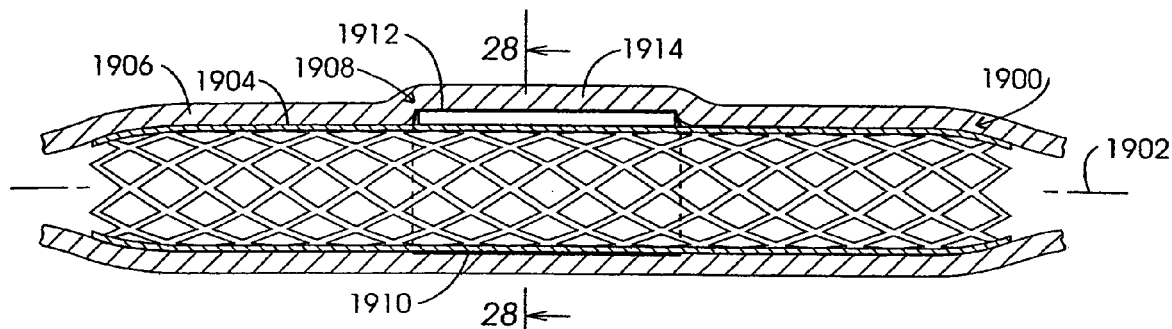
FIG. 27 is a schematic sectional representation of a combined stent and temperature sensor according to the invention embedded within a blood vessel.
Figure 28:
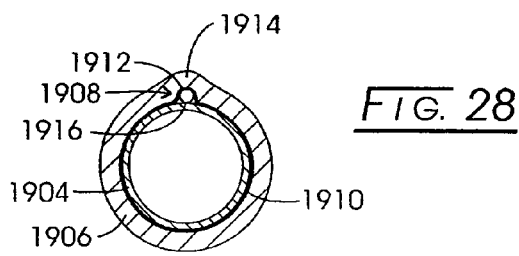
FIG. 28 is a sectional view taken through the plan 28-28 in FIG. 27.

FIGS. 27 and 28 illustrate an initial embodiment for a stent formed of non-magnetic material or material which can be heated from an extra body source, for example, by alternating current field heating and which initially incorporates an untethered temperature sensor which is fixed to it prior to the implantation. Looking to FIGS. 27 and 28, the mesh-structured stent is represented generally at 1900 extending about a central axis 1902. Typically, such stents as at 1900 are formed of a non-magnetic inductively exercisable material, for example, austenitic stainless steel such as type 316, titanium, titanium alloys and nitinol. Non-magnetic materials are utilized inasmuch as they often will be located within the imaging field of highly magnetic devices such as MRI systems and the like. Stent structures are described in the following publications:

(45) *Interventional Vascular Product Guide*, Martin Dunitz, Ltd., London (1999).

(46) *Handbook of Coronary Stents*, 3rd ed., Martin Dunitz, Ltd., London (2000).

The mesh-like generally cylindrically-shaped stent 1900 is seen to be implanted such that its outwardly disposed contact surface 1904 will have been urged into abutting and fixed intimate connection with the intima of a blood vessel 1906. Fixed to contact surface 1904 at the central region of stent 1900 is an untethered temperature responsive assembly according to the invention which is represented generally at 1908. Component 1908 is configured with the rod-shape of device 670 described in connection with FIGS. 14 and 14A-14C. The ferrite core as described at 672 of the component will be formulated to develop a Curie transition at an upper temperature limit as described above. That upper temperature limit is elected inasmuch as the instant embodiment includes only one passive device with a signature resonant center frequency. Sensor 1908 may be bonded with the stent 1900 and its securement may be further assured by the positioning of a biocompatible flexible sheath or band 1910 over the central portion of the stent 1900 and over the outwardly disposed surface 1912 of the sensor assembly 1908. Band 1910 may, for instance, be formed of a biocompatible, non-metallic material such as silicone elastomer, Dacron or Teflon. The arrangement is seen to slightly additionally distend blood vessel 1906 at region 1914. If desired, the sensor assembly 1908 may be mounted in intimate thermal exchange relationship with the stent 1900. Providing a biocompatible electrically insulated conformal coating such as the earlier-described Parylene as shown at 1916 in FIG. 28 is beneficial and may promote adhesion of the sensor 1908 to stent 1900.

Figure 29:
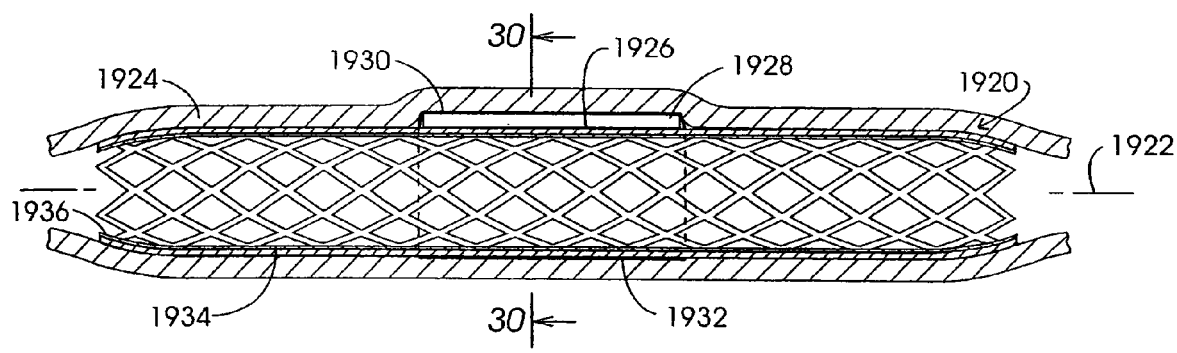
FIG. 29 is a sectional schematic view of a stent according to the invention incorporating a heat activated release agent coating and being shown embedded within a blood vessel.
Figure 30:
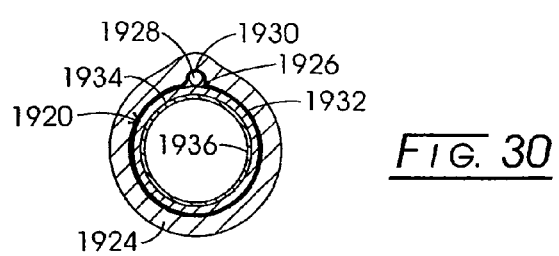
FIG. 30 is a sectional view taken through the plane 30-30 in FIG. 29.

The combined stent and untethered sensor components discussed in conjunction with FIGS. 27 and 28 also may be utilized to implement a thermally activatable drug release feature. Referring to FIGS. 29 and 30, a stent represented generally at 1920 with a centrally disposed axis 1922 is shown having been implanted within a blood vessel 1924. Attached to the outer contact surface 1926 of stent 1920 is an unteathered passive resonant circuit based sensor component 1928. Sensor component 1928 may, as before, be configured as described in connection with FIGS. 14 and 14A-14C. Component 1928 may be fixed in thermal exchange relationship with the contact surface 1926 and further may be coated with an electrically insulated conformal biocompatible coating 1930 such as the earlier-described "Parylene" which functions to aid in the securement of the sensor to the stent 1920. This securement is further enhanced by a flexible band or sheath 1932 surmounting both the stent 1920 and the passive resonant sensor component 1928. Band 1932 may be structured in the manner of earlier-described band 1910. Note, however with the arrangement of FIGS. 29 and 30 that the inward surface 1934 of stent 1920 is coated with a thermally activatable drug release coating as shown at 1936. The release coating will have a thickness which may fall within the range of about 0.001 inch (0.025 mm) to about 0.20 inch (5.0 mm) and preferably will fall within a range of from about 0.005 inch (0.13 mm) to about 0.10 inch (2.5 mm). Such drugs may be provided, for example, as paclitaxel and the antibiotic Sirolimus as well as anti-thrombogenic agents such as heparin and the like. See the following publications in this regard:

(47) Simonsen, "Percutaneous intervention arena still expanding for heart disease." *Cardiovascular Device Update* 7(5): 1-7 (May 2001).

(48) "Drug-Coated Stents Poised for Growth", *Cardiovascular Device Update*, 7(9): 8-10 (September, 2001).

The nominal drug release temperature will range from about 39° C. to about 65° C. and preferably from about 41° C. to about 50° C. Drug release coating 1936, when non-invasively heated to a drug releasing temperature, provides a controlled amount of a selected drug at the situs of the stent 1920 to limit restenosis phenomena. Such a drug release process can be repeated at therapeutic intervals which may range from weeks to months to even years. Additionally, the coating may be activated in the event the patient's symptoms or diagnostic methods indicate that restenosis is occurring and progressing to the point that therapeutic intervention is warranted. Where hyperthermia therapy is combined with drug release activity, more than one passive resonant frequency based sensor may be employed each being assigned a different Curie transition temperature.

The untethered passive resonant circuit based sensors preferably are positioned on the outer contact surface of the stent structure, inasmuch as such location provides a factor of safety with respect to the adhesion of the individual components to that contact surface. Should the coupling be damaged, the sensor components are retained by the stent structure itself outside of luminal blood flow. In addition, the detectable signal amplitude issuing from the passive resonant circuit is greater if the sensor is placed on the outside of a metallic stent.

Figure 31:
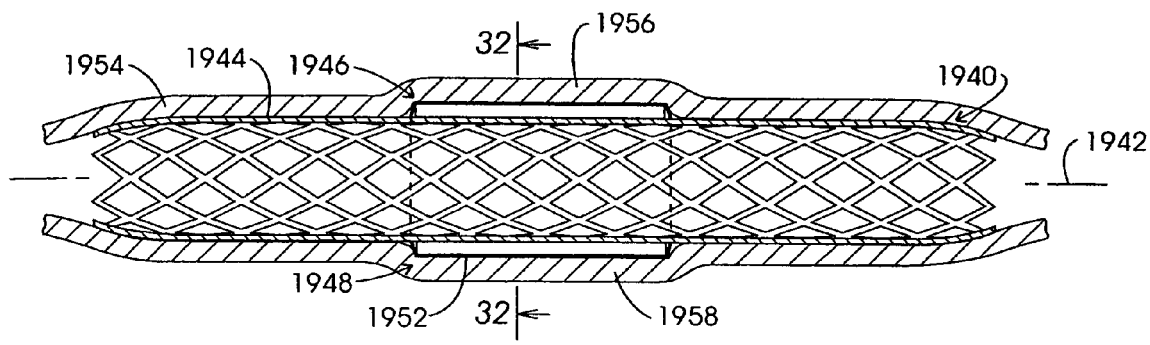
FIG. 31 is a schematic sectional view of another stent embodiment according to the invention, the device being shown embedded within a blood vessel.
Figure 32:
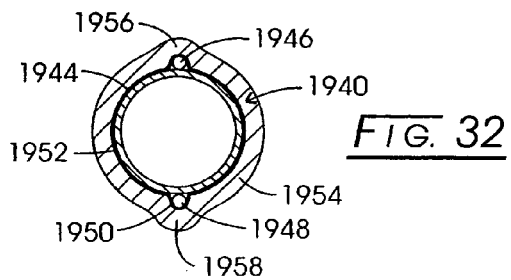
FIG. 32 is a sectional view taken through the plane 32-32 shown in FIG. 31.

Two of these resonant circuit based passive sensors may be employed to provide the earlier-described lower threshold temperature sensing and upper limit temperature sensing. Additionally, multiple sensors may be employed to provide a redundancy. FIGS. 31 and 32 illustrate a stent structure with lower threshold and upper limit temperature value sensors in conjunction with a nonmagnetic stent represented generally at 1940. Formed, as before, of a nonmagnetic material, stent 1940 is seen disposed about a central axis 1942 and has a generally mesh-like structuring with an outwardly disposed contact surface 1944 of generally cylindrical configuration. Untethered passive resonant circuit based lower threshold and upper limit temperature level sensors are shown respectively at 1946 and 1948 coupled to contact surface 1944 at diametrically opposite locations. As before, each of these sensors may be configured in the manner described in connection with FIGS. 14 and 14A-14C. The assembly additionally may be coated with an electrically insulative biocompatible material represented at 1950 in FIG. 32. That material, which may be the earlier described "Parylene" functions to enhance the bond between the sensors and the outer contact surface 1944. Sensors 1946 and 1948 further are secured to the contact surface 1944 by a flexible band or sheath 1952. Band 1952 is structured in the manner of the earlier-described band 1910. As before, the instant figures reveal that the blood vessel 1954 within which stent 1940 is positioned is diametrically enlarged at regions 1956 and 1958 to accommodate for the thickness of sensors 1946 and 1948 as well as band 1952.

As noted earlier, essentially all metallic stents which have been implanted are formed of nonmagnetic material in view of the potential involvement of highly magnetic imaging systems. As a consequence, those pre-implanted stents can be retrofitted in vivo with the temperature sensing aspect of the present invention to enhance noninvasive thermotherapeutic procedures or subsequent treatment of restenosis phenomena. The retrofitting approach, in effect, provides for the installation of a temperature sensing component containing a stent-like structure which is diametrically expandable within the preexisting stent.

Figure 33:
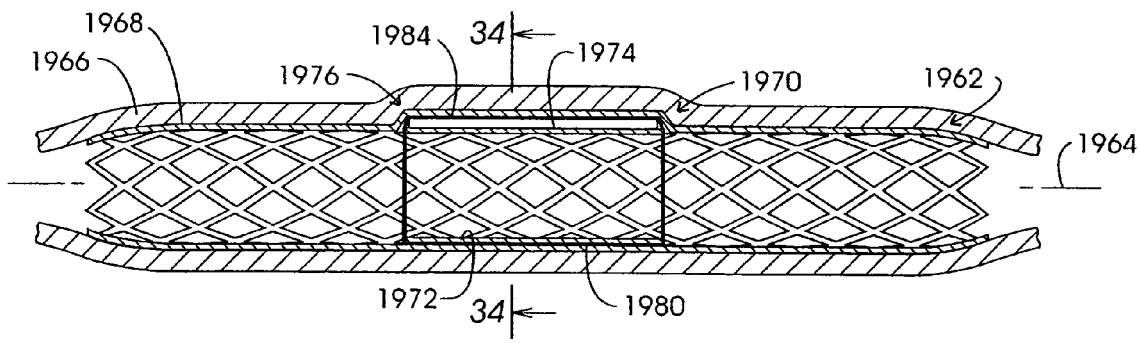
FIG. 33 is a sectional schematic view of a stent embedded within a blood vessel and having been retrofitted with a sensor assembly according to the invention.
Figure 34:
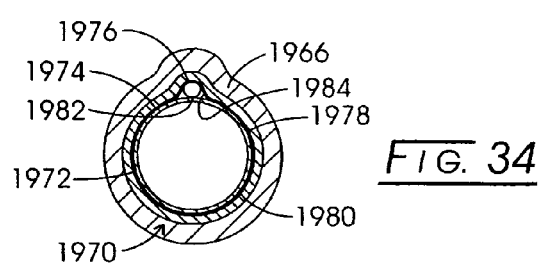
FIG. 34 is a sectional view taken through the plane 34-34 shown in FIG. 33.

Referring to FIGS. 33 and 34, an asymmetrical retrofitting design is illustrated. In the figure, a nonmagnetic metal mesh stent is represented in general at 1962 disposed about a central axis 1964 which has been previously implanted within a blood vessel 1966. Note in this regard that the outwardly disposed surface 1968 of the stent 1962 is in contact with the intima of the vessel 1966. The untethered passive resonant circuit based temperature sensor carrying insert or support member is seen at 1970 disposed about central axis 1964. Insert 1970 is of generally cylindrical configuration with an interior surface 1972 and exterior surface 1974 to which an untethered passive resonant circuit based temperature sensor 1976 is bonded. That bond may establish a temperature exchange relationship between the insert and the stent. In general, the insert 1970 may be formed with essentially the same mesh structuring and material as present in the previously implanted stent 1962. Such mesh structuring is not shown in the figures in the interest of illustrational clarity. FIG. 34 shows that the insert and associated sensor is coated with a biocompatible coating 1978 which may be provided as the earlier-described "Parylene" material. Additionally, the structural integrity of the attachment of the sensor 1976 is enhanced by a flexible band 1980. Sensor carrying insert or support member 1970 is inserted within the preexisting stent 1962 using balloon angioplasty procedures. In order to accommodate for the asymmetrical positioning of only a single sensor 1976, the insert member 1970 is structured so that it is preferentially expandable in the region 1982 immediately beneath the sensor 1976. Accordingly, upon balloon expansion during the placement of insert 1970, the region 1982 will expand from an initial insertion diameter diametrically outwardly against the interior surface 1984 of the preexisting stent 1962 to create the crimping expansion of the contacting surface of that stent 1962 as represented at region 1982. Preferential expansion of the insert 1970 can be provided by structuring the stent to be thinner at that region and/or the mesh structure opening size may be asymmetrically varying.

Figure 35:
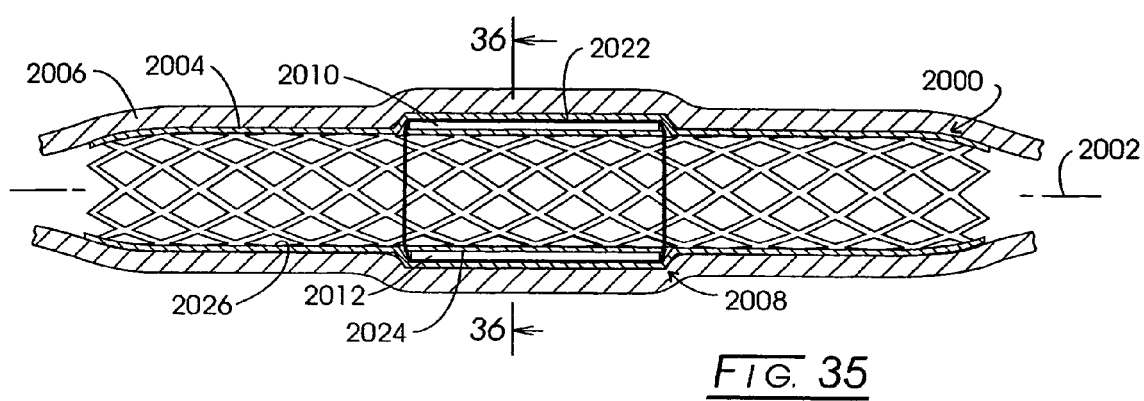
FIG. 35 is a sectional schematic view of a stent embedded within a blood vessel and showing a retrofit thereof with two sensor assemblies according to the invention.
Figure 36:
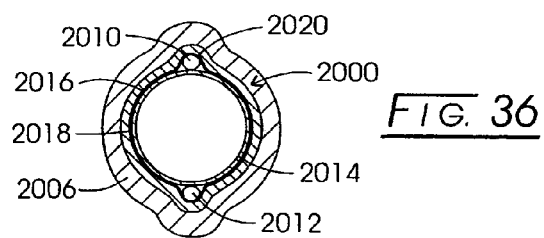
FIG. 36 is a sectional view taken through plane 36-36 shown in FIG. 35.

Referring to FIGS. 35 and 36, a retrofitting or "stent within a stent" approach is illustrated wherein two passive, resonant frequency based temperature sensors are employed. One such sensor may be structured with a core component providing a lower threshold Curie temperature and the other an upper limit Curie temperature as above-described. With such an arrangement, the temperature elevation at the stent may be bracketed between those two temperature values. In the figures, a pre-implanted nonmagnetic stent is represented generally at 2000. As before, stent 2000 has a mesh-type structure of generally cylindrical configuration disposed about central axis 2002. The cylindrical outer surface 2004 of stent 2000 is in abutting compressive engagement with the intima of a blood vessel 2006. In order to carry out a hyperthermia form of treatment for restenosis with the necessary temperature control, a secondary stent or support member insert represented generally at 2008 extending about axis 2002 is formed of an expandable mesh material, e.g., stainless steel 316, Nitina, or titanium, and functions to support diametrically oppositely disposed temperature sensors configured according to the invention and represented generally at 2010 and 2012. Sensor 2010 may be configured with a ferrite core component having a Curie temperature selected as a lower threshold temperature, while sensor 2012 may be configured with a ferrite core component exhibiting an upper limit Curie temperature to effect a noted bracketing control. Similar to the embodiment of FIGS. 33 and 34, the insert or support member 2008 is configured with a cylindrical wall surface 2014 and an exterior surface 2016 upon which the sensors 2010 and 2012 are connected. To enhance this connection, a flexible band 2018 surmounts both the cylindrical exterior wall surface 2016 and the sensors 2010 and 2012. FIG. 36 reveals that the insert and associated sensors are coated with an electrically insulative biocompatible conformal coating 2020 such as the earlier-described "Parylene". Insert 2008 also may be structured so that it is preferentially expandable in the region of each of the sensors 2010 and 2012. Upon balloon expansion during the placement of the insert and its supported sensors the regions 2022 and 2024 will expand from an initial insertion diameter diametrically outwardly against the interior surface 2026 of the preexisting stent 2000 to create the crimping expansion of the contacting surfaces. Preferential expansion at those regions can be provided as described in conjunction with FIGS. 33 and 34. The earlier-discussed hyperthermia therapy temperature ranges apply to the arrangement of FIGS. 35 and 36. A nominal stent heating temperature of 45° C. has been described in publication (44) supra.

See additionally the following publication:
(49) Thury, A., et al., "Initial Experience With Intravascular Sonotherapy For Prevention Of In-Stent Restenosis; Safety And Feasibility", J. of Am. College of Cardiology 37 (2) Supplement A. (2000)

The instrumentation described in connection with FIGS. 19 and 25 in general may be employed for carrying out the heating of nonmagnetic stents as described above. Where inductive heating components are utilized then the intermittent form of operation of the system is called for. However, U.S. Pat. No. 6,451,044 (supra) describes an ultrasound heating of a stent formed of an ultrasound absorptive material. Such a stent therefore could be heated while continuous temperature monitoring is carried out. Looking to FIG. 37, the instrumentation and support equipment discussed in connection with FIG. 25 are illustrated for exemplary purposes in connection with a patient 2030. Patient support components, heating components and interrogation components which are repeated from FIG. 25 are shown with the same earlier presented numerical identification but in primed fashion. Stent 1940 (FIG. 31) reappears adjacent the heart region 2032 of patient 2030. Heating component 1557' is located in adjacency with the stent 1940. Excitation coil 1530' is located for exciting the temperature sensors of stent 1940, while the sense antenna 1542' is positioned about the region of the stent 1940 location. The instantaneous heating power generated within the stent 1940 will generally fall with a range of from 0.20 calories/second to about 20 calories/second and preferably will be within a range of between about 0.5 calories/second and about 10 calories/second. The nominal hyperthermia therapy temperature for stents such as at 1940 will fall within a range of from about 39° C. to about 70° C. and preferably within a range from about 41° C. to about 50° C.

Referring to FIGS. 38A-38B and 39A-39H a procedural flow chart is presented concerning the implanting of stent supported temperature sensors according to the invention. The procedure is associated with the instrumentation and equipment described in connection with FIG. 37 and commences with start node 2040 and line 2042 extending to block 2044. Block 2044 describes the provision of a stent with two or more sensors, one having an inductor core exhibiting a lower threshold Curie temperature and the other having an inductor core exhibiting an upper limit Curie temperature characteristic such that they bracket a temperature range for hyperthermia treatment of stenosis/restenosis. As represented at line 2046 and block 2048, as an alternative, a support insert as described in connection with FIGS. 35 and 36 may be provided having the same form of sensor response characteristic. The procedure then continues as represented at line 2050 and block 2052 providing for the loading of all unique resonant frequencies into the interrogation assembly. Identification of the sensors is only required where more than two are at hand. Next, as represented at line 2054 and block 2056 the interrogation assembly is utilized to carry out an ex-vivo pre-testing of the two sensors for their resonant performance at room temperature. Accordingly, as represented at line 2058 and block 2060, a query is posed as to whether the appropriate LEDs from arrays 834' and 844' are illuminated. In the event that they are not, then as represented at line 2062 the procedure extends to node A. Node A reappears with line 2064 extending to start line 2042. Where all appropriate LEDs have been illuminated, then as represented at line 2066 and block 2068 (FIG. 38B) a general or local anesthetic agent is administered and, as represented at line 2070 and block 2072 the sensor containing stent is located within the patient's blood vessel using conventional stent delivery systems. Once it is positioned, it is deployed at the target location and the deployment system is removed. As an alternative, as represented at line 2074 and block 2076 a support member with two associated sensors according to the invention is described in conjunction with FIGS. 35 and 36 may be positioned within a previously implanted stent and expanded such that it is secured within that preexisting stent. The deployment system then is removed. The procedure then continues as represented at line 2078 and block 2080 providing for the positioning of a marker on the skin surface of the patient close to the location of the stent. Next, as represented at line 2082 and block 2084 the location of the thus placed marker is recorded for future reference and the two resonant center frequencies are recorded for any future reference. As represented at line 2086 and node 2088 the stent positioning phase is then ended.

Figure 37:
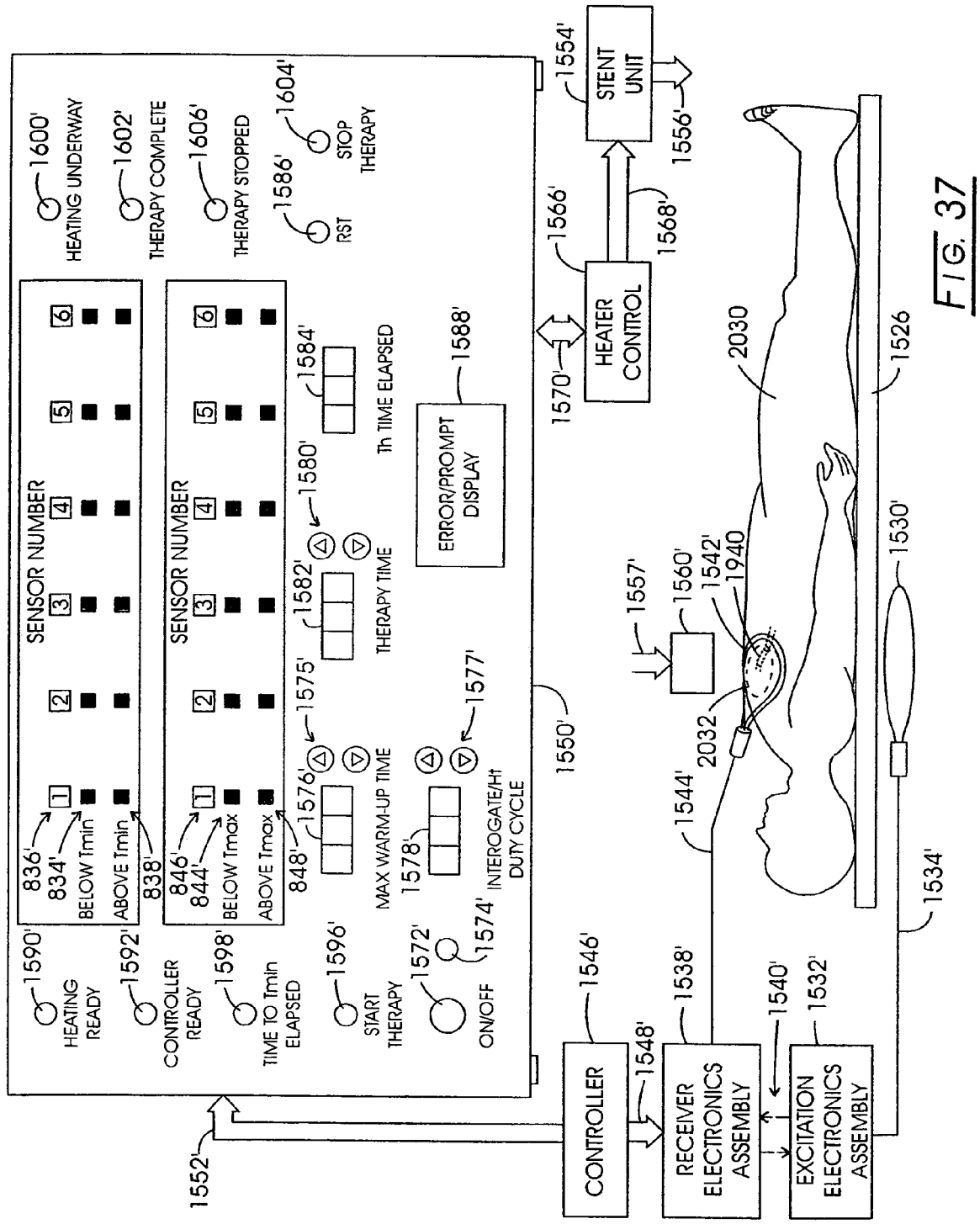
FIG. 37 is a schematic representation of another embodiment of the system of the invention.
Figure 39B:
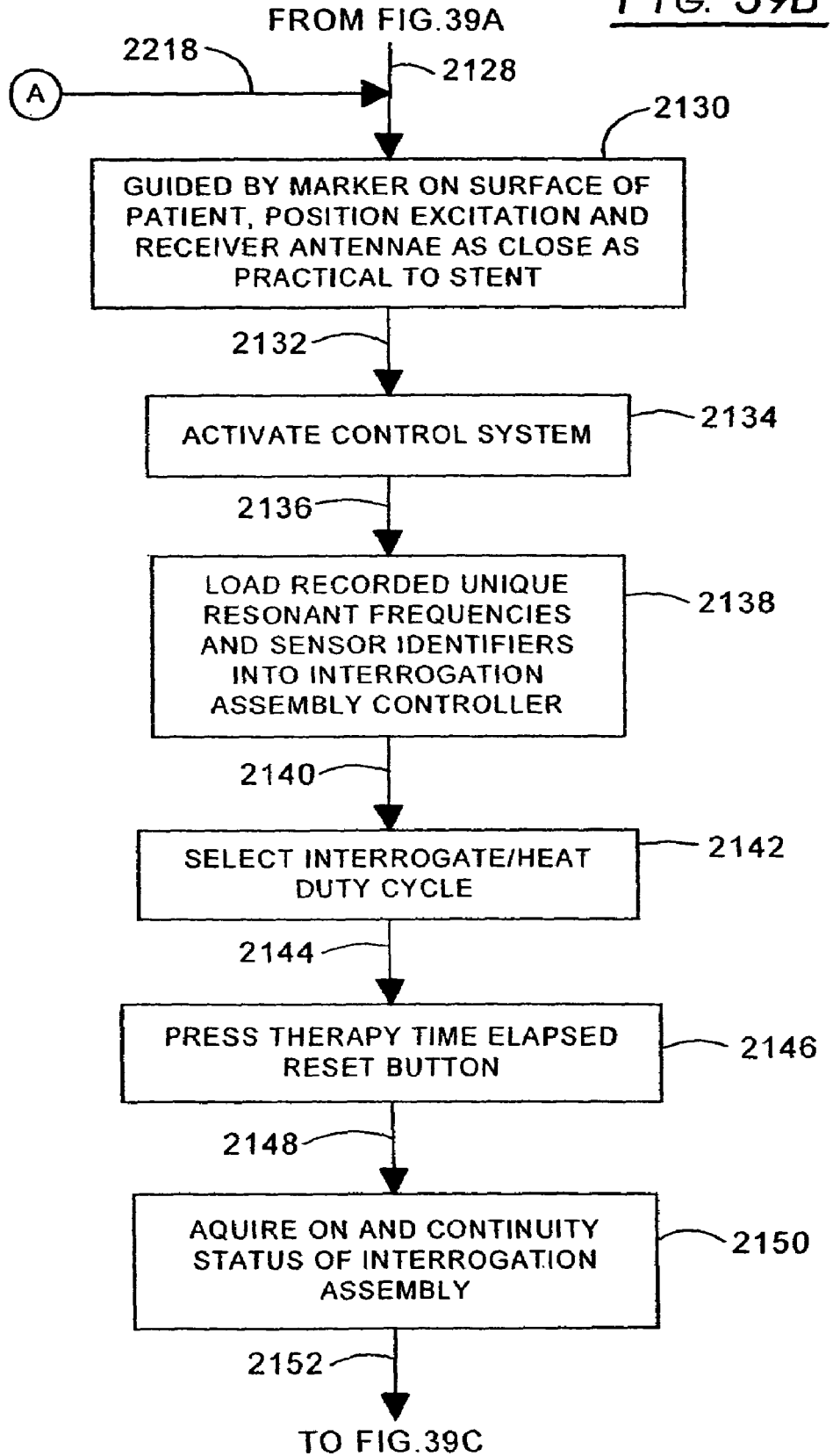
Figure 39E:
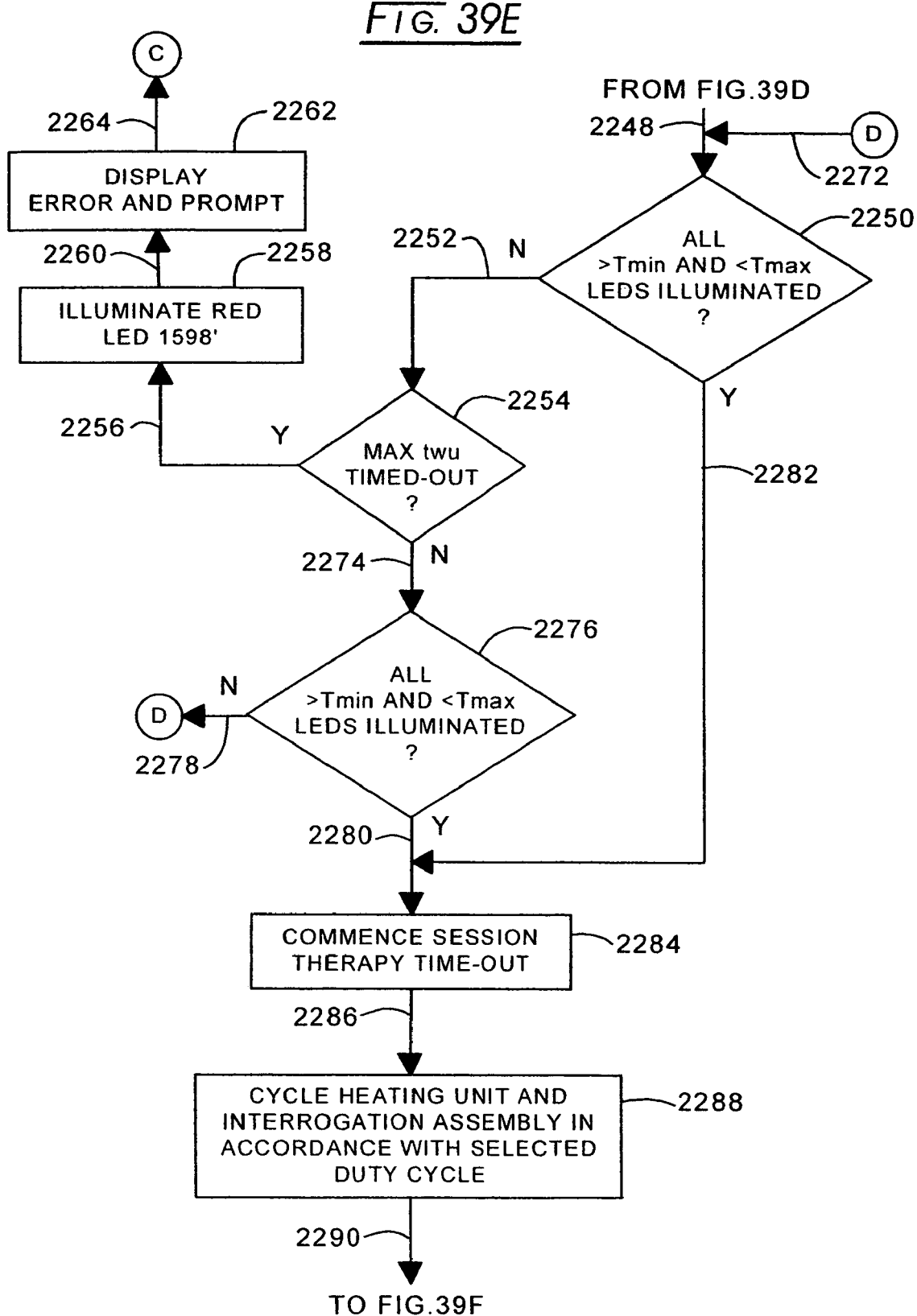

Subsequent to the stent positioning phase, the patient will be monitored for the occurrence of clinically significant stenosis/restenosis. This may be to a requirement for a number of hyperthermia based treatment sessions which can extend over a lengthy period. Referring to FIGS. 39A-39H, and block 2090 of FIG. 39A, such checks may be carried out, for instance, using angiography, diagnostic ultrasound, ex-ray, or MRI techniques. The procedure then continues as represented at line 2092 and block 2094 presenting a query as to whether or not evidence of stenosis/restenosis is present. In the event that it is not, then as represented at line 2096 and block 2098 such checks are continued, the patient's cardiac circulatory function being monitored on a periodic basis. Where evidence of stenosis/restenosis does exist, then as represented at lines 2100 and 2101, thermal therapy according to the invention is commenced. Lines 2100 and 2101 are labeled inasmuch as a sequence of such sessions may be carried out over an extended interval of time. Accordingly, certain of the steps undertaken earlier may have to be repeated. Line 2101 is seen extending to block 2102 providing for the election of a stent heating system. Next, as represented at line 2104 and block 2106 the practitioner elects the initial heating power level for the heating system and, as represented at line 2108 and block 2110 determines the maximum warm-up interval, $t_{WU}$ to initially achieve the lower threshold designated temperature. Additionally, as represented at line 2112 and block 2114 a determination is made as to the session therapy duration at temperatures at or above the designated lower threshold temperature and below the upper limit temperature. As represented at line 2116 and block 2118 the marker at the patient's skin may be relocated at its earlier recorded position if necessary. With the marker available, as represented at line 2120 and block 2122 the patient is positioned on an appropriate treatment support such that the marker is clearly visible to provide for close proximity of the heating system output, for instance, an inductive coil. Thus, as represented at line 2124 and block 2126 the heating system output component is placed as close as practical to the stent with guidance by the marker. The procedure then continues as represented at line 2128 and block 2130 (FIG. 39B) providing for again utilizing the marker to position excitation and receiver or sense antennae as close as practical to the stent. It may be recalled that the sense antenna is quite flexible and may be draped over the patient's body in the vicinity of the stent. Next, the control system is activated as represented at line 2132 and block 2134, and, as represented at line 2136 and block 2138, where necessary the unique resonant frequencies and, if called for, sensor identifiers are loaded into the interrogation assembly control function. As represented at line 2140 and block 2142 a selection is made as to the interrogate/heat duty cycle which may be provided as part of the manufacturer of the system or inputted at up-down switches 1577' seen in FIG. 37. As represented at line 2144 and block 2146, the practitioner will actuate or press the therapy time elapsed reset switch or button shown in FIG. 37 at 1586'. The procedure then continues as represented at line 2148 and block 2150 providing for testing the interrogation assembly acquiring on and continuity type status information. The information thus acquired, as represented at line 2152 and block 2154 (FIG. 39C), a determination is made as to whether the status of the interrogation assembly is ok. In the event that it is not, then as represented at line 2156 and block 2158 an error message is presented at display 1588' and, as represented at line 2160 and block 2162, a prompt is displayed advising the practitioner to check cable attachments, whereupon the procedure reverts to line 2152 as represented at line 2164. Where the determination at block 2154 is that the interrogation assembly status is ok, then as represented at line 2166 and block 2168, green LED 1582' (FIG. 37) is illuminated and the procedure attends to the testing of the stent heating unit as represented at line 2170 and block 2172. Upon actuating the heating unit into an on condition, as represented at line 2174 and block 2176 the on continuity status of the heating unit is acquired and, as represented at line 2178 and block 2180 a determination is made as to whether the heating unit status is ok. In the event that it is not, then as represented at line 2182 and block 2184 an error message is presented at display 1588' (FIG. 37). Additionally, as represented at line 2186 and block 2188, a prompt message advising the practitioner to check lead/cable attachment is provided at that display. The procedure then reverts to line 2174 as represented at line 2190.

Where the heating unit status is ok, then as represented at line 2192 and block 2194, green LED 1590' (FIG. 37) is illuminated and the procedure continues as represented at line 2196 and block 2198. Hyperthermia therapy is started by actuating the start therapy switch 1596'. Actuating the start therapy button, in turn, effects the illumination of green LED 1600' as represented at line 2200 and block 2202 (FIG. 39D). Next, as represented at line 2204 and block 2206, a check is made that the appropriate LEDs located within arrays 834' and 844' are illuminated inasmuch as they are at monitor temperatures. For the instant demonstration one LED in each of these arrays will be illuminated. In the event of a negative determination with respect to the query posed at block 2206, then as represented at line 2208 and block 2210 the practitioner will actuate the stop therapy switch 1604' and, as represented at line 2212 and block 2214, red LED 1606' is illuminated and the green LED 1500' is turned off. The procedure then diverts as represented at line 2216 to node A. Node A reappears in FIG. 39B in connection with line 2218 extending to line 2128.

Where the query at block 2206 indicates that the appropriate LEDs are illuminated, then as represented at line 2220 and block 2222 the control system commences timing for the maximum time to warm up. As represented at line 2224 and block 2226 a determination is made as to whether the stop therapy switch or button 1604' (FIG. 37) has been pressed or actuated. In the event that it has, then as represented at line 2230 and block 2232 the heating unit is turned off, red LED 1598 is illuminated and green LED 1598' is illuminated and green 1600' is turned off (FIG. 37). Next, as represented at line 2234 and block 2236 the practitioner determines whether or not therapy is to be resumed. If it is to be resumed, as represented at line 2238 and block 2240 the start therapy switch or button 1596' is actuated and red LED 1598' is turned off (FIG. 37). The procedure then reverts to node B as represented at line 2242. Node B reappears at FIG. 39C in conjunction with line 2246 extending to line 2196. Where the determination at block 2236 is that therapy is not to be resumed, then as represented at line 2241 and node 2243 the therapy session is ended.

Returning to FIG. 39D and block 2226, where the stop therapy switch has not been actuated, then as represented at line 2248 and block 2250 (FIG. 39E), a determination is made as to whether appropriate ones of the LEDs in array 838' and array 844' are illuminated. Where they are not, as represented at line 2252 and block 2254 a determination is made as to whether the maximum time to warm-up interval has timed out. In the event that it has, then as represented at line 2256 and block 2258, red LED 1598' is illuminated and, as represented at line 2260 and block 2262 error and prompt messages are provided at display 1588' and the procedure reverts to node C as represented at line 2264.

Looking momentarily to FIG. 39G, node C reappears in conjunction with line 2266 extending to block 2268. Block 2268 provides for adjusting the heating unit output component position and/or the heating power level. The procedure then reverts as represented at line 2270 to node D.

Returning to FIG. 39E, node D reappears in association with line 2272 extending to line 2248. Where the inquiry posed at block 2254 indicates that the maximum warm-up time interval has not timed out, then as represented at line 2274 and block 2276 the query as posed at block 2250 is repeated in a determination as to whether therapy level temperatures have been reached. In the event that they have not been so reached, then as represented at line 2278, the procedure reverts to earlier described node D. Where all appropriate ones of the LEDs are illuminated the procedure continues as represented at line 2280. Correspondingly, where the same result is achieved with respect to the query at block 2250, then the procedure continues as represented at line 2282 extending to line 2280. Line 2280, in turn, extends to block 2284 indicating the commencement of session therapy time-out with a resulting activation of therapy time elapsed readout 1584' (FIG. 37). During this therapy time, as represented at line 2286 and block 2288, for intermittent performance which typically is employed with stent therapy, the heating unit and interrogation assembly are intermitted or cycled in accordance with the duty cycle which may have been provided in conjunction with up-down switches 1577'. The procedure then continues as represented at line 2290 and block 2292 (FIG. 39F) where a query is posed as to whether an LED in the over-temperature array 848' is illuminated. In the event that there is such an over-temperature, as represented at line 2294 the procedure diverts to node E.

Looking momentarily to FIG. 39H, node E reappears with line 2296 extending to block 2298 providing for turning off the heating unit. Then, as represented at line 2300 and block 2302 the interrogation assembly is turned on and as represented at line 2304, the procedure reverts to earlier-described node C which ultimately returns to node D.

Returning to FIG. 39F and block 2292, where no temperature excursions are at hand, then as represented at line 2306 and block 2308 a determination is made as to whether the therapy duration has timed out. If it has not, the procedure dwells as represented by loop line 2310 extending to line 2290. Where no temperature excursions are at hand, then the procedure continues as represented at line 2312 and block 2314 to carry out the illumination of green LED 1602' and turn off green LED 1600' (FIG. 37). Further, as represented at line 2316 and block 2318 the heating unit and interrogation assembly are turned off and, as represented at line 2320 and block 2322 the therapy data are recorded. Upon completing a recordation of the therapy data, as represented at line 2324 and node 2326 the therapy session is ended.

Figure 40:
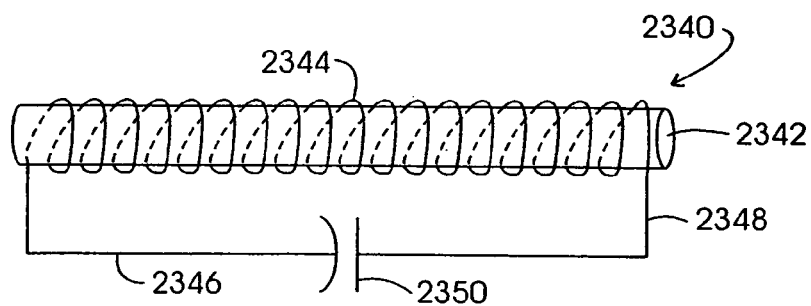
FIG. 40 is an electrical schematic diagram of another sensor according to the invention employing a passive resonant circuit with temperature responsive capacitance.
Figure 41:
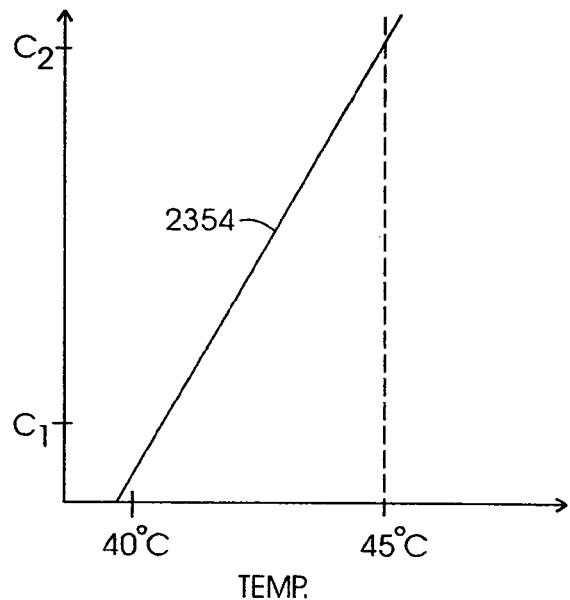
FIG. 41 is a graph plotting capacitance variation with a desired temperature range.

The passive resonant circuit based sensor implant of the invention also may be implemented utilizing an inductive component exhibiting substantially uniform relative permeability over a temperature range of interest, for example, between 40° C. and 45° C. in combination with a capacitor component which exhibits capacitance values as a function of temperature. The involved passive resonant circuit will physically appear essentially identical to that described in connection with FIGS. 7 and 14 and 14A-C. Looking to FIG. 40, an inductor is represented generally at 2340 as comprising a ferrite core 2342 about which are provided the turns 2344 of an inductive winding. These turns 2344 are coupled in series, as represented at leads 2346 and 2348, to the oppositely disposed plates of a capacitor 2350, the capacitance values of which vary with temperature. In this regard, referring to FIG. 41 the capacitance exhibited by capacitor 2350 may be represented by the curve 2354 as it extends between capacitance values C1 and C2 within a range of temperatures, for example, between 40° C. and 45° C. The value of capacitance is given by the expression:

$$C = (\text{const.})(\in A)/d$$

where:
C is capacitance;
∈ is the dielectric constant;
A is plate area; and
d is the distance between the capacitor plates.

From that expression it may be seen that the capacitance may be varied by altering either or both the values d and c.

Figure 42:
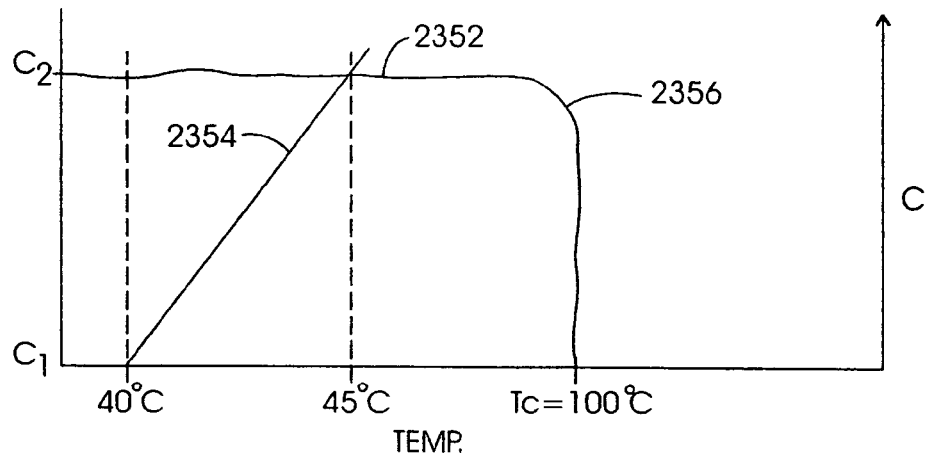
FIG. 42 is a graph schematically showing the graph of FIG. 40 in combination with an inductor core component exhibiting substantially uniform relative permeability over a temperature range of interest.

Looking additionally to FIG. 42, curve 2354 is reproduced in conjunction with the relative permeability characteristic of the core 2342 as represented at curve 2352. For exemplary purposes, curve 2352 is shown exhibiting a Curie transition at knee region 2356 which may be, for example, 100° C., a temperature level well above the temperature range of interest eliciting the variation in capacitance with temperature. This implant arrangement is not limited therefore to a single Curie temperature based set point but may provide monitorable resonant frequencies which vary along the curve 2354 since the resonant frequency, $f_o$, is inversely proportional to the capacitance, C, as discussed earlier.

Since certain changes may be made in the above-described system, apparatus and method without departing from the scope of the invention herein involved, it is intended that all matter contained in the above description or shown in the accompanying drawings shall be intrepid as illustrative and not in a limiting sense.

The invention claimed is:

1. The method of evaluating a temperature related physical parameter at a subcutaneous region of an animal body, comprising the steps of:
    (a) providing one or more passive resonant implants having an electromagnetic response to an extra body applied excitation electromagnetic field, said response exhibiting a predetermined resonant center frequency or frequencies when said implant is at a monitor temperature or temperatures;
    (b) providing a detector assembly with an antenna, said detector having a detector output of given amplitude in response to antenna detections of said electromagnetic response at said predetermined resonant center frequency;
    (c) positioning said detector assembly antenna at an extra body location effective for deriving said detector response;
    (d) positioning said one or more implants in thermal transfer relationship with said animal body region;
    (e) applying said excitation electromagnetic field from an extra body location for an excitation interval effective to elicit said electromagnetic response;
    (f) determining the presence of said monitor temperature or temperatures within a resonance time subsequent to said excitation interval in correspondence with said detector output; and
    (g) evaluating said physical parameter in correspondence with said step (f).

2. The method of claim 1 in which:
    said step (a) provides one or more of said passive resonant implants, each having an electromagnetic response at a unique resonant center frequency when said one or more implants are at a said monitor temperature or temperatures, and exhibit a decrease in the intensity of said response at said unique resonant center frequency when approaching a target temperature above said monitor temperature or temperatures.

3. The method of claim 2 in which:
    said step (f) determines the presence of said target temperature subsequent to said excitation interval in correspondence with a substantial diminution of said amplitude of said detector output.

4. The method of claim 1 in which:
    said step (a) provides one or more said passive resonant implants as having a said electromagnetic response at a said predetermined resonant center frequency when said one or more implants are at a said monitor temperature or temperatures, and exhibit an absence of said response at said predetermined resonant center frequency when at a target temperature which is above said monitor temperature or temperatures.

5. The method of claim 1 in which:
    said physical parameter is the inflammation of tissue of said body at said region.

6. The method of claim 1 further comprising the steps:
    (h) providing a heating assembly controllable for the generation of heat at said subcutaneous region of the body from an application component located externally of said body; and
    (i) controlling said heating assembly to elevate the temperature of said subcutaneous region in correspondence with said detector output.

7. The method of claim 6 in which:
    said step (a) provides one or more of said passive resonant implants as having a said electromagnetic response at a resonant center frequency when said one or more implants are at a said monitor temperature or temperatures, and exhibit a decrease in the intensity of said response at said predetermined resonant frequency when approaching a target temperature above said monitor temperature or temperatures.

8. The method of claim 7 in which:
    said step (f) determines the presence of said target temperature subsequent to said excitation interval in correspondence with a substantial diminution of said amplitude of intensity of said detector output.

9. The method of claim 7 in which:
    said step (f) determines the presence of said target temperature subsequent to said excitation interval in correspondence with a decrease in the amplitude of said detector output to a value representing a predetermined ratio of instantaneous amplitude to the maximum amplitude present at said monitor temperature or temperatures.

10. The method of claim 9 in which:
    said predetermined ratio is within a range of about 0.2 to about 0.7.

11. The method of claim 9 in which:
    said predetermined ratio is within a range of about 0.3 to about 0.5.

12. The method of claim 7 in which:
    said step (a) provides a first said untethered implant having a said electromagnetic response at a first said resonant center frequency corresponding with monitor temperatures below a threshold temperature and exhibits a decrease in the intensity of said response when approaching said target temperature, and provides a second said untethered implant having a said electromagnetic response at a second said resonant center frequency different than said first resonant center frequency, corresponding with monitor temperatures below a limit temperature greater than said threshold temperature and exhibits a decrease in the intensity of said response when approaching said limit temperature;

said step (d) positions said first and second untethered implants in thermal transfer relationship with said animal body region;

said step (b) provides said detector output as a first detector output having an amplitude corresponding with said first electromagnetic response and a second detector output having an amplitude corresponding with said second electromagnetic response; and said step (i) controls said heating assembly to elevate the temperature of said subcutaneous region in correspondence with said first and second detector outputs and stops or diminishes said elevation of temperature in correspondence with the substantial diminution of the amplitude of said second detector output.

13. The method of claim 12 in which:

said step (b) provides said detector assembly as deriving a visibly perceptible threshold cue in correspondence with said substantial diminution in said amplitude of said detector output.

14. The method of claim 13 in which:

said step (b) provides said detector assembly as deriving a visibly perceptible limit cue in correspondence with said substantial diminution of the amplitude of said second detector output.

15. The method of claim 12 in which:

said threshold temperature is about 39° C. and said limit temperature is about 70° C.

16. The method of claim 12 in which:

said threshold temperature is about 41° C. and said limit temperature is about 50° C.

17. The method of claim 12 in which:

said threshold temperature is about 42° C. and said limit temperature is about 45° C.

18. The method of claim 12 in which:

said threshold temperature is about 37° C. and said limit temperature is about 41° C.

19. The method of claim 7 in which:

said step (a) provides a first said untethered implant having a said electromagnetic response at a first said resonant center frequency corresponding with monitor temperature below a threshold temperature and exhibits an absence of said response at and above said target temperature, and provides a second said untethered implant having said electromagnetic response at a second said resonant center frequency different than said first resonant center frequency, corresponding with monitor temperatures below a limit temperature greater than said threshold temperature and exhibits an absence of said response when at or above said limit temperature;

said step (d) positions said first and second untethered implants in thermal transfer relationship with said animal body region;

said step (b) provides said detector output as a first detector output corresponding with said first electromagnetic response and a second detector output corresponding with said second electromagnetic response; and said step (i) controls said heating assembly to elevate the temperature of said subcutaneous region in correspondence with said first and second detector outputs and stops said elevation of temperature in correspondence with the absence of said second detector output.

20. The method of claim 19 in which:

said step (b) provides said detector assembly as deriving a visibly perceptible threshold cue in the absence of said first detector output.

21. The method of claim 20 in which:

said step (b) provides said detector assembly as deriving a visibly perceptible limit cue in the absence of said second detector output.

22. The method of claim 1 in which:

said step (a) provides one or more of said passive resonant implants as an untethered passive resonant circuit with an inductor defining winding and core component, said core having a relative permeability characteristic exhibiting a drop in relative permeability toward a unity value at a Curie temperature occurring above said monitor temperature or temperatures and corresponding with said target temperature.

23. The method of claim 1 in which:

said step (a) provides one or more of said passive resonant implants as an untethered passive resonant circuit with an inductor component and a capacitor component, said capacitor component and/or said inductor component exhibiting respective capacitance values and/or inductance values corresponding with said monitor temperature or temperatures.

24. The method of claim 23 in which:

said step (a) provides said one or more passive resonant implants as exhibiting a substantially high Q characteristic to promote a ringing effect within said resonance time.

25. The method of claim 24 in which:

said step (b) provides said detector assembly as deriving said detector output as an average of a plurality of signals corresponding with said antenna detections.

26. The method of claim 1 in which:

said step (b) provides said interrogation assembly as deriving said detector output as a Fourier transform corresponding with said resonant center frequency.

27. The method of claim 1 in which:

said physical parameter is the induction of apoptosis of tissue of said body at said region.

28. The method of claim 1 in which:

said physical parameter is the induction of necrosis of tissue of said body at said region.

29. The method of claim 1 in which:

said monitor temperature is within a range from about 39° C. to about 70° C.

30. The method of claim 1 in which:

said monitor temperature is within a range from about 41° C. to about 50° C.

31. The method of claim 1 in which:

said monitor temperature is within a range from about 42° C. to about 45° C.

32. The method of claim 1 in which:

said monitor temperature is within a range from about 37° C. to about 41° C.

33. The method of claim 1 in which:

said monitor temperature is elevated to within a range from about 4° C. to about 13° C. over normal temperature of the animal body.

34. The method of claim 1 in which:

said monitor temperature is elevated to within a range from about 2° C. to about 33° C. over normal temperature of the animal body.

* * * * *